(12) United States Patent
Branch et al.

(10) Patent No.: US 7,432,270 B2
(45) Date of Patent: Oct. 7, 2008

(54) N-AROYL CYCLIC AMINES

(75) Inventors: Clive Leslie Branch, Harlow (GB); Steven Coulton, Harlow (GB); Amanda Johns, Harlow (GB); Christopher Norbert Johnson, Harlow (GB); Roderick Alan Porter, Harlow (GB); Geoffrey Stemp, Harlow (GB); Kevin Thewlis, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 552 days.

(21) Appl. No.: 10/477,008

(22) PCT Filed: May 2, 2002

(86) PCT No.: PCT/GB02/02042

§ 371 (c)(1),
(2), (4) Date: Nov. 5, 2003

(87) PCT Pub. No.: WO02/090355

PCT Pub. Date: Nov. 14, 2002

(65) Prior Publication Data

US 2004/0143115 A1 Jul. 22, 2004

(30) Foreign Application Priority Data

| May 5, 2001 | (GB) | 0111184.8 |
| May 5, 2001 | (GB) | 0111189.7 |
| Sep. 3, 2001 | (GB) | 0121303.2 |
| Dec. 19, 2001 | (GB) | 0130331.2 |
| Dec. 19, 2001 | (GB) | 0130392.4 |

(51) Int. Cl.
- *A61K 31/498* (2006.01)
- *C07D 403/14* (2006.01)
- *C07D 405/14* (2006.01)
- *C07D 409/14* (2006.01)
- *C07D 417/14* (2006.01)

(52) U.S. Cl. .......... 514/255.05; 544/353; 544/354; 544/355; 544/356

(58) Field of Classification Search .......... 546/197, 546/184; 514/408, 255.05; 544/353, 354, 544/355, 356
See application file for complete search history.

(56) References Cited

U.S. PATENT DOCUMENTS

| 5,547,978 | A * | 8/1996 | Christensen et al. | 514/422 |
| 6,326,379 | B1 * | 12/2001 | Macor et al. | 514/303 |
| 6,677,354 | B2 * | 1/2004 | Branch et al. | 514/318 |
| 6,706,720 | B2 * | 3/2004 | Atwal et al. | 514/259.3 |
| 2004/0180887 | A1 | 9/2004 | Branch et al. | 514/232.5 |
| 2004/0192673 | A1 | 9/2004 | Gaillard et al. | 514/217.04 |
| 2004/0215014 | A1 | 10/2004 | Chan et al. | 540/596 |
| 2006/0040937 | A1 | 2/2006 | Branch et al. | 514/235.5 |

FOREIGN PATENT DOCUMENTS

| WO | WO 00/08015 | 2/2000 |
| WO | WO 00/12077 | 3/2000 |
| WO | WO 00/71508 A2 | 11/2000 |
| WO | WO 01/40231 | 6/2001 |
| WO | WO 01/96302 | 12/2001 |
| WO | WO 02/44172 | 6/2002 |

OTHER PUBLICATIONS

Lang et al., J. Med. Chem., 2004, 47, p. 1153.*
Smart et al., Euro. J. Pharm., 2002, 440, p. 199.*
Smart et al., "Orexins and the treatment of obesity", European Journal of Pharmacology 440 (2002) 199-212.*
Lang et al., "Structure-Activity Studies, etc.," J. Med. Chem. 2004, 47, 1153-1160.*
Kilduff et al., "The hypocretin/orexin, etc.," Trends Neurosi. 2000, 23, 359-365.*

(Continued)

*Primary Examiner*—Patricia L. Morris
(74) *Attorney, Agent, or Firm*—Kathryn L. Sieburth; Mary E. McCarthy; Charles M. Kinzig

(57) ABSTRACT

This invention relates to N-aroyl cyclic amine derivatives and their use as orexin antagonists

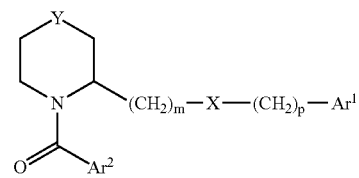

wherein:

Y represents a bond, oxygen, or a group $(CH_2)_n$, wherein n represents 1, 2 or 3;

m represents 1, 2, or 3; p represents ) or 1; X is NR, wherein R is H or $(C_{1-4})$alkyl; $Ar^1$ is aryl, or a mono or bicyclic heteroaryl group containing up to 3 heteroatoms selected from N, O and S; any of which may be optionally substituted; $A^2$ represents phenyl or a 5- or 6-membered heterocyclyl group containing up to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing up to 3 heteroatoms selected from N, O and S; $R^1$ represents hydrogen, optionally substituted $(C_{1-4})$alkoxy, halo, cyano, optionally substituted $(C_{1-6})$alkyl, optionally substituted phenyl, or an optionally substituted 5- or 6-membered heterocyclyl group containing up to 4 heteroatoms selected from N, O and S; when $Ar^1$ is aryl p is not 1, or a pharmaceutical acceptable salt thereof.

13 Claims, No Drawings

OTHER PUBLICATIONS

Taheri et al., "The Role of Hypocretins, etc.," *Annu. Rev. Neurosci.*, 2002, 25: 283-313.*
Cai et al., "Antagonists of the orexin receptors", *Expert Opin. Ther. Patents* (2006) 16(5), 631-646.*
King, "Bioisoteres, Conformational, etc.," Med. Chem: Principle and Practice (1994), 206-208.*
Patini et al., "Bioisosterism: A Rational, etc.," Chem. Rev. 1996, 96, 3147, 3148 and 3170.*
Rubini et al., "Synthesis of, etc.," Tetrahedron, 42 (21), 6039-6045, 1986.*
Mori, et al., "New Synthesis of Pyrrolo-1,4-benzodiazepines by Utilizing Palladium-Catalyzed Carbonylation". *Chem. Pharm. Bull.*, 32(10): 3840-3847 (1984).
Defoin, et al., "Asymmetric Diels-Alder-Cycloadditions with Chiral Carbamoyl Dienophiles". *Helv. Chim. Acta*, 75(1): 109-123 (1992).
Langmead et al. Br. J. Pharmacol., 141: 340-346 (2004).
Porter et al. Bioorg. & Med. Chem. Lett., 11: 1907-1910 (2001).
Duxon et al. Psychopharmacology, 153: 203-209 (2001).
White et al. Peptides, 26: 2331-2338 (2005).
Ishii et al. Behav. Brain Res., 160: 11-24 (2005).
Ishii et al. Behav. Brain Res., 157: 331-341 (2005).
Ishii et al. Physiol. & Behav., 81: 129-140 (2004).
Smith et al. Neurosci. Lett., 341: 256-258 (2003).
Haynes et al. Regulatory Peptides, 104: 153-159 (2002).
Bingham et al. Pain, 92: 81-90 (2001).
Rodgers et al. Eur. J. Neurosci., 13: 1444-1452 (2001).
Smart et al. Br. J. Pharmacol. 132: 1179-1182 (2001).
Jones et al. Psychopharmacology, 153: 210-218 (2001).
Haynes et al. Regulatory Peptides, 96: 45-51 (2000).
Rodgers et al. Neuropeptides, 36(5): 303-325 (2002).
Mori et al. Chem. Pharm. Bull., 32(10): 3840-3847 (1984).
Defoin et al. Helv. Chim. Acta, 75(1): 109-123 (1992).
Boutrel et al. *PNAS*, 102(52): 19168-19173 (2005).
Borgland et al. *Neuron*, 49: 589-601 (2006).
Harris et al. *Nature*, 437: 556-559 (2005).
Brisbare-Roch et al. *Nature Medicine*, 13(2): 150-155 (2007).
Hagan et al. *Proc. Natl. Acad. Sci. USA.*, 96: 10911-10916 (1999).
Piper et al. *Eur. J. Neurosci.*, 12: 726-730 (2000).
Patani et al. *Chem. Rev.*, 96: 3147-3176 (1996).

* cited by examiner

N-AROYL CYCLIC AMINES

This invention relates to N-aroyl cyclic amine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety, addictions; obsessive compulsive disorder; affective neurosis/disorder; depressive neurosis/disorder, anxiety neurosis; dysthymic disorder, behaviour disorder; mood disorder, sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; nausea and vomiting; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy, insomnia; parasomnia; jet-lag syndrome; and neurodegenerative disorders, which includes nosological entities such as disinhibition-dementia-parkironisin-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell,* 1998, 92, 573-585.

There is a significant incidence of obesity in westernised societies. According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaernia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

The present invention provides N-aroyl cyclic amine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders. Additionally these compounds are useful in the treatment of stroke, particularly ischemic or haemorrhagic stroke, and/or blocking the emetic response, i.e. useful in the treatment of nausea and vomiting.

International Patent Applications WO99/09024, WO99/58533, WO00/47577 and WO00/47580 disclose phenyl urea derivatives and WO00/47576 discloses quinolinyl cinnamide derivatives as orexin receptor antagonists. WO01/96302 discloses N-aroyl cyclic amine derivatives.

According to the invention there is provided a compound of formula (I):

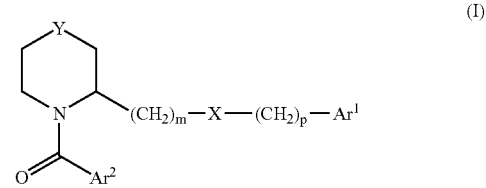

wherein:

Y represents a bond, oxygen, or a group $(CH_2)_n$, wherein n represents 1, 2 or 3 m represents 1, 2, or 3;

p represents 0 or 1;

X is NR, wherein R is H or $(C_{1-4})$alkyl;

$Ar^1$ is aryl, or a mono or bicyclic heteroaryl group containing up to 3 heteroatoms selected from N, O and S; any of which may be optionally substituted;

$Ar^2$ represents phenyl or a 5- or 6-membered heterocyclyl group containing up to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing up to 3 heteroatoms selected from N, O and S;

$R^1$ represents hydrogen, optionally substituted$(C_{1-4})$ alkoxy, halo, cyano, optionally substituted$(C_{1-6})$alkyl, optionally substituted phenyl, or an optionally substituted 5- or 6-membered heterocyclyl group containing up to 4 heteroatoms selected from N, O and S;

wherein when Y is a bond $Ar^2$ can not be 2-naphthyl;

when $Ar^1$ is aryl p is not 1; or a pharmaceutically acceptable salt thereof.

X is preferably NH.

m is preferably 1.

p is preferably 0.

Even more preferably m is 1 when p is 0.

Preferably R is hydrogen.

Alternatively compounds of formula (I) are compounds of formula (Ia);

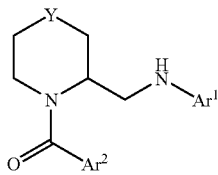

(Ia)

wherein:

Y represents a bond, oxygen, or a group $(CH_2)_n$, wherein n represents 1, 2 or 3

$Ar^1$ is a mono or bicyclic heteroaryl group containing up to 3 heteroatoms selected from N, O and S; any of which may be optionally substituted;

$Ar^2$ represents phenyl or a 5- or 6-membered heterocyclyl group containing up to 3 heteroatoms selected from N, O and S, wherein the phenyl or heterocyclyl group is substituted by $R^1$ and further optional substituents; or $Ar^2$ represents an optionally substituted bicyclic aromatic or bicyclic heteroaromatic group containing up to 3 heteroatoms selected from N, O and S;

$R^1$ represents hydrogen, optionally substituted$(C_{1-4})$ alkoxy, halo, cyano, optionally substituted$(C_{1-6})$alkyl, optionally substituted phenyl, or an optionally substituted 5- or 6-membered heterocyclyl group containing up to 4 heteroatoms selected from N, O and S;

wherein when Y is a bond then $Ar^2$ can not be 2-naphthyl; or pharmaceutically acceptable salts thereof.

Preferably where $Ar^2$ represents phenyl or a 5- or 6-membered heterocyclyl group containing up to 3 heteroatoms selected from N, O and S, the $R^1$ group is situated adjacent to the point of attachment to the amide carbonyl.

Y is preferably a bond, oxygen or $(CH_2)_n$ wherein n is 1 or 2.

Even more preferably Y is a bond, oxygen or $(CH_2)_n$ wherein n is 1

Alternatively $R^1$ represents hydrogen, optionally substituted$(C_{1-4})$alkoxy, halo, optionally substituted$(C_{1-6})$alkyl, optionally substituted phenyl or an optionally substituted 5- or 6-membered heterocyclyl group containing up to 3 heteroatoms selected from N, O and S.

Alternatively $R^1$ represents optionally substituted$(C_{1-4})$ alkoxy, halo, optionally substituted$(C_{1-6})$alkyl, optionally substituted phenyl or an optionally substituted 5- or 6-membered heterocyclyl group containing up to 3 heteroatoms selected from N, O and S.

Preferably $R^1$ is selected from trifluoromethoxy, methoxy, ethoxy, halo, cyano or an optionally substituted phenyl, pyridyl, pyrazolyl, pyrimidinyl, or oxadiazolyl group.

More preferably $R^1$ is selected from trifluoromethoxy, methoxy, ethoxy, halo, or an optionally substituted phenyl, pyridyl, pyrazolyl, pyrimidinyl, or oxadiazolyl group.

When $Ar^1$ is optionally substituted aryl it is preferably phenyl. $Ar^1$ may have up to 5, preferably 1, 2 or 3 optional substituents.

Examples of when $Ar^1$ is a mono or bicyclic heteroaryl are quinoxalinyl, quinazolinyl, pyridopyrazinyl, benzoxazolyl, benzothiophenyl, benzimidazolyl, naphthyridinyl, pyridinyl, pyrimidinyl, or thiazolyl. Additionally $Ar^1$ can be selected from pyridazinyl, pyrazinyl, oxazolyl, triazolyl, imidazolyl, pyrazolyl, quinolinyl, benzofuranyl, indolyl, benzothiazolyl, oxazolyl[4,5-b]pyridiyl, pyridopyrimidinyl or isoquinolinyl. Furthermore $Ar^1$ can be furanyl or thienyl.

Preferably $Ar^1$ is benzoxazolyl, benzimidazolyl, quinoxalinyl, quinazolinyl, pyrimidinyl, pyridinyl, naphthyridinyl, Additionally $Ar^1$ can be quinolinyl, pyridopyrimidine, thiazolyl, oxazolylpyridinyl, benzothiazolyl, isoquinolinyl or pyrazinyl.

More preferably $Ar^1$ is benzoxazolyl, benzimidazolyl, quinoxalinyl, quinazolinyl, pyrimidinyl, pyridinyl, naphthyridinyl or oxazolyl[4,5-b]pyridinyl.

When $Ar^2$ is a 5- or 6-membered heterocyclyl group containing up to 3 heteroatoms selected from N, O and S, it may be furanyl, thienyl, pyrrolyl, oxazolyl, thiazolyl, imidazolyl, oxadiazolyl, thiadiazolyl, pyridyl, triazolyl, triazinyl, pyridazinyl, pyrimidinyl, isothiazolyl, isoxazolyl, pyrazinyl or pyrazolyl.

When $R^1$ is a 5- or 6-membered heterocyclyl group containing up to 4 heteroatoms selected from N, O and S, it may be furanyl, thienyl, pyrrolyl, oxazolyl, thiazolyl, imidazolyl, oxadiazolyl, thiadiazolyl, pyridyl, triazolyl, triazinyl, pyridazinyl, pyrimidinyl, isothiazolyl, isoxazolyl, pyrazinyl or pyrazolyl. Additionally it can be tetrazoyl, piperazinyl, piperidinyl, morpholinyl or thiomorpholinyl.

Preferably when $R^1$ is a 5- or 6-membered heterocyclic ring containing up to 4 heteroatoms selected from N, O and S, it is furanyl, thienyl, pyrrolyl, oxazolyl, thiazolyl, imidazolyl, oxadiazolyl, thiadiazolyl, pyridyl, triazolyl, triazinyl, pyridazinyl, pyrimidinyl, isothiazolyl, isoxazolyl, pyrazinyl or pyrazolyl.

Preferably $R^1$ is a 5- or 6membered heterocyclic ring it contains up to 3 heteroatoms selected from N, O and S.

When $Ar^2$ is an optionally substituted bicyclic aromatic or bicyclic heteroaromatic it is selected from benzofuryl, benzimidazolyl, quinolinyl, quinoxalinyl or naphthyl. Additionally it may be benzotriazolyl, benzothienyl, benzoxazolyl, naphthyridinyl, isoquinolinyl or quinazolinyl. Furthermore it can be indolyl, benzothiazolyl, or benzothiadiazolyl.

Preferably $Ar^2$ represents optionally substituted phenyl, pyridyl, thiazolyl, pyrazolyl, benzofuryl, naphthyl, triazolyl, quinoxalinyl, quinolinyl, isoquinolinyl, benzimidazolyl, benzothienyl, benzotriazolyl, benzothiazolyl, indolyl or thienyl.

Alternatively $Ar^2$ represents optionally substituted phenyl, pyridyl, thiazolyl, pyrazolyl, benzofuryl, naphthyl or triazolyl. Preferably the triazolyl is 1,2,3-triazolyl.

More preferably $Ar^2$ represents optionally substituted thiazolyl, pyrazolyl or quinolinyl.

Alternatively $R^1$ is selected from trifluoromethoxy, methoxy, halo, or an optionally substituted phenyl, pyridyl, pyrazolyl or oxadiazolyl group Even more preferably $R^1$ represents a trifluoromethoxy group, methoxy group, iodo, or an optionally substituted phenyl, pyridyl, or oxadiazolyl group.

Optional substituents for the groups $Ar^1$, $Ar^2$, R and $R^1$ include halogen, hydroxy, oxo, cyano, nitro, $(C_{1-4})$alkyl, $(C_{1-4})$alkoxy, hydroxy$(C_{1-4})$alkyl, hydroxy$(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, or aryl$(C_{1-4})$alkanoyl group; a group $R^aR^bN-$, $R^aOCO(CH_2)_r$, $R^aCON(R^a)(CH_2)_r$, $R^aR^bNCO(CH_2)_r$, $R^aR^bNSO_2(CH_2)_r$ or $R^aSO_2NR^b(CH_2)_r$ where each of $R^a$ and $R^b$ independently represents a hydrogen atom or a $(C_{1-4})$alkyl group or where appropriate $R^aR^b$ forms part of a $(C_{3-6})$azacyloalkane or $(C_{3-6})$(2-oxo)azacycloalkane ring and r represents zero or an integer from 1 to 4. Additional substituents are $(C_{1-4})$acyl, aryl, aryl$(C_{1-4})$alkyl, $(C_{1-4})$alkylamino$(C_{1-4})$alkyl, $R^aR^bN(CH_2)_n-$, $R^aR^bN(CH_2)nO-$, wherein n represents an from 1 to 4 Additionally when the substituent is $R^aR^bN(CH_2)n-$ or $R^aR^bN(CH_2)nO$, $R^a$ with at least one $CH_2$ of the $(CH_2)n$ portion of the group form a $(C_{3-6})$azacycloalkane and $R^b$ represents hydrogen, a $(C_{1-4})$alkyl group or with the nitrogen to which it is attached forms a second $(C_{3-6})$azacycloalkane fused to the first $(C_{3-6})$azacycloalkane.

Preferred optional substituents for $Ar^2$ are halogen, cyano, $(C_{1-4})$alkyl. Additional preferred optional substituents are hydroxy$(C_{1-4})$alkyl, $(C_{1-4})$alkoxy$(C_{1-4})$alkyl, $R^aR^bN(CH_2)n$, $R^aR^bN$. Further optional substituents for $Ar^2$ can also be halogen, cyano, $(C_{1-4})$alkyl, $R^aR^bN(CH_2)nO$ or $(C_{1-4})$alkoxy.

Preferred optional substituents for $Ar^1$ are halogen, cyano, $(C_{1-4})$alkanoyl. Other preferred substituents are hydroxy $(C_{1-4})$ alkyl, $(C_{1-4})$alkyl or $CF_3$.

Preferred optional substituents for $R^1$ are halogen, $(C_{1-4})$alkoxy$(C_{1-4})$alkyl, $R^aR^bN$, $R^ar^bN(CH_2)nO$ and $R^aR^bN(CH_2)$n. Other preferred substituents are $(C_{1-4})$alkoxy or $(C_{1-4})$alkanoyl.

In the groups $Ar^1$ and $Ar^2$, substituents positioned ortho to one another may be linked to form a ring.

Illustrative compounds of formula (I) are selected from:

| Example | Compound Name |
|---|---|
| 1 | 1-[2-(Benzooxazol-2-ylaminomethyl)-piperidin-1-yl]-1-(2-methyl-5-phenyl-thiazol-4-yl)-methanone. |
| 2 | 1-[2-(Benzooxazol-2-ylaminomethyl)-piperidin-1-yl]-1-biphenyl-2-yl-methanone |
| 3 | 1-[2-(Benzooxazol-2-ylaminomethyl)-piperidin-1-yl]-1-[2-(3-methyl-[1,2,4]oxadiazol-5-yl)-phenyl]-methanone |
| 4 | 1-[2-(Benzooxazol-2-ylaminomethyl)-piperidin-1-yl]-1-(2-trifluoromethoxy-phenyl)-methanone |
| 5 | 1-[2-(Benzooxazol-2-ylaminomethyl)-piperidin-1-yl]-1-naphthalen-1-yl-methanone |
| 6 | 1-[2-(Benzooxazol-2-ylaminomethyl)-piperidin-1-yl]-1-(2-methoxy-phenyl)-methanone |
| 7 | 1-[2-(Benzooxazol-2-ylaminomethyl)-piperidin-1-yl]-1-(2-iodo-phenyl)-methanone |
| 8 | 1-[(S)-2-(Benzooxazol-2-ylaminomethyl)-piperidin-1-yl]-1-(2-trifluoromethoxy-phenyl)-methanone |
| 9 | 1-[(S)-2-(Benzooxazol-2-ylaminomethyl)-piperidin-1-yl]-1-[2-(3-methyl-[1,2,4]oxadiazol-5-yl)-phenyl]-methanone |
| 10 | 1-[(S)-2-(Benzooxazol-2-ylaminomethyl)-piperidin-1-yl]-1-biphenyl-2-yl-methanone |
| 11 | 1-[(S)-2-(Benzooxazol-2-ylaminomethyl)-piperidin-1-yl]-1-(2-iodo-phenyl)-methanone |
| 12 | 1-[2-Benzooxazol-2-ylaminomethyl)-piperidin-1-yl]-1-phenyl-methanone |
| 13 | 1-{2-[(1H-Benzoimidazol-2-ylamino)-methyl]-piperidin-1-yl}-1-[5-(4-fluoro-phenyl)-2-methyl-thiazol-4-yl]-methanone |
| 14 | 1-{2-[(1H-Benzoimidazol-2-ylamino)-methyl]-piperidin-1-yl}-1-[2-(3-methyl-[1,2,4]oxadiazol-5-yl)-phenyl]-methanone |
| 15 | 1-[2-(Benzothiazol-2-ylaminomethyl)-piperidin-1-yl]-1-[2-(3-methyl-[1,2,4]oxadiazol-5-yl)-phenyl]-methanone |
| 16 | 1-[2-(Benzothiazol-2-ylaminomethyl)-piperidin-1-yl]-1-(2-trifluoromethoxy-phenyl)-methanone |
| 17 | 1-[2-(Benzothiazol-2-ylaminomethyl)-piperidin-1-yl]-1-biphenyl-2-yl-methanone |
| 18 | 1-[2-(Benzothiazol-2-ylaminomethyl)-piperidin-1-yl]-1-(2-methyl-5-phenyl-thiazol-4-yl)-methanone |
| 19 | 1-[5-(4-Fluoro-phenyl)-2-methyl-thiazol-4-yl]-1-[2-(isoquinolin-1-ylaminomethyl)-piperidin-1-yl]-methanone |
| 20 | 1-[2-(Isoquinolin-1-ylaminomethyl)-piperidin-1-yl]-1-[2-(3-methyl-[1,2,4]oxadiazol-5-yl)-phenyl]-methanone |
| 21 | 1-[2-Isoquinolin-1-ylaminomethyl)-piperidin-1-yl]-1-(2-trifluoromethoxy-phenyl)-methanone |

-continued

| Example | Compound Name |
|---|---|
| 22 | 1-(2-Iodo-phenyl)-1-[2-(isoquinolin-1-ylaminomethyl)-piperidin-1-yl]-methanone |
| 23 | 1-[2-(Isoquinolin-1-ylaminomethyl)-piperidin-1-yl]-1-naphthalen-1-yl-methanone |
| 24 | 1-[2-(Quinoxalin-2-ylaminomethyl)-piperidin-1-yl]-1-(2-trifluoromethoxy-phenyl)-methanone |
| 25 | 1-[2-(Quinoxalin-2-ylaminomethyl)-piperidin-1-yl]-1-(3-trifluoromethoxy-phenyl)-methanone |
| 26 | 1-(2-Iodo-phenyl)-1-[2-(quinoxalin-2-ylaminomethyl)-piperidin-1-yl]-methanone |
| 27 | 1-[5-(4-Fluoro-phenyl)-2-methyl-thiazol-4-yl]-1-[2-(quinoxalin-2-ylaminomethyl)-piperidin-1-yl]-methanone |
| 28 | 1-[2-(3-Methyl-[1,2,4]oxadiazol-5-yl)-phenyl]-1-[2-(quinoxalin-2-ylaminomethyl)-piperidin-1-yl]-methanone |
| 29 | 1-[5-(4-Fluoro-phenyl)-2-methyl-thiazol-4-yl]-1-[(R)-2-(quinazolin-2-ylaminomethyl)-piperidin-1-yl]-methanone |
| 30 | 1-[5-(4-Fluoro-phenyl)-2-methyl-thiazol-4-yl]-1-[(S)-2-([1,5]naphthyridin-2-ylaminomethyl)-piperidin-1-yl]-methanone |
| 31 | 1-[5-(4-Fluoro-phenyl)-2-methyl-thiazol-4-yl]-1-[(S)-2-([1,8]naphthyridin-2-ylaminomethyl)-piperidin-1-yl]-methanone |
| 32 | 1-[(S)-2-(Benzooxazol-2-ylaminomethyl)-piperidin-1-yl]-1-[5-(4-fluoro-phenyl)-2-methyl-thiazol-4-yl]-methanone |
| 33 | 1-[3-(Benzooxazol-2-ylaminomethyl)-morpholin-4-yl]-1-[2-(3-methyl-[1,2,4]oxadiazol-5-yl)-phenyl]-methanone |
| 34 | 1-[5-(4-Fluoro-phenyl)-2-methyl-thiazol-4-yl]-1-[2-(quinolin-2-ylaminomethyl)-piperidin-1-yl]-methanone |
| 35 | 1-[2-(3-Methyl-[1,2,4]oxadiazol-5-yl)-phenyl]-1-[2-(quinolin-2-ylaminomethyl)-piperidin-1-yl]-methanone |
| 36 | 1-[2-(Quinolin-2-ylaminomethyl)-piperidin-1-yl]-1-(2-trifluoromethoxy-phenyl)-methanone |
| 37 | 1-[2-(Benzothiazol-2-ylaminomethyl)-piperidin-1-yl]-1-naphthalen-1-yl-methanone |
| 38 | 1-[5-(4-Fluoro-phenyl)-2-methyl-thiazol-4-yl]-1-[(S)-2-(quinolin-2-ylaminomethyl)-piperidin-1-yl]-methanone |
| 39 | 1-[5-(4-Fluoro-phenyl)-2-methyl-thiazol-4-yl]-1-[2-(pyrimidin-2-ylaminomethyl)-piperidin-1-yl]-methanone |
| 40 | 1-[2-(3-Methyl-[1,2,4]oxadiazol-5-yl)-phenyl]-1-[2-(pyrimidin-2-ylaminomethyl)-piperidin-1-yl]-methanone |
| 41 | 1-[5-(4-Fluoro-phenyl)-2-methyl-thiazol-4-yl]-1-[2-(pyrazin-2-ylaminomethyl)-piperidin-1-yl]-methanone |
| 42 | 1-[5-(4-Fluoro-phenyl)-2-methyl-thiazol-4-yl]-1-[(S)-2-(quinazolin-4-ylaminomethyl)-piperidin-1-yl]-methanone |
| 43 | 1-[5-(4-Fluoro-phenyl)-thiazol-4-yl]-1-[(S)-2-(quinazolin-4-ylaminomethyl)-piperidin-1-yl]-methanone |
| 44 | 1-[4-(4-Fluoro-phenyl)-1-methyl-1H-pyrazol-3-yl]-1-[(S)-2-(quinazolin-4-ylaminomethyl)-piperidin-1-yl]-methanone |
| 45 | 1-[4-(4-Fluoro-phenyl)-2-methyl-2H-pyrazol-3-yl]-1-[(S)-2-(quinazolin-4-ylaminomethyl)-piperidin-1-yl]-methanone |
| 46 | 1-[4-(4-Fluoro-phenyl)-1H-pyrazol-3-yl]-1-[(S)-2-(quinazolin-4-ylaminomethyl)-piperidin-1-yl]-methanone |
| 47 | 1-[5-(3-Fluoro-phenyl)-2-methyl-thiazol-4-yl]-1-[(S)-2-(quinazolin-4-ylaminomethyl)-piperidin-1-yl]-methanone |
| 48 | 1-[5-(3-Fluoro-phenyl)-2-methyl-2H-[1,2,3]triazol-4-yl]-1-[(S)-2-(quinazolin-4-ylaminomethyl)-piperidin-1-yl]-methanone |
| 49 | 1-Naphthalen-1-yl-1-[(S)-2-(quinazolin-4-ylaminomethyl)-piperidin-1-yl]-methanone |
| 50 | 1-(5-Bromo-2-methoxy-phenyl)-1-[(S)-2-(quinazolin-4-ylaminomethyl)-piperidin-1-yl]-methanone |
| 51 | 1-[2-(3-Methyl-[1,2,4]oxadiazol-5-yl)-phenyl]-1-[(S)-2-(quinazolin-4-ylaminomethyl)-piperidin-1-yl]-methanone |
| 52 | 1-[(S)-2-(Quinazolin-4-ylaminomethyl)-piperidin-1-yl]-1-(2-trifluoromethoxy-phenyl)-methanone |
| 53 | 1-{(S)-2-[(6,7-Difluoro-3-methyl-quinoxalin-2-ylamino)-methyl]-piperidin-1-yl}-1-[5-(4-fluoro-phenyl)-2-methyl-thiazol-4-yl]-methanone |
| 54 | 1-{(S)-2-[(6,7-Difluoro-3-methyl-quinoxalin-2-ylamino)-methyl]-piperidin-1-yl}-1-[5-(4-fluoro-phenyl)-thiazol-4-yl]-methanone |
| 55 | 1-{(S)-2-[(6,7-Difluoro-3-methyl-quinoxalin-2-ylamino)-methyl]-piperidin-1-yl}-1-[4-(4-fluoro-phenyl)-1-methyl-1H-pyrazol-3-yl]-methanone |
| 56 | 1-{(S)-2-[(6,7-Difluoro-3-methyl-quinoxalin-2-ylamino)-methyl]-piperidin-1-yl}-1-[4-(4-fluoro-phenyl)-1H-pyrazol-3-yl]-methanone |
| 57 | 1-{(S)-2-[(6,7-Difluoro-3-methyl-quinoxalin-2-ylamino)-methyl]-piperidin-1-yl}-1-[2-(4-fluoro-phenyl)-5-methyl-2H-pyrazol-3-yl]-methanone |
| 58 | 1-{(S)-2-[(6,7-Difluoro-3-methyl-quinoxalin-2-ylamino)-methyl]-piperidin-1-yl}-1-[4-(4-fluoro-phenyl)-2-methyl-2H-pyrazol-3-yl]-methanone |
| 59 | 1-{(S)-2-[(6,7-Difluoro-3-methyl-quinoxalin-2-ylamino)-methyl]-piperidin-1-yl}-1-naphthalen-1-yl-methanone |

-continued

| Example | Compound Name |
|---|---|
| 60 | 1-{(S)-2-[(6,7-Difluoro-quinoxalin-2-ylamino)-methyl]-piperidin-1-yl}-1-quinolin-4-yl-methanone |
| 61 | 1-{(S)-2-[(6,7-Difluoro-quinoxalin-2-ylamino)-methyl]-piperidin-1-yl}-1-[5-(4-fluoro-phenyl)-2-methyl-oxazol-4-yl]-methanone |
| 62 | 1-{(S)-2-[(6,7-Difluoro-quinoxalin-2-ylamino)-methyl]-piperidin-1-yl}-1-[5-(4-fluoro-phenyl)-2-methyl-thiazol-4-yl]-methanone |
| 63 | 1-{(S)-2-[(6,7-Difluoro-quinoxalin-2-ylamino)-methyl]-piperidin-1-yl}-1-[2-(3-methyl-[1,2,4]oxadiazol-5-yl)-phenyl]-methanone |
| 64 | 1-{(S)-2-[(6,7-Difluoro-quinoxalin-2-ylamino)-methyl]-piperidin-1-yl}-1-(2-trifluoromethoxy-phenyl)-methanone |
| 65 | 1-Biphenyl-2-yl-1-{(S)-2-[(6,7-difluoro-quinoxalin-2-ylamino)-methyl]-piperidin-1-yl}-methanone |
| 66 | 1-(5-Bromo-2-methoxy-phenyl)-1-{(S)-2-[(6,7-difluoro-quinoxalin-2-ylamino)-methyl]-piperidin-1-yl}-methanone |
| 67 | 1-{(S)-2-[6,7-Difluoro-quinoxalin-2-ylamino)-methyl]-piperidin-1-yl}-1-[4-(4-fluoro-phenyl)-1-methyl-1H-pyrazol-3-yl]-methanone |
| 68 | 1-{(S)-2-[(6,7-Difluoro-quinoxalin-2-ylamino)-methyl]-piperidin-1-yl}-1-[4-(4-fluoro-phenyl)-2-methyl-2H-pyrazol-3-yl]-methanone |
| 69 | 1-{(S)-2-[(6,7-Difluoro-quinoxalin-2-ylamino)-methyl]-piperidin-1-yl}-1-[5-(4-fluoro-phenyl)-2-methyl-2H-[1,2,3]triazol-4-yl]-methanone |
| 70 | 1-{(S)-2-[(6,7-Difluoro-quinoxalin-2-ylamino)-methyl]-piperidin-1-yl}-1-naphthalen-1-yl-methanone |
| 71 | 1-{(S)-2-[(6,7-Difluoro-quinoxalin-2-ylamino)-methyl]-piperidin-1-yl}-1-[5-(4-fluoro-phenyl)-thiazol-4-yl]-methanone |
| 72 | 1-[4-(4-Fluoro-phenyl)-1-methyl-1H-pyrazol-3-yl]-1-[(R)-2-(quinazolin-2-ylaminomethyl)-piperidin-1-yl]-methanone |
| 73 | 1-[2-(3-Methyl-[1,2,4]oxadiazol-5-yl)-phenyl]-1-[2-(oxazolo[4,5-b]pyridin-2-ylaminomethyl)-piperidin-1-yl]-methanone |
| 74 | 1-[2-(Oxazolo[4,5-b]pyridin-2-ylaminomethyl)-piperidin-1-yl]-1-(2-trifluoromethoxy-phenyl)-methanone |
| 75 | 1-[5-(4-Fluoro-phenyl)-2-methyl-thiazol-4-yl]-1-[2-(oxazolo[4,5-b]pyridin-2-ylaminomethyl)-piperidin-1-yl]-methanone |
| 76 | 1-(2-Iodo-phenyl)-1-[2-(oxazolo[4,5-b]pyridin-2-ylaminomethyl)-piperidin-1-yl]-methanone |
| 77 | 1-{3-[(6,7-Difluoro-quinoxalin-2-ylamino)-methyl]-morpholin-4-yl}-1-[5-(4-fluoro-phenyl)-2-methyl-thiazol-4-yl]-methanone |
| 78 | 1-{3-[(6,7-Difluoro-quinoxalin-2-ylamino)-methyl]-morpholin-4-yl}-1-[4-(4-fluoro-phenyl)-1-methyl-1H-pyrazol-3-yl]-methanone |
| 79 | 1-{3-[(6,7-Difluoro-quinoxalin-2-ylamino)-methyl]-morpholin-4-yl}-1-[4-(4-fluoro-phenyl)-2-methyl-2H-pyrazol-3-yl]-methanone |
| 80 | 1-[5-(4-Fluoro-phenyl)-2-methyl-thiazol-4-yl]-1-[(S)-2-(pyrido[2,3-b]pyrazin-2-ylaminomethyl)-piperidin-1-yl]-methanone |
| 81 | 1-[5-(4-Fluoro-phenyl)-2-methyl-thiazol-4-yl]-1-[(S)-2-(pyrido[2,3-b]pyrazin-3-ylaminomethyl)-piperidin-1-yl]-methanone |
| 82 | 1-[5-(4-Fluoro-phenyl)-2-methyl-thiazol-4-yl]-1-{2-[(4-phenyl-thiazol-2-ylamino)-methyl]-piperidin-1-yl}-methanone |
| 93 | 1-{2-[(6,7-Difluoro-quinoxalin-2-ylamino)-methyl]-pyrrolidin-1-yl}-1-[4-(4-fluoro-phenyl)-2H-pyrazol-3-yl]-methanone |
| 94 | 1-{2-[(6,7-Difluoro-quinoxalin-2-ylamino)-methyl]-pyrrolidin-1-yl}-1-[5-(4-fluoro-phenyl)-2-methyl-thiazol-4-yl]-methanone |
| 95 | 1-{2-[(6,7-Difluoro-quinoxalin-2-ylamino)-methyl]-pyrrolidin-1-yl}-1-[2-(4-fluoro-phenyl)-5-methyl-2H-pyrazol-3-yl]-methanone |
| 96 | 1-{2-[(6,7-Difluoro-quinoxalin-2-ylamino)-methyl]-pyrrolidin-1-yl}-1-[5-(4-fluoro-phenyl)-2-methyl-2H-[1,2,3]triazol-4-yl]-methanone |
| 97 | 2-(1-{2-[(6,7-Difluoro-quinoxalin-2-ylamino)-methyl]-pyrrolidin-1-yl}-methanoyl)-benzonitrile |
| 98 | 1-{2-[(6,7-Difluoro-quinoxalin-2-ylamino)-methyl]-pyrrolidin-1-yl}-1-naphthalen-1-yl-methanone |
| 99 | 1-(5-Bromo-2-methoxy-phenyl)-1-{2-[(6,7-difluoro-quinoxalin-2-ylamino)-methyl]-pyrrolidin-1-yl}-methanone |
| 100 | 1-{2-[(6,7-Difluoro-quinoxalin-2-ylamino)-methyl]-pyrrolidin-1-yl}-1-[2-(3-methyl-[1,2,4]oxadiazol-5-yl)-phenyl]-methanone |
| 101 | 1-{(S)-2-[(6,7-Difluoro-quinoxalin-2-ylamino)-methyl]-pyrrolidin-1-yl}-1-[5-(4-fluoro-phenyl)-2-methyl-thiazol-4-yl]-methanone |
| 102 | 1-{(S)-2-[(6,7-Difluoro-quinoxalin-2-ylamino)-methyl]-pyrrolidin-1-yl}-1-[5-(4-fluoro-phenyl)-thiazol-4-yl]-methanone |
| 103 | 1-{(S)-2-[(6,7-Difluoro-quinoxalin-2-ylamino)-methyl]-pyrrolidin-1-yl}-1-[2-(3-methyl-[1,2,4]oxadiazol-5-yl)-phenyl]-methanone |
| 104 | 1-{(S)-2-[(6,7-Difluoro-quinoxalin-2-ylamino)-methyl]-pyrrolidin-1-yl}-1-[4-(4-fluoro-phenyl-1H-pyrazol-3-yl]-methanone |
| 105 | 1-[2-(3-Methyl-[1,2,4]oxadiazol-5-yl)-phenyl]-1-[(S)-2-(oxazolo[4,5-b]pyridin-2-ylaminomethyl)-piperidin-1-yl]-methanone |
| 106 | 1-[2-(3-Methyl-[1,2,4]oxadiazol-5-yl)-phenyl]-1-{(S)-2-[(methyl-oxazolo[4,5-b]pyridin-2-yl-amino)-methyl]-piperidin-1-yl}-methanone |
| 83 | 1-{(S)-2-[(6,7-Difluoro-quinoxalin-2-ylamino)-methyl]-piperidin-1-yl}-1-quinoxalin-2-yl-methanone |

-continued

| Example | Compound Name |
|---|---|
| 84 | 1-{(S)-2-[(6,7-Difluoro-quinoxalin-2-ylamino)-methyl]-piperidin-1-yl}-1-quinolin-3-yl-methanone |
| 85 | 1-{(S)-2-[(6,7-Difluoro-quinoxalin-2-ylamino)-methyl]-piperidin-1-yl}-1-isoquinolin-3-yl-methanone |
| 86 | 1-{(S)-2-[(6,7-Difluoro-quinoxalin-2-ylamino)-methyl]-piperidin-1-yl}-1-(2-methoxy-pyridin-3-yl)-methanone |
| 87 | 1-{(S)-2-[(6,7-Difluoro-quinoxalin-2-ylamino)-methyl]-piperidin-1-yl}-1-quinoxalin-6-yl-methanone |
| 88 | 6-[((S)-1-{1-[4-(4-Fluoro-phenyl)-1-methyl-1H-pyrazol-3-yl]-methanoyl}-piperidin-2-ylmethyl)-amino]-nicotinonitrile |
| 89 | 1-[5-(4-Fluoro-phenyl)-2-methyl-thiazol-4-yl]-1-{(S)-2-[(4-trifluoromethyl-pyrimidin-2-ylamino)-methyl]-piperidin-1-yl}-methanone |
| 90 | 1-(1H-Benzoimidazol-5-yl)-1-[(S)-2-(pyrido[2,3-b]pyrazin-2-ylaminomethyl)-piperidin-1-yl]-methanone<br>Duplicate of Example 161 |
| 91 | 1-{(S)-2-[(6,7-Difluoro-quinoxalin-2-ylamino)-methyl]-piperidin-1-yl}-1-[2-dimethylamino-5-(4-fluoro-phenyl)-thiazol-4-yl]-methanone |
| 92 | 1-{(S)-2-[(6,7-Difluoro-quinoxalin-2-ylamino)-methyl]-piperidin-1-yl}-1-[2-(3-dimethylamino-propoxy)-phenyl]-methanone |
| 107 | 6-[((S)-1-{1-[4-(4-Fluoro-phenyl)-1-methyl-1H-pyrazol-3-yl]-methanoyl}-piperidin-2-ylmethyl)-methyl-amino]-nicotinonitrile |
| 108 | 1-((S)-2-{[(6,7-Difluoro-quinoxalin-2-yl)-methyl-amino]-methyl}-piperidin-1-yl)-1-[4-(4-fluoro-phenyl)-1-methyl-1H-pyrazol-3-yl]-methanone | and pharmaceutically acceptable salts thereof.

Additional compounds of formula (I) are selected from:

| Example | Compound Name |
|---|---|
| 109 | 1-{(S)-2-[(6,7-Difluoro-quinoxalin-2-ylamino)-methyl]-piperidin-1-yl}-1-(4-fluoro-benzofuran-2-yl)-methanone |
| 110 | 2-[((S)-1-{1-[5-(4-Fluoro-phenyl)-2-methyl-thiazol-4-yl]-methanoyl}-piperidin-2-ylmethyl)-amino]-nicotinonitrile |
| 111 | 2-[((S)-1-{1-[2-(3-Methyl-[1,2,4]oxadiazol-5-yl)-phenyl]-methanoyl}-piperidin-2-ylmethyl)-amino]-nicotinonitrile |
| 112 | 2-[((S)-1-{1-[5-(4-Fluoro-phenyl)-2-methyl-thiazol-4-yl]-methanoyl}-piperidin-2-ylmethyl)-amino]-isonicotinonitrile |
| 113 | 1-Benzo[b]thiophen-2-yl-1-{(S)-2-[(6,7-difluoro-quinoxalin-2-ylamino)-methyl]-piperidin-1-yl}-methanone |
| 114 | 1-(1H-Benzoimidazol-5-yl)-1-{(S)-2-[(6,7-difluoro-quinoxalin-2-ylamino)-methyl]-piperidin-1-yl}-methanone |
| 115 | 1-(1H-Benzotriazol-5-yl)-1-{(S)-2-[(6,7-difluoro-quinoxalin-2-ylamino)-methyl]-piperidin-1-yl}-methanone |
| 116 | 1-Benzothiazol-6-yl-1-{(S)-2-[(6,7-difluoro-quinoxalin-2-ylamino)-methyl]-piperidin-1-yl}-methanone |
| 117 | 1-(3,4-Dichloro-phenyl)-1-{(S)-2-[(6,7-difluoro-quinoxalin-2-ylamino)-methyl]-piperidin-1-yl}-methanone |
| 118 | 1-{(S)-2-[(6,7-Difluoro-quinoxalin-2-ylamino)-methyl]-piperidin-1-yl}-1-(3,4-dimethoxy-phenyl)-methanone |
| 121 | 1-Isoquinolin-3-yl-1-[(S)-2-(pyrido[2,3-b]pyrazin-2-ylaminomethyl)-piperidin-1-yl]-methanone |
| 122 | 1-(1H-Indol-5-yl)-1-[(S)-2-(pyrido[2,3-b]pyrazin-2-ylaminomethyl)-piperidin-1-yl]-methanone |
| 123 | 1-[(S)-2-(Pyrido[2,3-b]pyrazin-2-ylaminomethyl)-piperidin-1-yl]-1-quinolin-4-yl-methanone |
| 124 | 1-{(S)-2-[(6,7-Difluoro-quinoxalin-2-ylamino)-methyl]-piperidin-1-yl}-1-[4-(4-fluoro-phenyl)-1-(2-methoxy-ethyl)-1H-pyrazol-3-yl]-methanone |
| 125 | 1-{(S)-2-[(6,7-Difluoro-quinoxalin-2-ylamino)-methyl]-piperidin-1-yl}-1-(2,4-dimethyl-thiazol-5-yl)-methanone |
| 126 | 1-{(S)-2-[(6,7-Difluoro-quinoxalin-2-ylamino)-methyl]-piperidin-1-yl}-1-[5-(4-fluoro-phenyl)-1-methyl-1H-[1,2,3]triazol-4-yl]-methanone |
| 127 | 6-[((S)-1-{1-[4-(4-Fluoro-phenyl)-1-(2-methoxy-ethyl)-1H-pyrazol-3-yl]-methanoyl}-piperidin-2-ylmethyl)-amino]-nicotinonitrile |
| 128 | 1-{(S)-2-[(5-Bromo-pyrimidin-2-ylamino)-methyl]-piperidin-1-yl}-1-[5-(4-fluoro-phenyl)-2-methyl-thiazol-4-yl]-methanone |
| 129 | 1-{(S)-2-[(5-Bromo-pyrimidin-2-ylamino)-methyl]-piperidin-1-yl}-1-[4-(4-fluoro-phenyl)-1H-pyrazol-3-yl]-methanone |
| 130 | 1-{(S)-2-[(5-Bromo-pyrimidin-2-ylamino)-methyl]-piperidin-1-yl}-1-[5-(4-fluoro-phenyl)-2H-[1,2,3]triazol-4-yl]-methanone |
| 131 | 1-{(S)-2-[(5-Bromo-pyrimidin-2-ylamino)-methyl]-piperidin-1-yl}-1-quinolin-2-yl-methanone |

-continued

| Example | Compound Name |
|---|---|
| 132 | 1-{(S)-2-[(5-Bromo-pyrimidin-2-ylamino)-methyl]-piperidin-1-yl}-1-[5-(4-fluoro-phenyl)-1-methyl-1H-[1,2,3]triazol-4-yl]-methanone |
| 133 | 1-{(S)-2-[(5-Bromo-pyrimidin-2-ylamino)-methyl]-piperidin-1-yl}-1-[5-(4-fluoro-phenyl)-2-hydroxymethyl-thiazol-4-yl]-methanone |
| 134 | 1-{(S)-2-[(5-Bromo-pyrimidin-2-ylamino)-methyl]-piperidin-1-yl}-1-[2-(3-methyl-[1,2,4]oxadiazol-5-yl)-phenyl]-methanone |
| 135 | 1-{(S)-2-[(5-Bromo-pyrimidin-2-ylamino)-methyl]-piperidin-1-yl}-1-quinolin-8-yl-methanone |
| 136 | 2-{[(S)-1-(1-1H-Benzoimidazol-5-yl-methanoyl)-piperidin-2-ylmethyl]-amino}-6,7-difluoro-quinoline-3-carbonitrile |
| 137 | 6,7-Difluoro-2-{[(S)-1-(1-isoquinolin-3-yl-methanoyl)-piperidin-2-ylmethyl]-amino}-quinoline-3-carbonitrile |
| 138 | 6,7-Difluoro-2-[((S)-1-{1-[5-(4-fluoro-phenyl)-2-methyl-thiazol-4-yl]-methanoyl}-piperidin-2-ylmethyl)-amino]-quinoline-3-carbonitrile |
| 139 | 6,7-Difluoro-2-{[(S)-1-(1-naphthalen-2-yl-methanoyl)-piperidin-2-ylmethyl]-amino}-quinoline-3-carbonitrile |
| 140 | 6,7-Difluoro-2-[((S)-1-{1-[4-(4-fluoro-phenyl)-1H-pyrazol-3-yl]-methanoyl}-piperidin-2-ylmethyl)-amino]-quinoline-3-carbonitrile |
| 141 | 6,7-Difluoro-2-{[(S)-1-(1-1H-indol-6-yl-methanoyl)-piperidin-2-ylmethyl]-amino}-quinoline-3-carbonitrile |
| 142 | 2-{[(S)-1-(1-Benzothiazol-6-yl-methanoyl)-piperidin-2-ylmethyl]-amino}-6,7-difluoro-quinoline-3-carbonitrile |
| 143 | 1-{(S)-2-[(6,7-Difluoro-quinoxalin-2-ylamino)-methyl]-piperidin-1-yl}-1-naphthalen-2-yl-methanone |
| 144 | 1-{(S)-2-[(6,7-Difluoro-quinoxalin-2-ylamino)-methyl]-piperidin-1-yl)}-1-(6-fluoro-benzofuran-2-yl)-methanone |
| 145 | 1-{(S)-2-[(6,7-Difluoro-quinoxalin-2-ylamino)-methyl]-piperidin-1-yl}-1-(5-fluoro-benzofuran-2-yl)-methanone |
| 146 | 1-{(S)-2-[(6,7-Difluoro-quinoxalin-2-ylamino)-methyl]-piperidin-1-yl}-1-(7-fluoro-benzofuran-2-yl)-methanone |
| 147 | 1-(5,7-Difluoro-benzofuran-2-yl)-1-{(S)-2-[(6,7-difluoro-quinoxalin-2-ylamino)-methyl]-piperidin-1-yl}-methanone |
| 148 | 2-[((S)-1-{1-[4-(4-Fluoro-phenyl)-1H-pyrazol-3-yl]-methanoyl}-piperidin-2-ylmethyl)-amino]-nicotinonitrile |
| 149 | 2-[((S)-1-{1-[4-(4-Fluoro-phenyl)-1-methyl-1H-pyrazol-3-yl]-methanoyl}-piperidin-2-ylmethyl)-amino]-nicotinonitrile |
| 150 | 2-[((S)-1-{1-[4-(4-Fluoro-phenyl)-1-methyl-1H-pyrazol-3-yl]-methanoyl}-piperidin-2-ylmethyl)-amino]-isonicotinonitrile |
| 151 | 1-{(S)-2-[(5-Bromo-pyrimidin-2-ylamino)-methyl]-piperidin-1-yl}-1-{2-[3-(3-dimethylamino-propoxy)-phenyl]-thiophen-3-yl}-methanone |
| 152 | 1-{2-[(6,7-Difluoro-quinoxalin-2-ylamino)-methyl]-piperidin-1-yl}-1-{2-[3-(3-dimethylamino-propoxy)-phenyl]-thiophen-3-yl}-methanone |
| 153 | 1-{2-[(6,7-Difluoro-quinoxalin-2-ylamino)-methyl]-piperidin-1-yl}-1-quinolin-8-yl-methanone |
| 154 | 1-{(S)-2-[(6,7-Difluoro-quinoxalin-2-ylamino)-methyl]-piperidin-1-yl)}-1-(1-methyl-1H-indol-2-yl)-methanone |
| 155 | 1-{(S)-2-[(6,7-Difluoro-quinoxalin-2-ylamino)-methyl]-piperidin-1-yl}-1-(1H-indol-6-yl)-methanone |
| 156 | 1-Benzo[1,2,3]thiadiazol-5-yl-1-{(S)-2-[(6,7-difluoro-quinoxalin-2-ylamino)-methyl]-piperidin-1-yl}-methanone |
| 157 | 3-(1-{(S)-2-[(6,7-Difluoro-quinoxalin-2-ylamino)-methyl]-piperidin-1-yl}-methanoyl)-benzoic acid methyl ester |
| 158 | 1-{(S)-2-[(6,7-Difluoro-quinoxalin-2-ylamino)-methyl]-piperidin-1-yl}-1-[1-(2-dimethylamino-ethyl)-4-(4-fluoro-phenyl)-1H-pyrazol-3-yl]-methanone |
| 159 | 1-{(S)-2-[(5-Bromo-pyrimidin-2-ylamino)-methyl]-piperidin-1-yl}-1-[1-(2-dimethylamino-ethyl)-4-(4-fluoro-phenyl)-1H-pyrazol-3-yl]-methanone |
| 160 | 1-[4-(4-Fluoro-phenyl)-1-(2-methoxy-ethyl)-1H-pyrazol-3-yl]-1-[(S)-2-(pyrido[2,3-b]pyrazin-2-ylaminomethyl)-piperidin-1-yl]-methanone |
| 162 | 1-(1H-Benzoimidazol-5-yl)-1-{(S)-2-[(5-bromo-pyrimidin-2-ylamino)-methyl]-piperidin-1-yl}-methanone |
| 163 | 1-Benzofuran-2-yl-1-{(S)-2-[(5-bromo-pyrimidin-2-ylamino)-methyl]-piperidin-1-yl}-methanone |
| 164 | 1-{(S)-2-[(5-Bromo-pyrimidin-2-ylamino)-methyl]-piperidin-1-yl}-1-(2-methoxy-phenyl)-methanone |
| 165 | 1-{(S)-2-[(5-Bromo-pyrimidin-2-ylamino)-methyl]-piperidin-1-yl}-1-quinolin-4-yl-methanone |
| 166 | 1-{(S)-2-[(6,7-Difluoro-quinoxalin-2-ylamino)-methyl]-piperidin-1-yl}-1-[3-(3-dimethylamino-propoxy)-phenyl]-methanone |
| 170 | 1-{(S)-2-[(5-Bromo-pyrimidin-2-ylamino)-methyl]-piperidin-1-yl}-1-[4-(4-fluoro-phenyl)-1-methyl-1H-pyrazol-3-yl]-methanone |
| 119 | 1-{(S)-2-[(6,7-Difluoro-quinoxalin-2-ylamino)-methyl]-pyrrolidin-1-yl}-1-[1-ethyl-4-(4-fluoro-phenyl)-1H-pyrazol-3-yl]-methanone |
| 120 | 1-{(S)-2-[(6,7-Difluoro-quinoxalin-2-ylamino)-methyl]-pyrrolidin-1-yl}-1-[5-(4-fluoro-phenyl)-2H-[1,2,3]triazol-4-yl]-methanone |
| 167 | 1-{(S)-2-[(5-Bromo-pyrimidin-2-ylamino)-methyl]-pyrrolidin-1-yl}-1-[4-(4-fluoro-phenyl)-1-methyl-1H-pyrazol-3-yl]-methanone |

-continued

| Example | Compound Name |
|---|---|
| 168 | 1-{(S)-2-[(6,7-Difluoro-quinoxalin-2-ylamino)-methyl]-pyrrolidin-1-yl}-1-[5-(2-fluoro-phenyl)-thiazol-4-yl]-methanone |
| 169 | 1-{(S)-2-[(6,7-Difluoro-quinoxalin-2-ylamino)-methyl]-pyrrolidin-1-yl}-1-[4-(4-fluoro-phenyl)-1-methyl-1H-pyrazol-3-yl]-methanone |
| 171 | 1-{2-[((S)-1-{1-[4-(4-Fluoro-phenyl)-1-methyl-1H-pyrazol-3-yl]-methanoyl}-piperidin-2-ylmethyl)-amino]-pyrimidin-5-yl}-ethanone |
| 172 | 1-[4-(4-Fluoro-phenyl)-1-methyl-1H-pyrazol-3-yl]-1-((S)-2-{[5-(1-hydroxy-ethyl)-pyrimidin-2-ylamino]-methyl}-piperidin-1-yl)-methanone |
| 173 | 2-[((S)-1-{1-[4-(4-Fluoro-phenyl)-1-methyl-1H-pyrazol-3-yl]-methanoyl}-piperidin-2-ylmethyl)-amino]-pyrimidine-5-carbonitrile |
| 174 | 3-(1-{(S)-2-[(6,7-Difluoro-quinoxalin-2-ylamino)-methyl]-piperidin-1-yl}-methanoyl)-N-methyl-benzamide | and pharmaceutically acceptable salts thereof.

Further compounds of formula (I) are selected from:

| Example | Compound Name |
|---|---|
| 175 | 1-{(S)-2-[(5-Bromo-pyrimidin-2-ylamino)-methyl]-piperidin-1-yl}-1-phenyl-methanone |
| 176 | 1-{(S)-2-[(5-Bromo-pyrimidin-2-ylamino)-methyl]-pyrrolidin-1-yl}-1-[5-(4-fluoro-phenyl)-2-hydroxymethyl-thiazol-4-yl]-methanone |
| 177 | 1-{(S)-2-[(5-Bromo-pyrimidin-2-ylamino)-methyl]-pyrrolidin-1-yl}-1-[4-(4-fluoro-phenyl)-1H-pyrazol-3-yl]-methanone |
| 178 | 1-{(S)-2-[(5-Bromo-pyrimidin-2-ylamino)-methyl]-pyrrolidin-1-yl}-1-quinolin-8-yl-methanone |
| 179 | 1-{(S)-2-[(5-Bromo-pyrimidin-2-ylamino)-methyl]-pyrrolidin-1-yl}-1-(2-ethoxy-phenyl)-methanone |
| 180 | 1-{(S)-2-[(5-Bromo-pyrimidin-2-ylamino)-methyl]-pyrrolidin-1-yl}-1-(2-methyl-5-phenyl-thiazol-4-yl)-methanone |
| 181 | 1-{(S)-2-[(5-Bromo-pyrimidin-2-ylamino)-methyl]-pyrrolidin-1-yl}-1-{5-[3-(3-dimethylamino-propoxy)-phenyl]-2-methyl-thiazol-4-yl}-methanone |
| 182 | 1-{(S)-2-[(5-Bromo-pyrimidin-2-ylamino)-methyl]-pyrrolidin-1-yl}-1-(2-propoxy-phenyl)-methanone |
| 183 | 1-{(S)-2-[(5-Bromo-pyrimidin-2-ylamino)-methyl]-pyrrolidin-1-yl}-1-(2-isopropoxy-phenyl)-methanone |
| 184 | 1-(2-Benzyloxy-phenyl)-1-{(S)-2-[(5-bromo-pyrimidin-2-ylamino)-methyl]-pyrrolidin-1-yl}-methanone |
| 185 | 1-[3-(1-{(S)-2-[(5-Bromo-pyrimidin-2-ylamino)-methyl]-pyrrolidin-1-yl}-methanoyl)-4-ethoxy-phenyl]-ethanone |
| 186 | 1-{(S)-2-[(5-Bromo-pyrimidin-2-ylamino)-methyl]-pyrrolidin-1-yl}-1-(2-ethoxy-6-methoxy-phenyl)-methanone |
| 187 | 1-{(S)-2-[(5-Bromo-pyrimidin-2-ylamino)-methyl]-pyrrolidin-1-yl}-1-(2-ethoxy-6-methyl-phenyl)-methanone |
| 188 | 1-{(S)-2-[(5-Bromo-pyrimidin-2-ylamino)-methyl]-pyrrolidin-1-yl)}-1-(2-ethoxy-naphthalen-1-yl)-methanone |
| 189 | 1-{(S)-2-[(5-Bromo-pyrimidin-2-ylamino)-methyl]-pyrrolidin-1-yl}-1-[5-(2-fluoro-phenyl)-2-methyl-thiazol-4-yl]-methanone |
| 190 | 1-{(S)-2-[(5-Bromo-pyrimidin-2-ylamino)-methyl]-pyrrolidin-1-yl}-1-[5-(3-fluoro-phenyl)-2-methyl-thiazol-4-yl]-methanone |
| 191 | 1-{(S)-2-[(5-Bromo-pyrimidin-2-ylamino)-methyl]-pyrrolidin-1-yl}-1-[5-(2-fluoro-phenyl)-thiazol-4-yl]-methanone |
| 192 | 1-{(S)-2-[(5-Bromo-pyrimidin-2-ylamino)-methyl]-pyrrolidin-1-yl}-1-(5-phenyl-thiazol-4-yl)-methanone |
| 193 | 1-{(S)-2-[(5-Bromo-pyrimidin-2-ylamino)-methyl]-pyrrolidin-1-yl}-1-(2-methyl-4-phenyl-thiazol-5-yl)-methanone |
| 194 | 1-{(S)-2-[(5-Bromo-pyrimidin-2-ylamino)-methyl]-pyrrolidin-1-yl}-1-[5-(4-fluoro-phenyl)-2-methyl-thiazol-4-yl]-methanone |
| 195 | 1-{(S)-2-[(5-Bromo-pyrimidin-2-ylamino)-methyl]-pyrrolidin-1-yl}-1-[2-(3-methyl-[1,2,4]oxadiazol-5-yl)-phenyl]-methanone |
| 196 | 1-{(S)-2-[(5-Bromo-pyrimidin-2-ylamino)-methyl]-pyrrolidin-1-yl}-1-[5-(4-chloro-phenyl)-2-methyl-thiazol-4-yl]-methanone |
| 197 | 1-{(S)-2-[(5-Bromo-pyridin-2-ylamino)-methyl]-pyrrolidin-1-yl}-1-[5-(4-fluoro-phenyl)-2-methyl-thiazol-4-yl]-methanone |
| 198 | 1-{(S)-2-[(5-Bromo-pyridin-2-ylamino)-methyl]-pyrrolidin-1-yl}-1-[4-(4-fluoro-phenyl)-1-methyl-1H-pyrazol-3-yl]-methanone |
| 199 | 1-[3-(Benzooxazol-2-ylaminomethyl)-morpholin-4-yl]-1-[2-(3-methyl-[1,2,4]oxadiazol-5-yl)-phenyl]-methanone |
| 200 | 1-{3-[(5-Bromo-pyrimidin-2-ylamino)-methyl]-morpholin-4-yl}-1-[4-(4-fluoro-phenyl)-1-methyl-1H-pyrazol-3-yl]-methanone |

-continued

| Example | Compound Name |
|---|---|
| 201 | 1-{(S)-2-[(5-Bromo-pyrimidin-2-ylamino)-methyl]-pyrrolidin-1-yl}-1-[5-(3-fluoro-phenyl)-thiazol-4-yl]-methanone |
| 202 | 1-{(S)-2-[(5-Bromo-pyrimidin-2-ylamino)-methyl]-pyrrolidin-1-yl}-1-[5-(4-methoxy-phenyl)-2-methyl-thiazol-4-yl]-methanone |
| 203 | 3,5-Difluoro-4-[((S)-1-{1-[5-(4-fluoro-phenyl)-2-methyl-thiazol-4-yl]-methanoyl}-piperidin-2-ylmethyl)-amino]-benzonitrile |
| 204 | 3,5-Difluoro-4-[((S)-1-{1-[4-(4-fluoro-phenyl)-1-methyl-1H-pyrazol-3-yl]-methanoyl}-piperidin-2-ylmethyl)-amino]-benzonitrile |
| 205 | 3,5-Difluoro-4-[((S)-1-{1-[4-(4-fluoro-phenyl)-1H-pyrazol-3-yl]-methanoyl}-piperidin-2-ylmethyl)-amino]-benzonitrile |
| 206 | 3,5-Difluoro-4-[((S)-1-{1-[2-(3-methyl-[1,2,4]oxadiazol-5-yl)-phenyl]-methanoyl}-piperidin-2-ylmethyl)-amino]-benzonitrile |
| 207 | 4-{[(S)-1-(1-Benzofuran-7-yl-methanoyl)-piperidin-2-ylmethyl]-amine}-3,5-difluoro-benzonitrile |
| 208 | 3,5-Difluoro-4-[((S)-1-{1-[5-(4-fluoro-phenyl)-2-methyl-thiazol-4-yl]-methanoyl}-pyrrolidin-2-ylmethyl)-amino]-benzonitrile |
| 209 | 1-{(S)-2-[(5-Bromo-pyrimidin-2-ylamino)-methyl]-pyrrolidin-1-yl}-1-[2-dimethylamino-5-(4-fluoro-phenyl)-thiazol-4-yl]-methanone |
| 210 | 1-(2-Amino-5-phenyl-thiazol-4-yl)-1-{(S)-2-[(5-bromo-pyrimidin-2-ylamino)-methyl]-pyrrolidin-1-yl}-methanone |
| 211 | 1-{(S)-2-[(5-Bromo-pyrimidin-2-ylamino)-methyl]-pyrrolidin-1-yl}-1-[5-(3-methoxy-phenyl)-2-methyl-thiazol-4-yl]-methanone |
| 212 | 1-{(S)-2-[(5-Bromo-pyrimidin-2-ylamino)-methyl]-pyrrolidin-1-yl}-1-[2-(4-fluoro-phenyl)-thiophen-3-yl]-methanone |
| 213 | 1-{(S)-2-[(5-Bromo-pyrimidin-2-ylamino)-methyl]-pyrrolidin-1-yl}-1-(2-pyridin-2-yl-phenyl)-methanone |
| 214 | 1-{(S)-2-[(5-Bromo-pyrimidin-2-ylamino)-methyl]-pyrrolidin-1-yl}-1-[4-fluoro-2-(3-methyl-[1,2,4]oxadiazol-5-yl)-phenyl]-methanone |
| 215 | 1-{(S)-2-[(5-Bromo-pyrimidin-2-ylamino)-methyl]-pyrrolidin-1-yl}-1-[2-(4-methoxy-phenyl)-thiophen-3-yl]-methanone |
| 216 | 1-{(S)-2-[(5-Ethyl-pyrimidin-2-ylamino)-methyl]-pyrrolidin-1-yl}-1-[5-(4-fluoro-phenyl)-2-methyl-thiazol-4-yl]-methanone |
| 217 | 1-((S)-2-{[(5-Bromo-pyrimidin-2-yl)-methyl-amino]-methyl}-pyrrolidin-1-yl)-1-[5-(4-fluoro-phenyl)-2-methyl-thiazol-4-yl]-methanone |
| 218 | 1-((S)-2-{[(5-Bromo-pyrimidin-2-yl)-methyl-amino]-methyl}-pyrrolidin-1-yl)-1-[4-(4-fluoro-phenyl)-1-methyl-1H-pyrazol-3-yl]-methanone |
| 219 | 1-{(S)-2-[(5-Bromo-pyrimidin-2-ylamino)-methyl]-pyrrolidin-1-yl}-1-[5-(4-fluoro-phenyl)-2-methoxy-thiazol-4-yl]-methanone |
| 220 | 1-{(S)-2-[(5-Bromo-pyrimidin-2-ylamino)-methyl]-pyrrolidin-1-yl}-1-[5-fluoro-2-(3-methyl-[1,2,4]oxadiazol-5-yl)-phenyl]-methanone |
| 221 | 1-{(S)-2-[(5-Bromo-pyrimidin-2-ylamino)-methyl]-pyrrolidin-1-yl}-1-(2-phenyl-thiophen-3-yl)-methanone |
| 222 | 2'-(1-{(S)-2-[(5-Bromo-pyrimidin-2-ylamino)methyl]-pyrrolidin-1-yl}-methanoyl)-biphenyl-4-carbonitrile |
| 223 | 1-{(S)-2-[(5-Bromo-pyrimidin-2-ylamino)-methyl]-pyrrolidin-1-yl}-1-[2-(3-methoxy-phenyl)-thiophen-3-yl]-methanone |
| 224 | 1-{(S)-2-[(5-Bromo-pyrimidin-2-ylamino)-methyl]-pyrrolidin-1-yl}-1-(2-pyrazol-1-yl-phenyl)-methanone |
| 225 | 1-{2-[((S)-1-{1-[5-(4-Chloro-phenyl)-2-methyl-thiazol-4-yl]-methanoyl}-pyrrolidin-2-ylmethyl)-amino]-pyrimidin-5-yl}-ethanone |
| 226 | 1-{(S)-2-[(5-Chloro-pyrimidin-2-ylamino)-methyl]-pyrrolidin-1-yl}-1-[5-(4-fluoro-phenyl)-2-methyl-thiazol-4-yl]-methanone |
| 227 | 1-{(S)-2-[(5-Chloro-pyrimidin-2-ylamino)-methyl]-pyrrolidin-1-yl}-1-[2-(3-methyl-[1,2,4]oxadiazol-5-yl)-phenyl]-methanone |
| 228 | 1-[5-(4-Fluoro-phenyl)-2-methyl-thiazol-4-yl]-1-{(S)-2[(5-methyl-pyrimidin-2-ylamino)-methyl]-pyrrolidin-1-yl}-methanone |
| 229 | 6-[((S)-1-{1-[5-(4-Fluoro-phenyl)-2-methyl-thiazol-4-yl]methanoyl}-pyrrolidin-2-ylmethyl)-amino]-nicotinonitrile |
| 230 | 5-(1-{2-[(5-Bromo-pyrimidin-2-ylamino)-methyl]-piperidin-1-yl}-methanoyl-)4H-benzo[1,4]oxazin-3-one |
| 231 | 1-{(S)-2-[(5-Bromo-pyrimidin-2-ylamino)-methyl]-piperidin-1-yl}-1-[4-(4-fluoro-phenyl)-1-(2-piperidin-1-yl-ethyl)-1H-pyrazol-3-yl]-methanone |
| 232 | 1-{(S)-2-[(5-Bromo-pyrimidin-2-ylamino)-methyl]-pyrrolidin-1-yl}-1-[1-(2-dimethylamino-ethyl)-4-(4-fluoro-phenyl)-1H-pyrazol-3-yl]-methanone |
| 233 | 1-{(S)-2-[(5-Bromo-pyrimidin-2-ylamino)-methyl]-pyrrolidin-1-yl}-1-[2-ethyl-5-(4-fluoro-phenyl)-thiazol-4-yl]-methanone |
| 234 | 1-[5-(4-Fluoro-phenyl)-2-methyl-thiazol-4-yl]-1-{(S)-2-[(6-methyl-2-methylsulfanyl-pyrimidin-4-ylamino)-methyl]-pyrrolidin-1-yl}-methanone |
| 235 | 1-[5-(4-Fluoro-phenyl)-2-methyl-thiazol-4-yl]-1-{(S)-2-[(2-methylsulfanyl-pyrimidin-4-ylamino)-methyl]-pyrrolidin-1-yl}-methanone |
| 236 | 1-{(S)-2-[(Dimethyl-trifluoromethyl-pyrimidin-4-ylamino)-methyl]-pyrrolidin-1-yl}-1-[5-(4-fluoro-phenyl)-2-methyl-thiazol-4-yl]-methanone |
| 237 | 1-{(S)-2-[(2,6-Dimethyl-pyrimidin-4-ylamino)-methyl]-pyrrolidin-1-yl}-1-[5-(4-fluoro-phenyl)-2-methyl-thiazol-4-yl]-methanone |
| 238 | 1-[5-(4-Fluoro-phenyl)-2-methyl-thiazol-4-yl]-1-{(S)-2-[(6-trifluoromethyl-pyrimidin-4-ylamino)-methyl]-pyrrolidin-1-yl}-methanone |

-continued

| Example | Compound Name |
|---|---|
| 239 | 1-(3-{[(5-Bromo-pyrimidin-2-yl)-methyl-amino]-methyl}-morpholin-4-yl)-1-[5-(4-fluoro-phenyl)-2-methyl-thiazol-4-yl]-methanone |
| 240 | 1-(3-{[(5-Bromo-pyrimidin-2-yl)-methyl-amino]-methyl}-morpholin-4-yl)-1-[2-(4-fluoro-phenyl)-thiophen-3-yl]-methanone |
| 241 | 1-{(S)-2-[(5-Bromo-pyrimidin-2-ylamino)-methyl]-piperidin-1-yl}-1-(4-ethyl-quinolin-8-yl)-methanone |
| 242 | 1-{(S)-2-[(5-Bromo-pyrimidin-2-ylamino)-methyl]-piperidin-1-yl}-1-isoquinolin-1-yl-methanone |
| 243 | 1-{(S)-2-[(5-Bromo-pyrimidin-2-ylamino)-methyl]-piperidin-1-yl}-1-(2-methyl-quinolin-5-yl)-methanone |
| 244 | 1-{(S)-2-[(5-Bromo-pyrimidin-2-ylamino)-methyl]-piperidin-1-yl}-1-(3-methyl-quinolin-4-yl)-methanone |
| 245 | 1-{(S)-2-[(5-Bromo-pyrimidin-2-ylamino)-methyl]-piperidin-1-yl}-1-(2,3-dichloro-phenyl)-methanone |
| 246 | 1-{(S)-2-[(5-Bromo-pyrimidin-2-ylamino)-methyl]-piperidin-1-yl}-1-(7-chloro-3-methyl-quinolin-8-yl)-methanone |
| 247 | 1-[5-(4-Chloro-phenyl)-2-methyl-thiazol-4-yl]-1-{(S)-2-[(5-chloro-pyrimidin-2-ylamino)-methyl]-pyrrolidin-1-yl}-methanone |
| 248 | 1-{2-[((S)-1-{1-[2-(3-Methyl-[1,2,4]oxadiazol-5-yl)-phenyl]-methanoyl}-pyrrolidin-2-ylmethyl)-amino]-pyrimidin-5-yl}-ethanone |
| 249 | 1-[5-(4-Fluoro-phenyl)-2-methyl-thiazol-4-yl]-1-{(S)-2-[(5-trifluoromethyl-pyrimidin-2-ylamino)-methyl]-pyrrolidin-1-yl}-methanone |
| 250 | 1-{(S)-2-[(5-Bromo-pyrimidin-2-ylamino)-methyl]-pyrrolidin-1-yl}-1-(4-ethyl-quinolin-8-yl)-methanone |
| 251 | 1-{(S)-2-[(5-Chloro-pyrimidin-2-ylamino)-methyl]-pyrrolidin-1-yl}-1-[2-dimethylamino-5-(4-fluoro-phenyl)-thiazol-4-yl]-methanone |
| 252 | 1-{(S)-2-[(5-Chloro-pyrimidin-2-ylamino)-methyl]-pyrrolidin-1-yl}-1-(2-pyridin-2-yl-phenyl)-methanone |
| 253 | 1-{(S)-2-[(5-Chloro-pyrimidin-2-ylamino)-methyl]-pyrrolidin-1-yl}-1-[2-ethyl-5-(4-fluoro-phenyl)-thiazol-4-yl]-methanone |
| 254 | 1-Biphenyl-2-yl-1-{(S)-2-[(5-chloro-pyrimidin-2-ylamino)-methyl]-pyrrolidin-1-yl}-methanone |
| 255 | 1-{(S)-2-[(5-Bromo-pyrimidin-2-ylamino)-methyl]-pyrrolidin-1-yl}-1-(2,3-dichloro-phenyl)-methanone |
| 256 | 1-{5-[3-(4-Chloro-butoxy)-phenyl]-2-methyl-thiazol-4-yl}-1-{(S)-2-[(5-chloro-pyrimidin-2-ylamino)-methyl]-pyrrolidin-1-yl}-methanone |
| 257 | 1-{(S)-2-[(5-Chloro-pyrimidin-2-ylamino)-methyl]-pyrrolidin-1-yl}-1-[2-(3-isopropyl-[1,2,4]oxadiazol-5-yl)-phenyl]-methanone |
| 258 | 1-{(S)-2-[(5-Bromo-pyrimidin-2-ylamino)-methyl]-pyrrolidin-1-yl}-1-[2-(3-isopropyl-[1,2,4]oxadiazol-5-yl)-phenyl]-methanone |
| 259 | 1-{3-[(5-Bromo-pyridin-2-ylamino)-methyl]-morpholin-4-yl}-1-[2-(4-fluoro-phenyl)-thiophen-3-yl]-methanone |
| 260 | 1-{(S)-2-[(5-Bromo-pyrimidin-2-ylamino)-methyl]-piperidin-1-yl}-1-[2,4-dimethyl-quinolin-8-yl]-methanone |
| 261 | 1-{(S)-2-[(5-Bromo-pyrimidin-2-ylamino)-methyl]-piperidin-1-yl}-1-(2-phenyl-quinolin-4-yl)-methanone |
| 262 | 1-{(S)-2-[(5-Bromo-pyrimidin-2-ylamino)-methyl]-piperidin-1-yl}-1-(2-methyl-quinolin-4-yl)-methanone |
| 263 | 1-{(S)-2-[(5-Bromo-pyrimidin-2-ylamino)-methyl]-piperidin-1-yl}-1-(6-bromo-quinolin-4-yl)-methanone |
| 264 | 1-{(S)-2-[(5-Bromo-pyrimidin-2-ylamino)-methyl]-piperidin-1-yl}-1-(2-methyl-quinolin-8-yl)-methanone |
| 265 | 1-{(S)-2-[(5-Bromo-pyrimidin-2-ylamino)-methyl]-piperidin-1-yl}-1-(8-bromo-quinolin-4-yl)-methanone |
| 266 | 1-{(S)-2-[(5-Bromo-pyrimidin-2-ylamino)-methyl]-piperidin-1-yl}-1-[1-(3-dimethylamino-propyl)-4-(4-fluorophenyl)-1H-pyrazol-3-yl]-methanone |
| 267 | 1-{(S)-2-[(5-Chloro-pyrimidin-2-ylamino)-methyl]-piperidin-1-yl}-1-[1-(2-dimethylamino-ethyl)-4-(4-fluorophenyl)-1H-pyrazol-3-yl]-methanone |
| 268 | 1-{(S)-2-[(5-Chloro-pyrimidin-2-ylamino)-methyl]-piperidin-1-yl}-1-[4-(4-fluoro-phenyl)-1-(2-piperidine-1-yl-ethyl)-1H-pyrazol-3-yl]-methanone |
| 269 | 1-{(S)-2-[(5-Chloro-pyrimidin-2-ylamino)-methyl]-piperidin-1-yl}-1-[4-(4-fluoro-phenyl)-1-(3-piperidine-1-yl-propyl)-1H-pyrazol-3-yl]-methanone |
| 270 | 1-((S)-2-{[(5-Bromo-pyrimidin-2-yl)-methyl-amino]-methyl}-piperidin-1-yl)-1-isoquinolin-1-yl-methanone |
| 271 | 1-((S)-2-{[(5-Bromo-pyrimidin-2-yl)-methyl-amino]-methyl}-piperidin-1-yl)-1-(2,3-dichloro-phenyl)-methanone |
| 272 | 1-{(S)-2-[(5-Chloro-pyrimidin-2-ylamino)-methyl]-piperidin-1-yl}-1-[2-dimethylaminomethyl-5-(4-fluoro-phenyl)-thiazol-4-yl]-methanone |
| 273 | 1-((S)-2-{[(5-Bromo-pyrimidin-2-yl)-methyl-amino]-methyl}-piperidin-1-yl)-1-(3-methyl-quinolin-4-yl)-methanone |
| 274 | 1-((S)-2-{[(5-Bromo-pyrimidin-2-yl)-methyl-amino]-methyl}-piperidin-1-yl)-1-(2-methyl-quinolin-5-yl)-methanone |
| 275 | 1-{(S)-2-[(5-Chloro-pyrimidin-2-ylamino)-methyl]-piperidin-1-yl}-1-[5-(4-fluoro-phenyl)-2-methyl-thiazol-4-yl]-methanone | and pharmaceutically acceptable salts thereof.

Preferred compounds of formula (I) are selected from:

| Example | Compound Name |
| --- | --- |
| 1 | 1-[2-(Benzooxazol-2-ylaminomethyl)-piperidin-1-yl]-1-(2-methyl-5-phenyl-thiazol-4-yl)-methanone |
| 32 | 1-[(S)-2-(Benzooxazol-2-ylaminomethyl)-piperidin-1-yl]-1-[5-(4-fluoro-phenyl)-2-methyl-thiazol-4-yl]-methanone |
| 93 | 1-{2-[(6,7-Difluoro-quinoxalin-2-ylamino)-methyl]-pyrrolidin-1-yl}-1-[4-(4-fluoro-phenyl)-2H-pyrazol-3-yl]-methanone |
| 105 | 1-[2-(3-Methyl-[1,2,4]oxadiazol-5-yl)-phenyl]-1-[(R)-2-(oxazolo[4,5-b]pyridin-2-ylaminomethyl)-piperidin-1-yl]-methanone |
| 106 | 1-[2-(3-Methyl-[1,2,4]oxadiazol-5-yl)-phenyl]-1-{(R)-2-[(methyl-oxazolo[4,5-b]pyridin-2-yl-amino)-methyl]-piperidin-1-yl}-methanone |
| 107 | 6-[(((S)-1-{1-[4-(4-Fluoro-phenyl)-1-methyl-1H-pyrazol-3-yl]-methanoyl}-piperidin-2-ylmethyl)-methyl-amino]-nicotinonitrile |
| 108 | 1-((S)-2-{[(6,7-Difluoro-quinoxalin-2-yl)-methyl-amino]-methyl}-piperidin-1-yl)-1-[4-(4-fluoro-phenyl)-1-methyl-1H-pyrazol-3-yl]-methanone |
| 171 | 1-{2-[(((S)-1-{1-[4-(4-Fluoro-phenyl)-1-methyl-1H-pyrazol-3-yl]-methanoyl}-piperidin-2-ylmethyl)-amino]-pyrimidin-5-yl}-ethanone |
| 172 | 1-[4-(4-Fluoro-phenyl)-1-methyl-1H-pyrazol-3-yl]-1-((S)-2-{[5-(1-hydroxy-ethyl)-pyrimidin-2-ylamino]-methyl}-piperidin-1-yl)-methanone |
| 173 | 2-[((S)-1-{1-[4-(4-Fluoro-phenyl)-1-methyl-1H-pyrazol-3-yl]-methanoyl}-piperidin-2-ylmethyl)-amino]-pyrimidine-5-carbonitrile |
| 174 | 3-(1-{(S)-2-[(6,7-Difluoro-quinoxalin-2-ylamino)-methyl]-piperidin-1-yl}-methanoyl)-N-methyl-benzamide |
| 194 | 1-{(S)-2-[(5-Bromo-pyrimidin-2-ylamino)-methyl]-pyrrolidin-1-yl}-1-[5-(4-fluoro-phenyl)-2-methyl-thiazol-4-yl]-methanone |
| 195 | 1-{(S)-2-[(5-Bromo-pyrimidin-2-ylamino)-methyl]-pyrrolidin-1-yl}-1-[2-(3-methyl-[1,2,4]oxadiazol-5-yl)-phenyl]-methanone |
| 196 | 1-{(S)-2-[(5-Bromo-pyrimidin-2-ylamino)-methyl]-pyrrolidin-1-yl}-1-[5-(4-chloro-phenyl)-2-methyl-thiazol-4-yl]-methanone |
| 197 | 1-{(S)-2-[(5-Bromo-pyridin-2-ylamino)-methyl]-pyrrolidin-1-yl}-1-[5-(4-fluoro-phenyl)-2-methyl-thiazol-4-yl]-methanone |
| 198 | 1-{(S)-2-[(5-Bromo-pyridin-2-ylamino)-methyl]-pyrrolidin-1-yl}-1-[4-(4-fluoro-phenyl)-1-methyl-1H-pyrazol-3-yl]-methanone |
| 200 | 1-{3-[(5-Bromo-pyrimidin-2-ylamino)-methyl]-morpholin-4-yl}-1-[4(4-fluoro-phenyl)-1-methyl-1H-pyrazol-3-yl]-methanone |
| 203 | 3,5-Difluoro-4-[((S)-1-{1-[5-(4-fluoro-phenyl)-2-methyl-thiazol-4-yl]-methanoyl}-piperidin-2-ylmethyl)-amino]-benzonitrile |
| 208 | 3,5-Difluoro-4-[((S)-1-{1-[5-(4-fluoro-phenyl)-2-methyl-thiazol-4-yl]-methanoyl}-pyrrolidin-2-ylmethyl)-amino]-benzonitrile |
| 216 | 1-{(S)-2-[(5-Ethyl-pyrimidin-2-ylamino)-methyl]-pyrrolidin-1-yl}-1-[5-(4-fluoro-phenyl)-2-methyl-thiazol-4-yl]-methanone |
| 217 | 1-((S)-2-{[(5-Bromo-pyrimidin-2-yl)-methyl-amino]-methyl}-pyrrolidin-1-yl)-1-[5-(4-fluoro-phenyl)-2-methyl-thiazol-4-yl]-methanone |
| 218 | 1-((S)-2-{[(5-Bromo-pyrimidin-2-yl)-methyl-amino]-methyl}-pyrrolidin-1-yl)-1-[4-(4-fluoro-phenyl)-1-methyl-1H-pyrazol-3-yl]-methanone |
| 225 | 1-{2-[((S)-1-{1-[5-(4-Chloro-phenyl)-2-methyl-thiazol-4-yl]-methanoyl}-pyrrolidin-2-ylmethyl)-amino]-pyrimidin-5-yl}-ethanone |
| 226 | 1-{(S)-2-[(5-Chloro-pyrimidin-2-ylamino)-methyl]-pyrrolidin-1-yl}-1-[5-(4-fluoro-phenyl)-2-methyl-thiazol-4-yl]-methanone |
| 227 | 1-{(S)-2-[(5-Chloro-pyrimidin-2-ylamino)-methyl]-pyrrolidin-1-yl}-1-[2-(3-methyl-[1,2,4]oxadiazol-5-yl)-phenyl]-methanone |
| 228 | 1-[5-(4-Fluoro-phenyl)-2-methyl-thiazol-4-yl]-1-{(S)-2-[(5-methyl-pyrimidin-2-ylamino)-methyl]-pyrrolidin-1-yl}-methanone |
| 229 | 6-[((S)-1-{1-[5-(4-Fluoro-phenyl)-2-methyl-thiazol-4-yl]-methanyol}-pyrrolidin-2-ylmethyl)-amino]-nicotinonitrile |
| 234 | 1-[5-(4-Fluoro-phenyl)-2-methyl-thiazol-4-yl]-1-{(S)-2-[(6-methyl-2-methylsulfanyl-primidin-4-ylamino)-methyl]-pyrrolidin-1-yl}-methanone |
| 235 | 1-[5-(4-Fluoro-phenyl)-2-methyl-thiazol-4-yl]-1-{(S)-2-[(2-methylsulfanyl-pyrimidin-4-ylamino)-methyl]-pyrrolidin-1-yl}-methanone |
| 239 | 1-(3-{[(5-Bromo-pyrimidin-2-yl)-methyl-amino]-methyl}-morpholin-4-yl)-1-[5-(4-fluoro-phenyl)-2-methyl-thiazol-4-yl]-methanone |
| 240 | 1-(3-{[(5-Bromo-pyrimidin-2-yl)-methyl-amino]-methyl}-morpholin-4-yl)-1-[2-(4-fluoro-phenyl)-thiophen-3-yl]-methanone |
| 249 | 1-[5-(4-Fluoro-phenyl)-2-methyl-thiazol-4-yl]-1-{(S)-2-[(5-trifluoromethyl-pyrimidin-2-ylamino)-methyl]-pyrrolidin-1-yl}-methanone | and pharmaceutically acceptable salts thereof.

When a halogen atom is present in the compound of formula (I) it may be fluorine, chlorine, bromine or iodine.

When the compound of formula (I) contains an alkyl group, whether alone or forming part of a larger group, e.g. alkoxy or alkylthio, the alkyl group may be straight chain, branched or cyclic, or combinations thereof, it is preferably methyl or ethyl.

When used herein the term aryl means a 5- to 6 membered aromatic ring for example phenyl, or a 7 to 12 membered bicyclic ring system where at least one of the rings is aromatic for example naphthyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diostereoismers, including mixtures thereof The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included within the scope of the invention.

Particular compounds according to the invention include those mentioned in the examples and their pharmaceutically acceptable derivatives.

As used herein "pharmaceutically acceptable derivative" includes any pharmaceutically acceptable salt, ester or salt of such ester of a compound of formula (I) which, upon administration to the recipient is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and derivatives thereof. The following schemes detail some synthetic routes to compounds of the invention.

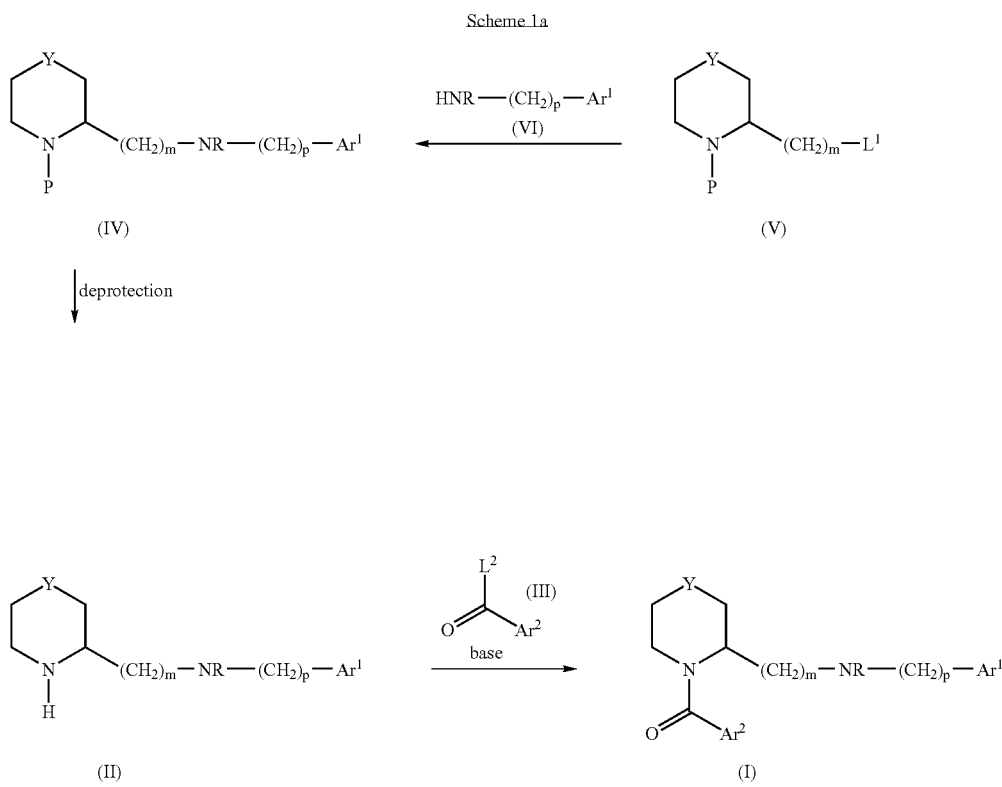

wherein $Ar^1$, $Ar^2$, Y, m, p and R are as defined for formula (I), $L^1$ and $L^2$ are leaving groups, and P is a protecting group.

Examples of suitable leaving groups $L^1$ include halogen, hydroxy, $OSO_2Me$, $OSO_2(4tolyl)$. The reaction of (V) with (VI) preferably proceeds in an inert solvent such as N,N-dimethylformamide in the presence of a base such as triethylamine, sodium hydride or potassium t-butoxide.

Scheme 1b
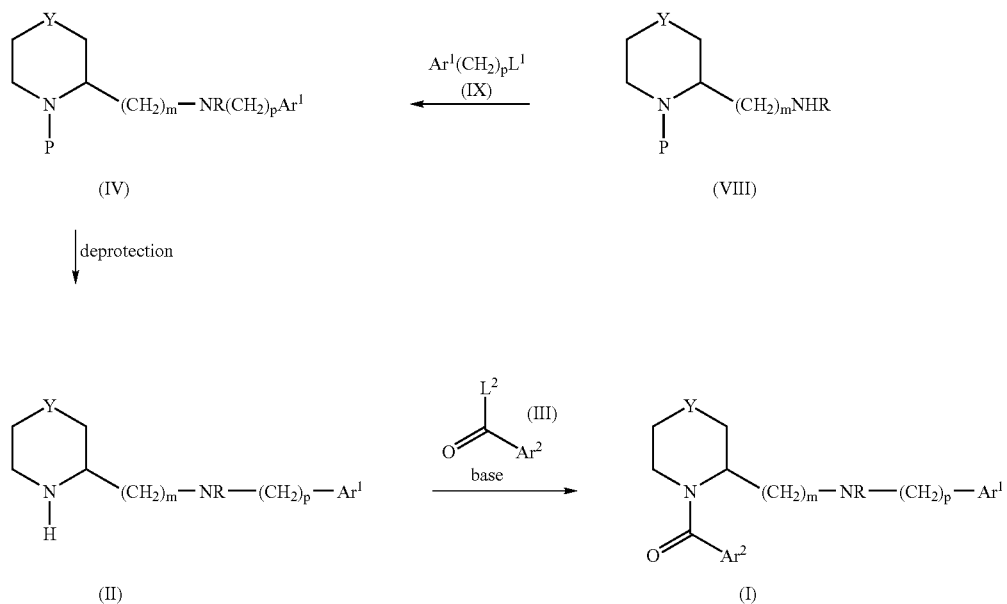
Reaction of (VIII) with (IX) proceeds in an inert solvent such as dimethylformamide or xylene in the presence of a base such as potassium carbonate or diisopropylethylamine, preferably at elevated temperatures.
Alternatively where m is 1 and p is 0 or 1 compounds maybe prepared as shown in scheme 1c.
Scheme 1c
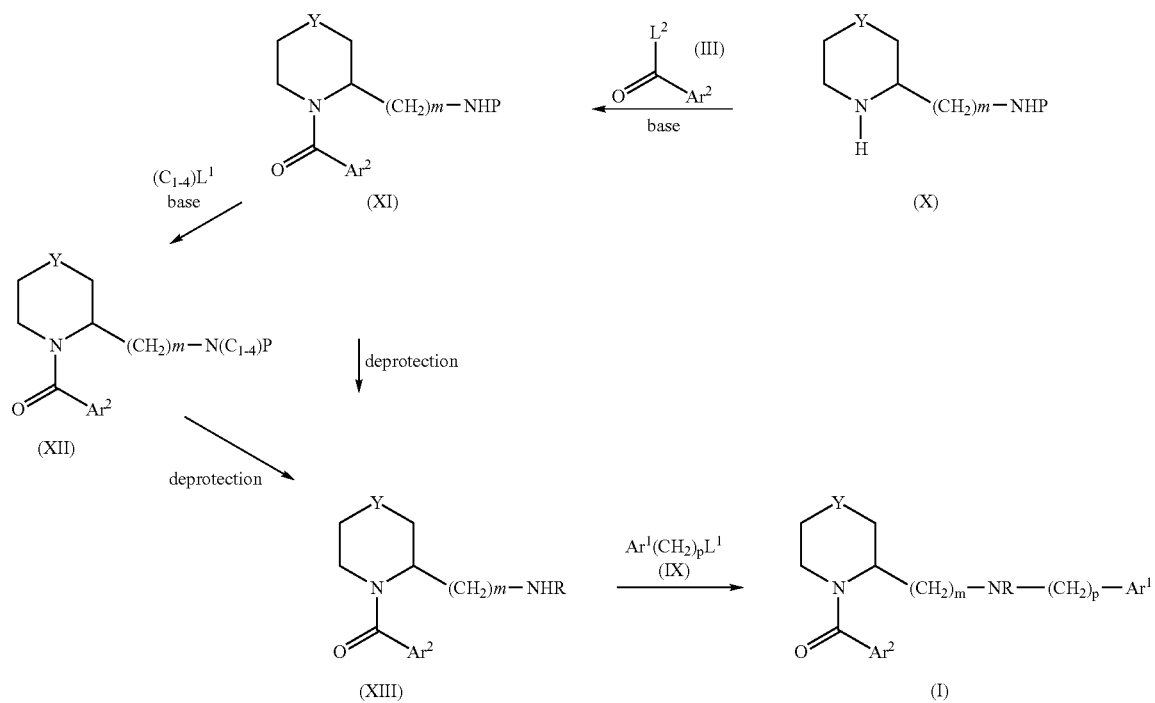

Reaction of (XI) with an alkylating agent $(C_{1-4})L^1$ proceeds in the presence of a base such as sodium hydride in an inert solvent such as dimethylformamide.

Examples of suitable leaving groups $L^2$ include halogen, hydroxy, OC(=O)alkyl and OC(=O)O-alkyl. The transformation (II) to (I) may be carried out in an inert solvent such as dichloromethane, in the presence of a base such as triethylamine. Alternatively this step may be carried out when $L^2$ represents hydroxy, in which case reaction with (II) takes place in an inert solvent such as dichloromethane in the presence of a diimide reagent such as 1-ethyl-3-(3-dimethylaminopropyl)carbodimide hydrochloride, and an activator such as 1-hydroxybenzotriazole.

Examples of protecting groups P include t-butyloxycarbonyl, trifluoroacetyl, optionally substituted benzyl and benzyloxycarbonyl. Deprotection conditions are respectively, acid (e.g. trifluoroacetic acid in dichloromethane), base (e.g. sodium hydroxide in a solvent such as aqueous methanol) and catalytic hydrogenolysis in an inert solvent (e.g using palladium on charcoal in a lower alcohol or ethyl acetate).

Compounds of formula (V), (VI) and (IX) are known in the literature or can be prepared by known methods. Compounds (VIII) can be prepared by known methods.

Within the schemes above there is scope for functional group interconversion; for example in compound (V), conversion of one value of $L^1$ to another value of $L^1$; or in compounds (IV) conversion of protecting group P for another protecting group P, or conversion of one compound of formula (I) to another of formula (I) by interconversion of substituents.

When $R^1$ is an aromatic group, the substituent $R^1$ may be introduced at the final stage as illustrated in Scheme 2 by reaction of a compound of formula (VII) where $L^3$ represents a leaving group such as halogen (preferably bromo or iodo) or trifluoromethylsulfonyloxy, and all other variables are as previously defined, with a reagent $R^1M$, where M is the residue of an organometallic species e.g. $B(OH)_2$ or trialkylstannyl. Such a process may be carried out in an inert solvent such as 1,2-dimethoxyethane or 1,4-dioxan, in the presence of a transition metal catalyst such as $Pd(PPh_3)_4$.

Scheme 2

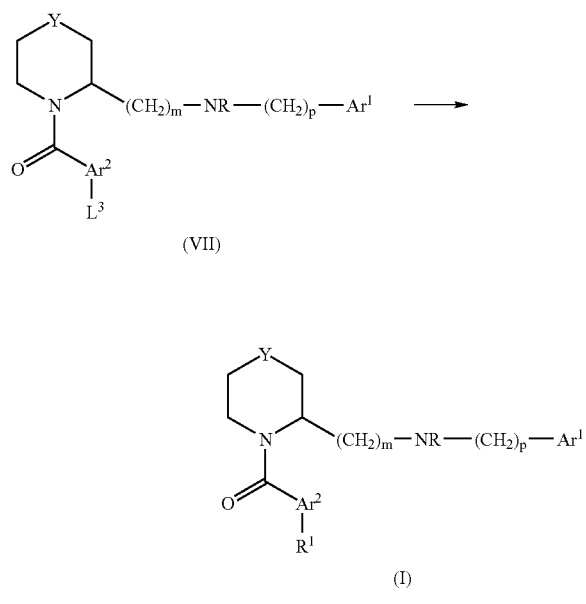

Wherein Y, $Ar^2$, m, p, $Ar^1$, R, $R^1$ and Y are as defined for compounds of formula (I). $L^3$ is a leaving group.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable derivatives thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human Orexin receptor is required such as obesity and diabetes; prolactinoma; hypoprolactinemia; hypothalamic disorders of growth hormone deficiency, idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder, depressive neurosis/disorder; anxiety neurosis; dysthymic disorder, behaviour disorder; mood disorder; sexual dysfunction; psychosexual dysfunction; sex disorder; sexual disorder; schizophrenia; manic depression; delerium; dementia; bulimia and hypopituitarism. Additionally the compounds of formula (I) and pharmaceutically acceptable derivatives are useful for the treatment of stroke, particularly ischemic or haemorrhagic and/or in blocking an emetic response i.e. nausea and vomiting.

The compounds of formula (I) and their pharmaceutically acceptable derivatives are particularly useful for the treatment of obesity, including obesity associated with Type 2 diabetes, and sleep disorders. Additionally the compounds of formula (I) and pharmaceutically acceptable derivatives are useful for the treatment of stroke, particularly ischemic or haemorrhagic and/or in blocking an emetic response i.e. nausea and vomiting.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; bum pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia, and tolerance to narcotics or withdrawal from narcotics.

The invention also provides a method of treating or preventing diseases or disorders where an antagonist of a human Orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human Orexin receptor is required.

The invention also provides the use of a compound of formula (I), or a pharmaceutically acceptable derivative thereof, in the manufacture of a medicament for the treatment or prophylaxis of diseases or disorders where an antagonist of a human Orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical-compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human Orexin-A has the amino acid sequence:

```
pyroGlu Pro Leu Pro Asp Cys Cys Arg Gln Lys Thr
   1             5                      10

Cys Ser Cys Arg Leu Tyr Glu Leu Leu His Gly Ala
            15                  20

Gly Asn His Ala Ala Gly Ile Leu Thr Leu-NH2
    25                  30
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, Drosophila or E. coli. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into Xenopuns oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1-D105 illustrate the preparation of intermediates to compounds of the invention.

In the Examples $^1$H NMR's were measured at 250 MHz in CDCl$_3$ unless otherwise stated.

DESCRIPTION 1

(S) 2-Aminomethyl-piperidine-1-carboxylic acid tert butyl ester a) 2,2,2-Trifluoro-N-[(S)-1-((R)-2-hydroxy-1-phenyl-ethyl)-piperidin-2-ylmethyl]-acetamide (R)-2-[(S)-2-Aminomethyl-piperidin-1-yl])-2-phenyl-ethanol (20.0 g) (Froelich, Olivier; Desos, Patrice; Bonin, Martine; Quirion, Jean-Charles; Husson, Henri-Philippe; Zhu, Jieping., J. Org. Chem. 1996, 61, 6700) and triethylamine (13.0 ml) were dissolved in dichloromethane (500 ml), cooled to 0° C. and trifluoroacetic anhydride (12.66 ml) added dropwise. The mixture was warmed to room temperature and stirred overnight. The organic phase was washed with water, separated, dried and solvent removed at reduced pressure. The residue was column chromatographed [silica gel, 0-10% (9:1 methanol/ammonia) in dichloromethane eluant] to give the title compound (28.0 g) as a yellow oil.

Mass Spectrum (API$^+$): Found 331 (MH$^+$). C$_{16}$H$_{21}$F$_3$N$_2$O$_2$ requires 330. [α]$_D$–55° @ 28° 1% in chloroform b) 2,2,2-Trifluoro-N-(S)-1-piperidia-2ylmethyl-acetamide 2,2,2-Trifluoro-N-[(S)-1-((2-hydroxy-1-phenyl-ethyl)-piperidin-2-ylmethyl]-acetamide (28.0 g) was dissolved in ethanol (200 ml) containing Pearlmans catalyst (2.0 g) and shaken under a hydrogen atmosphere (50 psi) at 50° C. for 3 hours. The reaction mixture was filtered and solvent removed at reduced pressure. The residue was column chromatographed (silica gel, 0-10% (9:1 methanol/ammonia) in dichloromethane eluant) to give the title compound (14.18 g) as a colourless oil.

Mass Spectrum (API$^+$): Found 211 (MH$^+$). C$_8$H$_{13}$F$_3$N$_2$O requires 210. [α]$_D$+18° @ 28° 1% in chloroform $^1$H NMR δ: (d$^6$-DMSO) 1.07 (1H, m), 1.32 (2H, m), 1.35-1.60 (2H, m), 1.72 (1H, m), 2.54 (1H, t), 2.70 (1H, m), 3.00 (1H, d), 3.17 (3H, m), 9.30 (1H, br. s.)

c) (S)2-[(2,2,2-Trifluoro-ethanoylamino)methyl]-piperidine-1-carboxylic acid tert butyl ester 2,2,2-Trifluoro-N-(S)-1-piperidin-2-ylmethyl-acetamide (14.18 g) was dissolved in dichloromethane (250 ml) and treated with di-tert-butyl dicarbonate (14.95 g). The mixture was stirred for 16 h, washed with water, 2N hydrochloric acid and saturated brine, dried and solvent removed at reduced pressure to give the title compound (18.3 g)

Mass Spectrum (API$^+$): Found 311 (MH$^+$). C$_{13}$H$_{21}$F$_3$N$_2$O$_3$ requires 310. [α]$_D$–94° @ 28° 1% in chloroform $^1$H NMR δ: (d$^6$-DMSO) 1.27 (1H, m), 1.36, 1.47 (9H, s), 1.49-1.58 (5H, m), 2.88 (1H, m), 3.22 (1H, m), 3.49 (1H, m), 3.84 (1H, m), 4.34 (1H, m) and 9.42 (1H, br. s.).

d) (S) 2-Aminomethyl-piperidine-1-carboxylic acid tert butyl ester (S)-2-[(2,2,2-Trifluoro-ethanoylamino)-methyl]-piperidine-1-carboxylic acid tert butyl ester (18.2 g) was dissolved in methanol (500 ml) and treated with potassium carbonate (16.1 g). After stirring for 16 h solvent was removed at reduced pressure and the residue partitioned between dichloromethane/water. The organic phase was separated, washed with brine, dried and solvent removed at reduced pressure, the residue was column chromatographed (silica gel, 0-10% (9:1 methanol/ammonia) in dichloromethane eluant) to give the title compound (8.82 g) of description 1.

Mass Spectrum (API$^+$): Found 215 (MH$^+$). C$_{11}$H$_{22}$N$_2$O$_2$ requires 214. [α]$_D$–32.2° @ 28° 1% in chloroform $^1$H NMR δ: 1.44 (2H, m), 1.50 (9H, s), 2.64-2.80 (2H, m), 2.94 (1H, dd), 3.99 (1H, m) and 4.15 (1H, m).

DESCRIPTION 2

(RS) 2-(Benzoxazol-2-ylaminomethyl)-piperidine-1-carboxylic acid tert butyl ester (RS) 2-Aminomethyl-piperidine-1-carboxylic acid tert butyl ester (0.21 g) and 2-chlorobenzoxazole (0.153 g) and triethylamine (0.1 g) were combined in tetrahydrofuran (10 ml) and stirred at room temperature for 4 hours. The mixture was partitioned between ethyl acetate and water, the organic phase dried and solvent removed at reduced pressure to give the title compound (0.36 g) as an oil that solidified on standing.

Mass Spectrum (API$^+$): Found 332 (MH$^+$). C$_{18}$H$_{25}$N$_3$O$_3$ requires 331.

DESCRIPTION 3

(RS) Benzoxazol-2-yl-piperidin-2-ylmethyl-amine

The compound of description 2 (0.36 g) was stirred in trifluoroacetic acid (10 ml) containing water (1 drop) for 3 hours. Solvent was removed at reduced pressure and the residue column chromatographed (silica gel, 0-10% (9:1 methanol/ammonia) in dichloromethane eluant) to give the tide compound (0.23 g).

Mass Spectrum (API$^+$): Found 232 (MH$^+$). C$_{13}$H$_{17}$N$_3$O requires 231.

DESCRIPTION 4

(R)-2-[(S)-2-Benzooxazol-2-ylaminomethyl)-piperidin-1-yl]-2-phenyl-ethanol

A mixture of (R)-2-[(S)-2-Aminomethyl-piperidin-1-yl]) 2-phenyl-ethanol (1.0 g) (Froelich, Olivier; Desos, Patrice; Bonin, Martine; Quirion, Jean-Charles; Husson, Henri-Philippe; Zhu, Jieping. J. Org. Chem. 1996, 61, 6700) and 2-chlorobenzoxazole (0.66 g) were combined in tetrahydrofuran (40 ml) containing triethylamine (0.43 g) and stirred at room temperature for 1 hours. The mixture was partitioned between ethyl acetate and water, the organic phase separated, dried and solvent removed at reduced pressure, the residue was column chromatographed (silica gel, 30% pentane in ethyl acetate-ethyl acetate) to give the title compound (1.1 g).

$^1$H NMR δ: 1.59-1.71 (4H, m), 1.91 (1H, t), 2.73 (1H, m), 2.95 (1H, m), 3.71 (2H, m), 4.0 (1H, m), 4.10 (1H, m), 4.26 (1H, m), 5.7 (1H, m), 7.03 (1H, m), 7.17 (1H, m), 7.23-7.26 (3H, m) and 7.32-7.40 (4H, m). Mass Spectrum (API$^+$): Found 352 (MH$^+$). C$_{21}$H$_{25}$N$_3$O$_2$ requires 351.

DESCRIPTION 5

Benzoxazol-2-yl-(S)-1-piperidin-2-ylmethyl-amine

The compound of description 4 (1.15 g) in ethanol (60 ml) containing Pearlmans catalyst (0.23 g) was shaken under an atmosphere of hydrogen (50 psi) for 24 hours. Additional Pearlmans catalyst was added and shaking under hydrogen at 50 psi continued for a further 12 hours. The reaction was filtered through kiesel guhr, the filtrate evaporated at reduced pressure and the residue column chromatographed (silica gel, ethyl acetate-ethyl acetate/methanol 1:1 eluant) to give the title compound (0.49 g) as an oil.

$^1$H NMR δ: 1.16-1.85 (7H, m), 2.64 (1H, m), 2.85-2.99 (1H, m), 3.11 (1H, m), 3.31 (1H, m), 3.55 (1H, m), 7.00 (1H, dd), 7.12 (1H, m), 7.20 (1H, d) and 7.30 (1H, m). Mass Spectrum (API$^+$): Found 232 (MH$^+$). $C_{13}H_{17}N_3O$ requires 231.

DESCRIPTION 6

(RS)-Benzoxazol-2-yl-(4-benzyl-morpholin-3-ylmethyl)-amine

From (4-benzyl-morpholin-3-yl)-methylamine (1 g) (Morie, Toshiya; Kato, Shiro; Harada, Hiroshi; Yoshida, Naoyuki; Fujiwara, Iwao; Matsumoto, Jun-ichi., Chem. Pharm. Bull. 1995, 43, 1137-47) and 2-chlorobenzoxazole (0.78 g), the title compound (0.77 g) was prepared according to the method of D4.

$^1$H NMR δ: 2.33 (1H, m), 2.73-2.80 (2H, m), 3.33 (1H, d), 3.51-3.90 (6H, m), 4.10 (1H, d), 5.58 (1H, s), 7.04 (1H, m), 7.17 (1H, m) and 7.24-7.39 (7H, m).

Mass Spectrum (API$^+$): Found 324 (MH$^+$). $C_{19}H_{21}N_3O_2$ requires 323.

DESCRIPTION 7

(RS)-Benzoxazol-2-yl-morpholin-3-ylmethyl-amine

From the compound of D6 (0.77 g) the title compound (0.55 g) was prepared according to the method of D5.

$^1$H NMR δ: 2.93-3.23 (2H, m), 3.46-4.03 (7H, m), 6.95-7.23 (4H, m). Mass Spectrum (API$^+$): Found 234 (MH$^+$) $C_{12}H_{15}N_3O_2$ requires 233.

DESCRIPTION 8

(RS) 2-(1H-Benzoimidazol-2-ylaminomethyl)-piperidine-1-carboxylic acid tert butyl ester (RS)-2-Aminomethyl-piperidine-1-carboxylic acid tert butyl ester (0.25 g) and 2-chlorobenzimidazole (0.15 g) were combined and warmed to 100° C. for 48 hours. After cooling to room temperature the mixture was column chromatographed (silica gel, ethyl acetate/pentane 1:4—ethyl acetate/pentane 1:1 eluant) to give the title compound (0.1 g).

$^1$HMR δ: 1.47 (9H, m), 1.65-1.81 (7H, m), 2.85 (1H, t), 3.47 (2H, m), 3.91 (1H, d), 4.32 (1H, s), 5.78 (1H, s), 7.04 (3H, m) and 7.29 (1H, s).

Mass Spectrum (API$^+$): Found 331 (MH$^+$). $C_{18}H_{26}N_4O_2$ requires 330.

DESCRIPTION 9

(RS)-(1H-Benzoimidazol-2-yl)-piperidin-2-ylmethyl-amine dihydrochloride

The compound of D8 (0.39 g) was stirred in a mixture of 4M HCl in dioxan/methanol (1:1) for 4 hours. Solvent was removed at reduced pressure to give the title compound (0.28 g) as a foam.

Mass Spectrum (API$^+$): Found 231 (MH$^+$). $C_{13}H_{18}N_4$ requires 230.

DESCRIPTION 10

(RS) 2-(Quinolin-2-ylaminomethyl)-piperidine-1-carboxylic acid tert butyl ester

The title compound (0.1g) was prepared from (RS) 2-aminomethyl-piperidine-1-carboxylic acid tert butyl ester (0.5 ml) and 2-chloroquinoline (0.5 g) according to the procedure of D8.

Mass Spectrum (API$^+$): Found 342 (MH$^+$). $C_{20}H_{27}N_3O_2$ requires 341.

DESCRIPTION 11

(RS)-Piperidin-2-ylmethyl-quinolin-2-yl-amine

The title compound (0.29 g) was prepared from the compound of D10 according to the method of D9. After removal of solvent the residue was dissolved in dichloromethane, washed with saturated sodium hydrogen carbonate, the organic phase separated, dried and solvent removed at reduced pressure to give the title compound.

$^1$H NMR δ: 1.20-1.96 (6H, m), 2.64 (1H, m), 2.85 (1H, m), 3.10 (1H, m), 3.35 (1H, m), 3.60 (1H, m), 5.17 (1H, m), 6.66 (1H, d), 7.19 (1H, dt), 7.48-7.58 (2H, m), 7.66 (1H, d) and 7.78 (1H, d).

Mass Spectrum (API$^+$): Found 242 (MH$^+$). $C_{15}H_{19}N_3$ requires 241.

DESCRIPTION 12

(RS)-2-(Benzothiazol-2-ylaminomethyl)-piperidine-1-carboxylic acid tert butyl ester The title compound (1.2 g) after column chromatography (silica gel, 5% diethyl ether/hexane-diethyl ether eluant) was prepared from (RS) 2-aminomethyl-piperidine-1-carboxylic acid tert butyl ester (2.0 g) and 2-chlorobenzothiazole (1.58 g) according to the method of D2.

Mass Spectrum (API$^+$): Found 348 (MH$^+$). $C_{18}H_{25}N_3O_2S$ requires 347.

DESCRIPTION 13

(RS)Benzothiazol-2-yl-piperidin-2-ylmethyl-amine

The compound of D12 (1.2 g) was dissolved in methanol (60 ml) and treated with 4N HCl in dioxan (12 ml). the mixture was stirred for 4 h, added to water containing sodium hydrogen carbonate and extracted with ethyl acetate (×3). The combined organic phase was dried and solvent removed at reduced pressure to give the title compound (0.70 g).

Mass Spectrum (API$^+$): Found 348 (MH$^+$). $C_{13}H_{17}N_3S$ requires 347.

DESCRIPTION 14

2-(RS)-(Isoquinolin-1-ylaminomethyl)-piperidine-1-carboxylic acid tert butyl ester The title compound (0.76 g) was prepared from (RS) 2-aminomethyl-piperidine-1-carboxylic acid tert butyl ester (1.6 ml) and 1-chloroisoquinoline (0.8 g) according to the method used for the preparation of the compound of D8.

Mass Spectrum (API$^+$): Found 342 (MH$^+$). $C_{20}H_{27}N_3O_2$ requires 341.

DESCRIPTION 15

Isoquinolin-1-yl-piperidin-2-ylmethyl-amine

The title compound (0.39 g) was prepared according to the method of description 13 from the compound of D14 (0.75 g).

Mass Spectrum (API$^+$): Found 242 (MH$^+$). $C_{15}H_{19}N_3$ requires 241.

DESCRIPTION 16

(S) 2-Quinolin-2-ylaminomethyl)-piperidine-1-carboxylic acid tert butyl ester

The title compound (0.11 g) was prepared from (S) 2-aminomethyl-piperidine-1-carboxylic acid tert butyl ester (1.23 g) and 2-chloroquinoline (1 g) according to the procedure of D8.

Mass Spectrum (API$^+$): Found 342 (MH$^+$). $C_{20}H_{27}N_3O_2$ requires 341.

DESCRIPTION 17

(S)-Piperidin-2-ylmethyl-quinolin-2-yl-amine

The compound of D16 (0.11 g) was dissolved in dichloromethane (10 ml) and trifluoroacetic acid (1 ml) added. The mixture was stirred for 4 h, poured into ice containing potassium carbonate and extracted with 10% methanol/dichloromethane (×3). The combined organic extracts were dried and solvent removed at reduced pressure to give the title compound (0.05 g).

Mass Spectrum (API$^+$): Found 242 (MH$^+$) $C_{15}H_{19}N_3$ requires 241.

DESCRIPTION 18

(RS) 2-(Quinoxalin-2-ylaminomethyl)-piperidine-1-carboxylic acid terf butyl ester The title compound (0.73 g) was prepared from (RS) 2-aminomethyl-piperidine-1-carboxylic acid tert butyl ester (1 ml) and 2-chloroquinoxaline (0.5 g) according to the procedure of D8.

Mass Spectrum (API$^+$): Found 343 (MH$^+$). $C_{19}H_{26}N_4O_2$ requires 342

DESCRIPTION 19

(RS)-Piperidin-2-ylmethyl-quinoxalin-2-yl-amine

The title compound (0.36 g) was prepared from the compound of D18 (0.71 g) according to the method of D17.

Mass Spectrum (API$^+$): Found 243 (MH$^+$). $C_{14}H_{18}N_4$ requires 242.

DESCRIPTION 20

(RS) 2-(Pyrimidin-2-ylaminomethyl)-piperidine-1-carboxylic acid tert butyl ester A mixture of (RS) 2-aminomethyl-piperidine-1-carboxylic acid tert butyl ester (1.28 g) and 2-chloropyrimidine was heated at 100° C. for 48 hours. After cooling to room temperature the mixture was column chromatographed (silica gel, 0-10% (9:1 methanol/ammonia) in dichloromethane eluant) to give the title compound (0.42 g) as an oil.

Mass Spectrum (API$^+$): Found 293 (MH$^+$). $C_{15}H_{24}N_4O_2$ requires 292.

DESCRIPTION 21

(RS)-Piperidin-2-ylmethyl-pyrimidin-2-yl-amine

The title compound (0.350 g) was prepared from the compound of D20 (0.4 g) according to the method of D17.

Mass Spectrum (API$^+$): Found 193 (MH$^+$). $C_{10}H_{16}N_4$ requires 192.

DESCRIPTION 22

(RS) 2-Pyrazin-2-ylaminomethyl)-piperidine-1-carboxylic acid tert butyl ester

The title compound (0.18 g) was prepared from (RS) 2-aminomethyl-piperidine-1-carboxylic acid tert butyl ester (0.54 g) and 2-chloropyrazine according to the method of D20.

Mass Spectrum (API$^+$): Found 293 (MH$^+$). $C_{15}H_{24}N_4O_2$ requires 292.

DESCRIPTION 23

(RS)-Piperidin-2-ylmethyl-pyrazin-2yl-amine

The title compound (0.18 g) was prepared from the compound of D22 (0.08 g) according to the method of D17.

Mass Spectrum (API$^+$): Found 193 (MH$^+$). $C_{10}H_{16}N_4$ requires 192.

DESCRIPTION 24

(S)-2-(Quinazolin-4-ylaminomethyl)-piperidine-1-carboxylic acid tert butyl ester (S)-2-Aminomethyl-piperidine-1-carboxylic acid tert-butyl ester (1.0 g), 4-chloroquinoxaline (0.768 g) and diisopropylethylamine (0.816 ml) were dissolved in tetrahydrofuran (75 ml) and heated to reflux for 6 hours under an atmosphere of argon. After cooling, the reaction solution was partitioned between ethyl acetate and water. The organic layer was washed with saturated sodium hydrogen carbonate solution, saturated brine, dried and evaporated. The residue was chromatographed over silica gel, eluting with a gradient of 50 to 100% ethyl acetate in hexane. The title compound was obtained as a white foam (1.44 g).

$^1$H NMR δ: 1.40 (3H, s), 2.90 (1H, dt), 3.35-3.50 (1H, br.), 3.9-4.05 (1H, br.), 4.15-4.3 (1H, br.), 4.68-4.82 (1H, br.), 6.9-7.2 (1H, br.), 7.40 (1H, t), 7.65-7.85 (3H, m), 8.65(1H, s).

DESCRIPTION 25

(S)-2-(Quinazolin4-ylaminomethyl)-piperidine (S)-2-(Quinazolin4-ylaminomethyl)-piperidine-1-carboxylic acid tert butyl ester (1.2 g) was dissolved in trifluoroacetic acid (60 ml) and stirred at room temperature for 2 hours. The solution was then evaporated and the residue chromatographed over silica gel, eluting with 0 to 10% (9:1 methanol-concentrated ammonia solution) in dichloromethane. The title compound was obtained as a white foam (0.84 g), MH+ 243.

DESCRIPTION 26

(S)-2-[(6,7-Difluoro-3-methylquinoxalin-2-ylamino)methyl]-piperidine-1-carboxylic acid tert buty ester (S)-2-Aminomethyl-piperidine-1-carboxylic acid tert-butyl ester (1.14 g), and 2-chloro-6,7-difluoro-3-methylquinoxaline Teng et al PCT Int. Appl (2000), WO00/42026A1 20000720 (1.14 g) were dissolved in DMF (2 ml) and heated to 90° C. for 3 days under an atmosphere of argon. After cooling, the reaction solution was partitioned between ethyl acetate and water. The organic layer was washed with water, saturated brine, dried and evaporated. The residue was chromatographed over silica gel, eluting with a gradient of 10 to 50% ethyl acetate in hexane. The title compound was obtained as a pink foam (0.524 g), MH+ 393.

DESCRIPTION 27

(S)-2-[(6,7-Difluoro-3-methylquinoxalin-2-ylamino)methyl]-piperidine (S)-2-[(6,7-Difluoro-3-methylquinoxalin-2-ylamino)methyl]-piperidine-1-carboxylic acid tert butyl ester (0.524 g) was dissolved in trifluoroacetic acid (15 ml) and stirred at room temperature for 3 hours. The solution was then evaporated and the residue chromatographed over silica gel, eluting with 0 to 10% (9:1 methanol-concentrated ammonia solution) in dichloromethane. The title compound was obtained as a white solid (0.289 g), MH+ 293.

DESCRIPTION 28

(S)-2-[(6,7-Difluoroquinoxalin-2-ylamino)methyl]-piperidine-1-carboxylic acid tert buty ester (S)-2-Aminomethyl-piperidine-1-carboxylic acid tert-butyl ester (0.607 g), and 2-chloro-6,7-difluoroquinoxaline McQuaid et al. *J. Med Chem.* (1992), 35(18), 3319-24 (0.569 g) were dissolved in dimethylformamide (1 ml) and heated to 90° C. for 5 days under an atmosphere of argon. After cooling, the reaction solution was partitioned between ethyl acetate and water. The organic layer was washed with water, saturated brine, dried and evaporated. The residue was chromatographed over silica gel, eluting with a gradient of 10 to 50% ethyl acetate in hexane. The title compound was obtained as a pale yellow solid (0.460 g), MH+ 379.

DESCRIPTION 29

(S)-2-[(6,7-Difluoroquinoxalin-2-ylamino)methyl]-piperidine (S)-2-[(6,7-Difluoroquinoxalin-2-ylamino)methyl]-piperidine-1-carboxylic acid tert butyl ester (0.460 g) was dissolved in trifluoroacetic acid (10 ml) and stirred at room temperature for 3 hours. The solution was then evaporated and the residue chromatographed over silica gel, eluting with 0 to 10% (9:1 methanol-concentrated ammonia solution) in dichloromethane. The title compound was obtained as a pale yellow foam (0.286 g), MH+ 279.

DESCRIPTION 30

(R,S)-2-[(6,7-Difluoro-quinoxalin-2-ylamino)-methyl]-pyrrolidine-1-carboxylic acid tert butyl ester (R,S)-2-Aminomethyl-pyrrolidine-1-carboxylic acid tert-butyl ester. (3.0 g) and 2-chloro-6,7-difluoroquinoxaline (3.0 g) were combined in xylene (20 ml) containing diisopropylethylamine (3 ml) and heated at 130° C. for 24 hours. Solvent was removed at reduced pressure and the residue column chromatographed (silica gel, diethyl ether:petroleum ether 1:1) to give the title compound (3.4 g)

Mass Spectrum (API+): Found 365 (MH+). $C_{18}H_{22}F_2N_4O_2$ requires 364.

DESCRIPTION 31

(RS)-2-[(6,7-Difluoroquinoxalin-2-ylamino)methyl]-pyrrolidine

The compound of D30 (3.4 g) was dissolved in dichloromethane (100 ml) and treated with trifluoroacetic acid (15 ml). After 3 h additional trifluoroacetic acid (40 ml) and dichloromethane (100 ml) was added. The mixture was stirred for 48 h, poured into excess aqueous sodium hydrogen carbonate, the organic phase separated, dried and solvent removed at reduced pressure. The residue was column chromatographed (silica gel, 5% (9:1 methanol/ammonia)/dichloromethane to give the title compound (0.9 g) Mass Spectrum (API+): Found 265 (MH+). $C_{13}H_{14}F_2N_4$ requires 264. $^1$H NMR δ: 1.56 (1H, m), 1.72-1.93 (3H, m), 2.96 (2h, m), 3.28 (1H, m), 3.49 (1H, m), 3.64 (1H, m), 7.39 (1H, dd), 7.59 1H, dd) and 8.16 (1H, s).

DESCRIPTION 32

(S)-2-(quinazolin-2-ylamino)methyl-piperidine-1-carboxylic acid tert butyl ester The title compound (0.6 g) was prepared from (S)-2-aminomethyl-piperidine-1-carboxylic acid tert-butyl ester (0.68 g) and 2-chloroquinazoline (0.53 g) according to the method of D30.

Mass Spectrum (API+): Found 343 (MH+). $C_{19}H_{26}N_4O_2$ requires 342.

DESCRIPTION 33

(S)-1-Piperidin-2-ylmethyl-quinazolin-2-yl-amine

The title compound (0.384 g) was prepared from the compound of D32 (0.6 g) according to the method of D31

Mass Spectrum (API+): Found 243 (MH+). $C_{14}H_{18}N_4$ requires 242.

$^1$H NMR δ: 1.18-1.65 6H, m), 2.66 (1H, m), 3.08-3.23 (2H, m), 3.50 (1H, m), 3.69 (1H, m), 6.16 (1h, br. s), 7.20 (1H, t), 7.54-7.69 (3H, m) and 8.91 (1H, s).

DESCRIPTION 34

(S)-2-([1,5]Naphthyridin-2-ylaminomethyl)-piperidine-1-carboxylic acid tert butyl ester The title compound (0.48 g) was prepared from (S)-2-aminomethyl-piperidine-1-carboxylic acid tert-butyl ester (0.59 g) and 2-chloro-1,5-naphthyridine Rapoport, et al *J. Org. Chem* (1971), 36(3), 450-4 (0.40 g) according to the method of D30.

Mass Spectrum (API+): Found 343 (MH+). $C_{19}H_{26}N_4O_2$ requires 342.

DESCRIPTION 35

[1,5]Naphthyridin-2-yl-(S)-1-piperidin-2-ylmethyl-amine

The title compound (0.30 g) was prepared from the compound of D34 (0.48 g) according to the method of D31.

Mass Spectrum (API+): Found 243 (MH+). $C_{14}H_{18}N_4$ requires 242. $^1$H NMR δ: 1.25-1.88 (6H, m), 2.68 (1H, m), 2.98 (1H, m), 3.16 (1H, m), 3.37-3.50 (1H, m), 3.66 (1H, m), 6.85 (1H, d), 7.41 1H, dd), 7.95 (1H, t) and 8.58 (1H, m).

DESCRIPTION 36

(S)-2-(1,8-Naphthyridin-2-ylamino)methyl-piperidine-1-carboxylic acid tert butyl ester The title compound (0.28 g) was prepared from (S)-2-aminomethyl-piperidine-1-carboxylic acid tert-butyl ester (0.35 g) and 2-chloro-1,8-naphthyridine (0.19 g) according to the method of D30.

Mass Spectrum (API+): Found 343 (MH+). $C_{19}H_{26}N_4O_2$ requires 342.

DESCRIPTION 37

[1,8]Naphthyridin-2-yl-(S)-1-piperidin-2-ylmethyl-amine

The title compound (0.11 g) was prepared from the compound of D36 (0.28 g) according to the method of D31.

Mass Spectrum (API+): Found 243 (MH+). $C_{14}H_{18}N_4$ requires 242.

DESCRIPTION 38

(RS) 2-(4-Azabenzooxazol-2-ylaminomethyl-piperidine-1-carboxylic acid tert butyl ester The title compound (0.7 g) was prepared from (RS)-2-aminomethyl-piperidine-1-carboxylic acid tert-butyl ester (0.64 g) and 2-methylthio-4-azabenzoxazole Chu-Moyeret al *J. Org Chem.* (1995), 60(17), 5721-5. (0.5 g) according to the method of D30.

Mass Spectrum (API+): Found 333 (MH+). $C_{17}H_{24}N_4O_3$ requires 332.

DESCRIPTION 39

(RS)-Oxazolo[4,5-b]]pyridin-2-yl-piperidin-2-ylmethyl-amine

The title compound (0.55 g) was prepared from the compound of D38 (0.7 g) according to the method of D31.

Mass Spectrum (API+): Found 233 (MH+). $C_{12}H_{16}N_4O$ requires 232.

DESCRIPTION 40

((S)-1-{1-[2-(3-Methyl-[1,2,4]-oxadiazol-5-yl)-phenyl]-methanoyl}-piperidin-2-ylmethyl)-carbamic acid tert butyl ester A mixture of (S)-1-piperidin-2-ylmethyl-carbamic acid tert butyl ester (2.0 g) and 2-(3-methyl-[1,2,4]oxadiazol-5-yl)-benzoic acid (1.9) in dimethylformaide (10 ml containing diisopropylethylamine (2.4 ml) was treated with [O-(7-azabenzotriazol-1-yl)-1,1,3,3-tetramethyluronium hexafluorophosphate] (3.55 g) and stirred at 90° C. for 16 hours. Solvent was removed at reduced pressure and the residue column chromatographed (silica gel, diethyl ether eluant) to give the title compound (3.4 g).

Mass Spectrum (API+): Found 401 (MH+). $C_{21}H_{28}N_4O_4$ requires 400.

DESCRIPTION 41

1-((S)-2-Aminomethyl-piperidin-1-yl)-1-[2-(3-methyl-[1,2,4]oxadiazol-5-yl)-phenyl]-methanone The title compound (0.53 g) was prepared from the compound of D40 according to the method of D13.

Mass Spectrum (API+): Found 301 (MH+). $C_{16}H_{20}N_4O_2$ requires 300.

DESCRIPTION 42

Methyl((S)-1-{1-[2-(3-methyl-[1,2,4]oxadiazol-5-yl)-phenyl]-methanoyl}-piperidin-2-ylmethyl)-carbamic acid dimethyl-ethyl ester ((S)-1-{1-[2-(3-Methyl-[1,2,4]oxadiazol-5-yl)-phenyl]-methanoyl}-piperidin-2-ylmethyl)-carbamic acid tert butyl ester (0.4 g) in tetrahydrofuran (5 ml) was treated with sodium hydride (0.1 g). After evolution of hydrogen had ceased iodomethane (0.1 ml) was added and the reaction stirred for 16 hours. The reaction was quenched with ice/water, extracted with diethyl ether (×3), the combined organic extracts dried and solvent removed at reduced pressure. The residue was column chromatographed (silica gel, diethyl ether) to give the title compound (0.2 g).

Mass Spectrum (API+): Found 415 (MH+). $C_{22}H_{30}N_4O_4$ requires 414.

DESCRIPTION 43

1-[(2-Methylaminomethyl-piperidin-1-yl])-1-[2-(3-methyl-[1,2,4]oxadiazol-5-yl)-phenyl]-methanone The title compound (0.15 g) was prepared from the compound of D42 according to the method of D13.

Mass Spectrum (API+): Found 315 (MH+). $C_{11}H_{12}N_4$ requires 314.

DESCRIPTION 44

(S)-2-[(6,7-Difluoro-quinoxalin-2-ylamino)-methyl]-pyrrolidine-1-carboxylic acid tert butyl ester The title compound (0.53 g) was prepared from (S)2-aminomethyl-pyrrolidine-1-carboxylic acid tert-butyl ester (0.5 g) and 2-chloro-6,7-difluoroquinoxaline (0.5 g) according to the method of D30.

Mass Spectrum (API$^+$): Found 365 (MH$^+$). $C_{18}H_{22}F_2N_4O_2$ requires 364.

DESCRIPTION 45

(S)-2-[(6,7-Difluoroquinoxalin-2-ylamino)methyl]-pyrrolidine

The title compound (0.38 g) was prepared from the compound of D44 (0.53 g) according to the method of D31.

Mass Spectrum (API$^+$): Found 265 (MH$^+$). $C_{13}H_{14}F_2N_4$ requires 264.

DESCRIPTION 46

(RS)-3-[(6,7-Difluoro-quinoxalin-2-ylamino)-methyl]-morpholine-4-carboxylic acid tert butyl ester The title compound (0.58 g) was prepared from 2-aminomethylmorpholine-4carboxylic acid tert-butyl ester (0.82 g) and 2-chloro-6,7-difluoroquinoxaline (0.76 g) according to the method of D30.

Mass Spectrum (API$^+$): Found 381 (MH$^+$). $C_{18}H_{22}F_2N_4O_3$ requires 380.

DESCRIPTION 47

(6,7-Difluoro-quinoxalin-2-yl)-morpholin-3-ylmethyl-amine

The compound of D46 (0.58 g) was dissolved in trifluoroacetic acid and stirred for 3 hours. Solvent was removed at reduced pressure and the residue partitioned between aqueous sodium hydrogen carbonate and ethyl acetate. The organic phase was separated dried, solvent removed at reduced pressure and the residue column chromatographed ( silica gel, 0-10% (9:1 methanol/ammonia) in dichloromethane, eluant ) to give the title compound (0.327 g).

Mass Spectrum (API$^+$): Found 281 (MH$^+$). $C_{13}H_{14}F_2N_4O$ requires 280.

DESCRIPTION 48

2-(Pyrido[2,3-b]pyrazin-2-ylaminomethyl)-piperidine-1-carboxylic acid tert butyl ester and 2-(Pyrido[2,3-b]-pyrazin-3-ylaminomethyl)-piperidine-1-carboxylic acid tert butyl ester A mixture of(S)-2-aminomethyl-piperidine-1-carboxylic acid tert butyl ester (1.0 g) and a 2:1 mixture of 2-chloro-pyrido[2,3-b]pyrazine and 3-chloro-pyrido[2,3-b]pyrazine (0.8 g) was combined and warmed to 90° C. for 18 hours. The mixture was diluted with ethyl acetate, washed with aqueous sodium hydrogen carbonate and water, the organic phase dried and solvent was removed at reduced pressure. The residue was column chromatographed (silica gel, dichloromethane 0 to 6% ethanol in dichloromethane, 1% increments) to give as the faster running component 2-(pyrido[2,3-b]pyrazin-2-ylaminomethyl)-piperidine-1-carboxylic acid tert butyl ester (0.48 g). mass spectrum (API$^+$): Found 344 (MH$^+$). $C_{17}H_{25}N_5O2$ requires 343 and 2-(pyrido[2,3-b]pyrazin-3-ylaminomethyl)-piperidine-1-carboxylic acid tert butyl ester (0.3 g) mass spectrum (API$^+$): Found 344 (MH$^+$). $C_{17}H_{25}N_5O2$ requires 343.

DESCRIPTION 49

Piperidin-2-ylmethyl-pyrido[2,3-b]pyrazin-2-yl-amine trifluoroacetate salt 2 (Pyrido[2,3-b]pyrazin-2-ylaminomethyl)-piperidine-1-carboxylic acid tert butyl ester (0.48 g) was dissolved in dichloromethane (3 ml), cooled (ice bath) and treated with trifluoroacetic acid (2 ml). The mixture was stirred for 3 hours at room temperature, solvent removed at reduced pressure and the residue co-evaporated with toluene to give the title compound (0.45 g).

Mass spectrum (API$^+$): Found 244 (MH$^+$). $C_{13}H_{17}N_5$ requires 243.

DESCRIPTION 50

Piperidin-2-ylmethyl-pyrido[2,3-b]pyrazin-3yl-amine trifluoroacetate salt

The title compound (0.3 g) was prepared from 2-pyrido[2,3-b]pyrazin-3-ylaminomethyl)-piperidine-1-carboxylic acid tert butyl ester (0.3 g) according to the method of description 49

Mass spectrum (API$^+$): Found 244 (MH$^+$). $C_{13}H_{17}N_5$ requires 243.

DESCRIPTION 51

2-Thioureidomethyl-piperidine-1-carboxylic acid tert butyl ester

Benzoyl chloride (1.2 ml) was added dropwise to sodium thiocyanate (0.90 g) in acetone (50 ml). When the addition was complete the mixture was refluxed for 15 minutes, cooled to room temperature and (RS) 2-aminomethyl-piperidine-1-carboxylic acid tert butyl ester (2.0 g) in acetone (5 ml) added. The mixture was refluxed for 2 hours, cooled to room temperature and solvent removed at reduced pressure. The residue was column chromatographed (silica gel, 0-10% (9:1 methanol/ammonia) in dichloromethane eluant) to give the title product (1.95 g).

Mass spectrum (API$^+$): Found 274 (MH$^+$). $C_{12}H_{23}N_3O_2S$ requires 273.

DESCRIPTION 52

2-[(4-Phenyl-thiazol-2-ylamino)-methyl]-piperidine-1-carboxylic acid pert butyl ester The compound of description 51 (1.95 g) was dissolved in ethanol (100 ml) containing triethylamine (0.99 ml). Phenacyl bromide (1.42 g) was added and the mixture stirred for 16 hours. Solvent was removed at reduced pressure and the residue partitioned between ethyl acetate and water. The organic phase was separated and solvent removed at reduced pressure. The residue was column chromatographed (silica gel, dichloromethane eluant) to give the title compound (2.42 g).

Mass spectrum (API+): Found 274 (MH+). $C_{20}H_{27}N_3O_2S$ requires 273.

DESCRIPTION 53

(4-Phenyl-thiazol-2-yl)-piperidin-2-ylmethyl-amine

The tide compound (1.55 g) was prepared from the compound of D52 (2.42 g) according to the method of D47.

Mass spectrum (API+): Found 174 (MH+). $C_{15}H_{19}N_3O_2S$ requires 173.

DESCRIPTION 54

2-[(5-Cyano-pyridin-2-ylamino)methyl]-piperidine-1-carboxylic acid tert butyl ester The title compound (1.54 g) was prepared from (S)-2-aminomethyl-piperidine-1-carboxylic acid tert-butyl ester (2.0 g) and 2-chloro-5-cyanopyridine (1.29 g) in the presence of diisopropylethylamine (1.21 g) according to the method of D28.

Mass spectrum (API+): Found 317 (MH+). $C_{17}H_{24}N_4O_2$ requires 316.

DESCRIPTION 55

6-[(Piperidin-2-ylmethyl)-amino]-nicotinonitrile

The title compound (1.56 g) was prepared from the compound of D54 (1.53 g) and tifluoroacetic acid according to the method of D29.

Mass spectrum (API+): Found 217 (MH+). $C_{12}H_{16}N_4$ requires 216.

DESCRIPTION 56

2-[(4-Trifluoromethyl-pyrimidin-2-ylamino)methyl]-piperidine-1-carboxylic acid tert butyl ester The title compound (0.298 g) was prepared from (S)-2-aminomethyl-piperidine-1-carboxylic acid tert-butyl ester (1.0 g) and 2-chloro-4-trifluoropyrimidine (0.85 g) according to the method of D28.

Mass spectrum (API+): Found 361 (MH+). $C_{16}H_{23}F_3N_4O_2$ requires 360.

DESCRIPTION 57

Piperidin-2-ylmethyl-(4-trifluoromethyl-pyrimidin-2-yl)-amine

The title compound (0.25 g) was prepared from the compound of D56 (0.29 g) and trifluoroacetic acid according to the method of D29.

Mass spectrum (API+): Found 261 (MH+). $C_{11}H_{15}F_3N_4$ requires 260.

DESCRIPTION 58

((S)-1-{1-[4-(4-Fluoro-phenyl)-1-methyl-1H-pyrazol-3-yl]-methanoyl}-piperidin-2-ylmethyl)-carbamic acid pert butyl ester The title compound (3.96 g) was prepared from (S)-1-piperidin-2-ylmethyl-carbamic acid tert butyl ester (2.14 g) and 4-(4-fluoro-phenyl)-1-methyl-1H-pyrazol-3-yl carboxylic acid (2.20 g) according to the method of D40.

Mass spectrum (API+): Found 417 (MH+). $C_{22}H_{29}FN_4O_3$ requires 416.

DESCRIPTION 59

((S)-1-{1-[4-(4-Fluoro-phenyl)-1-methyl-1H-pyrazol-3-yl]-methanoyl}-piperidin-2-ylmethyl)-methyl-carbamic acid dimethyl-ethyl ester.

The title compound (2.0 g) was prepared from the compound of description 58 (3.85 g) according to the method of D42.

Mass spectrum (API+): Found 431 (MH+). $C_{23}H_{31}FN_4O_3$ requires 430

DESCRIPTION 60

1-[4-(4-Fluoro-phenyl)-1-methyl-1H-pyrazol-3-yl]-1-((S)-2-methylaminomethyl-piperidin-1-yl)methanone The title compound (0.5 g) was prepared for the compound of D59 (0.50 g) according to the method of D29.

DESCRIPTION 61

(S)-2-[(3Cyano-pyridin-2-ylamino)methyl]-piperidine-1-carboxylic acid tert butyl ester The title compound (0.66 g) was prepared from (S)-2-aminomethyl-piperidine-1-carboxylic acid tert-butyl ester (1.55 g) and 2-chloro-3-cyanopyridine (1.0 g) according to the method of D28.

Mass spectrum (API+): Found 317 (MH+). $C_{17}H_{24}N_4O_2$ requires 316

DESCRIPTION 62

2-[((S)-1-Piperidin-2-ylmethyl)-amino]-nicotinonitrile

The title compound (0.53 g) was prepared from the compound of D61 (0.663 g) and trifluoroacetic acid according to the method of D29.

Mass spectrum (API+): Found 217 (MH+). $C_{12}H_{16}N_4$ requires 216

DESCRIPTION 63

(S)-2-[(4-Cyano-pyridin-2-ylamino)-methyl]-piperidine-1-carboxylic acid tert butyl ester The title compound (0.24 g) was prepared from (S)-2-aminomethyl-piperidine-1-carboxylic acid tert-butyl ester (1.14 g) and 2-chloro-4-cyanopyridine (0.74 g) according to the method of D28.

Mass spectrum (API+): Found 317 (MH+). $C_{17}H_{24}N_4O_2$ requires 316

DESCRIPTION 64

4-Cyano-2-[((S)-1-Piperidin-2-ylmethyl)-amino]-pyridine

The title compound (0.17 g) was prepared from the compound of D63 (0.243 g) and trifluoroacetic acid according to the method of D29.

Mass spectrum (API$^+$): Found 217 (MH$^+$). $C_{12}H_{16}N_4$ requires 216

DESCRIPTION 65

(S)2-[(5-Bromo-pyrimidin-2-ylamino)-methyl]-piperidine-1-carboxylic acid tert butyl carbonate.

(S)-2-Aminomethyl-piperidine-1-carboxylic acid tert butyl ester (1 g), 5-bromo-2-chloropyrimidine (0.9 g) were combined in xylene (20 ml) containing potassium carbonate (1.29 g) and diisopropylethylamine (2.43 g) and warmed to reflux for 48 h. The mixture was cooled to room temperature, filtered and solvent removed at reduced pressure. The residue was column chromatographed (silica gel, pentane-25% ethyl acetate/pentane). The appropriate fractions were collected, solvent removed at reduced pressure to give the title compound (1.43 g) as a colourless gum Mass spectrum (API$^+$): Found 272 (MH$^+$-tert BOC). $C_{10}H_{14}N_4Br$ requires 371

DESCRIPTION 66

(S) (5-Bromo-pyrimidin-2-yl)-piperidin-2-ylmethyl-amine

The title compound (1.40 g) was prepared from the compound of D65 (2.1 g) according to the method of D9.

Mass spectrum (API$^+$): Found 272 (MH$^+$). $C_{10}H_{14}N_4Br$ requires 271.

DESCRIPTION 67

(S) 2-[(3-Cyano-6,7-difluoro-quinolin-2-ylamino)-methyl]-piperidine-1-carboxylic acid tert butyl ester.

(S)2-Aminomethyl-piperidine-1-carboxylic acid tert-butyl ester (1.1 g) and 2-chloro-3-cyano-5,6difluoroquinoline (1.12 g) according to the method of D28 were combined in xylene (15 ml) containing potassium carbonate (4.0 g) and diisopropylethylamine (4 ml) and boiled for 20 hours. The reaction mixture was cooled to room temperature, filtered and solvent removed at reduced pressure. The residue was column chromatographed (silica gel, dichloromethane eluant) to give after combining appropriate fractions the title compound (1.8 g).

Mass spectrum (API$^+$): Found 403 (MH$^+$). $C_{21}H_{24}F_2N_4O_2$ requires 402

DESCRIPTION 68

(S) 6,7-Difluoro-2-[(piperidin-2-ylmethyl)-amino]-quinoline-3-carbonitrile

The title compound (1.40 g) was prepared from the compound of D67 (1.8 g) according to the method of D9.

Mass spectrum (API$^+$): Found 303 (MH$^+$). $C_{16}H_{16}F_2N_4$ requires 302

DESCRIPTION 69

(S)2-[(5-Bromo-pyrimidin-2-ylamino)-methyl]-pyrrolidin-1-carboxylic acid tert butyl carbonate

(S)-2-Aminomethyl-pyrrolidine-1-carboxylic acid tert butyl ester (2 g), 5-bromo-2-chloropyrimidine (1.93 g) were combined in xylene (40 ml) containing potassium carbonate (2.76 g) and diisopropylethylamine (5.23 ml) and warmed to reflux for 20 h. The mixture was cooled to room temperature, filtered and solvent removed at reduced pressure. The residue was column chromatographed (silica gel, pentane-25% ethyl acetate/pentane). The appropriate fractions were collected, solvent removed at reduced pressure to give the title compound (1.78 g) as a colourless gum Mass spectrum (API$^+$): Found 257 (MH$^+$-tert BOC). $C_{14}H_{21}BrN_4O_2$ requires 357

DESCRIPTION 70

(S) (5-Bromo-pyrimidin-2-yl)-pyrrolidin-2-ylmethyl-amine

The title compound (1.40 g) was prepared from the compound of D69 (1.78 g) according to the method of D9.

Mass spectrum (API$^+$): Found 258 (MH$^+$). $C_9H_{12}N_4Br$ requires 257.

DESCRIPTION 71

3-(1-{(S)-2-[(6,7-Difluoro-quinoxalin-2-ylamino)-methyl]-piperidin-1-yl}-methanoyl)-benzoic acid

3-(1-{(S)-2-[(6,7-Difluoro-quinoxalin-2-ylamino)-methyl]-piperidin-1-yl}-methanoyl)-benzoic acid methyl ester (0.5 g) was dissolved in methanol (15 ml) and treated with 1M sodium hydroxide (1.7 ml). The reaction mixture was stirred for 12 h, additional 1M sodium hydroxide (1.7 ml) added and stirring continued for a further 24 h The reaction mixture was diluted with water and washed with ethyl acetate. The aqueous phase was acidified with 2M hydrochloric acid and extracted with ethyl acetate (×3). the combined organic phase was dried (MgSO$_4$), fioltered and solvent removed at reduced pressure to give the title compound (0.463 g) as a yellow solid.

Mass spectrum (API$^+$): Found 427 (MH$^+$). $C_{22}H_{20}F_2N_4O_3$ requires 426.

DESCRIPTION 72

1,1,1-Trifluoromethanesulphonic acid, 5-bromo-pyridin-2-yl ester

To a solution of 5-bromo-2-pyridone (3 g) in dichloromethane (60 ml) and pyridine (60 ml) at 0° C. under argon was added dropwise trifluoromethane sulphonic anhydride (5.4 g). The resulting mixture was warmed to ambient temperature and after 20 h was evaporated and the residue chromatographed on silica gel eluting with ethyl acetate to afford the title product (3.5 g) as a yellow oil. $^1$H NMR δ: 7.10 (1H, d, J=8 Hz), 8.00 (1H, dd, 2.4 and 8 Hz), 8.46 (1H, d, J=2.4 Hz).

DESCRIPTION 73

(S)-2-[(5-Bromopyridin-2-ylamino)-methyl]-pyrrolidine-1-carboxylic acid tert-butyl ester The title product (0.22 g) was obtained from (S)-2-aminomethyl-pyrrolidine-1-carboxylic acid tert butyl ester (1 g) and the compound of D72 (1.7 g) according to the method of D69. Mass Spectrum (Electrospray LC/MS), API$^+$: Found 356 (MH$^+$). $C_{15}H_{22}{}^{79}BrN_3O_2$ requires 355.

DESCRIPTION 74

(5-Bromo-pyridin-2-yl)-(S)-1-pyrrolidin-2-ylmethylamine

To a solution of the compound from D73 (0.49 g) in dichloromethane (40 ml) at ambient temperature was added trifluoroacetic acid (5 ml). After 48 h, the reaction mixture was evaporated and partitioned between chloroform and 1M sodium hydroxide. The aqueous layer was extracted with chloroform and the combined organic extracts dried and evaporated to afford the tide compound (0.33 g) as an orange oil. $^1$H NMR δ: 1.44-1.48 (1H, m), 1.71-1.81 (3H, m), 2.05 (1H, br s), 2.93 (2H, m), 3.09-3.13 (1H, m), 3.35-3.41 (2H, m), 4.99 (1H, br s), 6.32 (1H, d, J=9 Hz), 7.43 (1H, dd, J=3 and 9 Hz), 8.08 (1H, d, J=3 Hz).

DESCRIPTION 75

N-(4-Benzyl-morpholin-3-ylmethyl)-2,2,2-trifluoroacetamide

To (4-benzyl-morpholin-3-yl)-methylamine (7.34 g) in dichloromediane (240 ml) was added triethylamine (5.83 ml), followed by dropwise addition of trifluoroacetic anhydride (8.23 g) over 25 min at 0° C. under argon. The reaction mixture was allowed to reach ambient temperature and after stirring for 18 h, was diluted in dichloromethane and washed with saturated aqueous sodium hydrogencarbonate. The organic phase was separated, dried and evaporated to afford a brown gum that was purified on silica gel, eluting with ethyl acetate-pentane mixtures to afford the title product (5.17 g) as an orange gum. Mass Spectrum (API$^+$): Found 303 (MH$^+$). $C_{14}H_{17}F_3N_2O_2$ requires 302.

DESCRIPTION 76

2,2,2-Trifluoro-N-morpholin-3-ylmethyl acetamide

To the compound from D75 (1.62 g) in methanol (40 ml) was added palladium black (0.45 g) and formic acid (10 drops) and the mixture stirred at ambient temperature for 16 h. Further palladium black (0.225 g) and formic acid (10 drops) were added and after 1 h, the reaction mixture was filtered through kieselguhr and the filtrate evaporated to an orange gum. Re-evaporation from dichloromethane provided the title compound (1.4 g) as a pink solid. Mass Spectrum (API$^+$): Found 213 (MH$^+$). $C_7H_{11}F_3N_2O_2$ requires 212.

DESCRIPTION 77

3-[(2,2,2-Trifluoro-ethanoylamino)methyl]-morpholine4-carboxylic acid tert-butyl ester A mixture of the compound from D76 (1.75 g), triethylamine (2.25 ml) and di-tert-butyl dicarbonate (3.59 g) in dichloromethane (75 ml) was stirred at ambient temperature for 18 h. The reaction mixture was diluted with dichloromethane and washed successively with 2M hydrochloric acid, water and brine, dried and evaporated to a gum. Chromatography on silica gel eluting with ethyl acetate-pentane mixtures afforded the title compound (1.70 g) as a pale yellow solid. Mass Spectrum (API$^+$): Found 213 (MH-$^t$Boc)$^+$. $C_{12}H_{19}F_3N_2O_4$ requires 312.

DESCRIPTION 78

3-Aminomethyl-morpholine4-carboxylic acid tert-butyl ester

A mixture of the compound from D77 (1.7 g) and potassium carbonate (3.77 g) in methanol (80 ml) and water (27 ml) was stirred at ambient temperature for 4 h and then heated at 50° C. for a further 2 h The reaction mixture was concentrated to remove methanol, diluted with water and extracted with ethyl acetate (×3) and dichloromethane (×4). The combined extracts were dried and evaporated to afford the title product (0.97 g) as a yellow gum. Mass Spectrum (API$^+$): Found 116 (MH-$^t$Boc)$^+$. $C_{10}H_{20}N_2O_3$ requires 216.

DESCRIPTION 79

3-[(5Bromo-pyrimidin-2-ylamino)-methyl]-morpholine4-carboxylic acid tert-butyl ester The title compound (1.19 g) was obtained from the compound of D78 (0.97 g) and 5-bromo-2-chloropyrimidine (0.87 g) according to the method of D30. Mass spectrum (API$^+$): Found 273 (MH$^+$-$^t$Boc). $C_{14}H_{21}{}^{79}BrN_4O_3$ requires 372.

DESCRIPTION 80

(5-Bromo-pyrimidin-2-yl)-morpholin-3-ylmethyl amine

To the compound of D79 (1.15 g) in dichloromethane (45 ml) at 0° C. was added trifluoroacetic acid (5 ml) and the reaction mixture then stirred at ambient temperature for 2 h. The resulting solution was poured onto ice and saturated aqueous potassium carbonate solution, and then extracted with dichloromethane (×2). The organic extracts were dried and evaporated to afford the title product (0.85 g) as an off white solid. Mass Spectrum (API$^+$): Found 273 (MH$^+$). $C_9H_{13}{}^{79}BrN_4O$ requires 272.

DESCRIPTION 81

(S)-2-[(4-Cyano-2,6-difluorophenylamino)-methyl]-piperidine-1-carboxylic acid tert-butyl ester (S)-2-Aminomethyl-piperidine-1-carboxylic acid tert-butyl ester (1.36 g) and 3,4,5-trifluorobenzonitrile (1.00 g) were heated under argon in xylene (10 ml) containing diisopropylethylamine (3.3 ml) for 16 h. The reaction mixture was cooled and partitioned between ethyl acetate and water. The organic phase was washed with brine, dried and evaporated to give a solid which was triturated with pentane-ether to afford the title product (0.16 g) as an off white powder. Chromatography of the mother liquors on silica gel eluting with ethyl acetate-pentane mixtures afforded further title product (0.92 g). Mass Spectrum (API$^+$): Found 252 (MH$^+$-$^t$Boc). $C_{18}H_{23}F_2N_3O_2$ requires 351.

DESCRIPTION 82

3,5-Difluoro4-[((S)-1-piperidin-2-ylmethyl)-amino]-benzonitrile

Trifluoroacetic acid (3 ml) was added to a solution of D81 (1.05 g) in dichloromethane (27 ml) at 0° C. The reaction was allowed to reach ambient temperature, stirred for 4 h and then poured into saturated aqueous potassium carbonate. The aqueous phase was extracted with dichloromethane and the combined extracts dried and evaporated to afford the title compound (0.59 g) as an off white solid. Mass Spectrum (API$^+$): Found 252 (MH$^+$). $C_{13}H_{15}F_2N_3$ requires 251.

DESCRIPTION 83

(S)-2-[(4-Cyano-2,6-difluoro-phenylamino)-methyl]-pyrrolidine-1-carboxylic acid tert-butyl ester The title compound (0.295 g) was obtained from (S)-2-aminomethyl-pyrrolidine-1-carboxylic acid tert-butyl ester (0.402 g) and 3,4,5-trifuorobenzonitrile (0.314 g) using a similar procedure to that described in Description 81. Mass Spectrum (API$^+$): Found 238 (MH$^+$-$^t$Boc) $C_{17}H_{21}F_2N_3O_2$ requires 337.

DESCRIPTION 84

3,5-Difluoro4-[((S)-1-pyrrolidin-2-ylmethyl)-amino]-benzonitrile

The title compound (0.19 g) was obtained from the compound of D83 (0.28 g) using a similar procedure to that described in Description 82.

DESCRIPTION 85

(S)-2-[(5-Ethyl-pyrimidin-2-ylamino)-methyl]-pyrrolidine-1-carboxylic acid tert-butyl ester The title compound (0.10 g) was obtained from (S)2-aminomethyl-pyrrolidine-1-carboxylic acid tert-butyl ester (0.75 g) and 2-chloro-5-ethyl pyrimidine (0.53 g) using a similar procedure to that described in description 81. Mass Spectrum (Electrospray LC/MS): Found 307 (MH$^+$). $C_{16}H_{26}N_4O_2$ requires 306.

DESCRIPTION 86

(5-Ethyl-pyrimidin-2-yl)-(S)-1-pyrrolidin-2-ylmethylamine

The title compound (0.07 g) was obtained from the compound of D85 (0.10 g) using the method of D9. Mass Spectrum (Electrospray LC/MS): Found 207 (MH$^+$). $C_{11}H_{18}N_4$ requires 206.

DESCRIPTION 87

(S)-2-[(2,2,2-Trifluoro-ethanoylamino)-methyl]-pyrrolidine-1-carboxylic acid tert-butyl ester To a solution of (S)-2-aminomethyl pyrrolidine-1-carboxylic acid tert-butyl ester (1.3 g) in dichloromethane (50 ml) containing triethylamine (1.4 ml) was added trifluoroacetic anhydride (1.6 g) dropwise under argon. After 16 h at ambient temperature the reaction mixture was diluted with dichloromethane and washed with brine. The aqueous layer was extracted with dichloromethane and the combined extracts dried and evaporated. Chromatography of the residue on silica gel eluting with pentane-ethyl acetate mixture afforded the title compound (1.43 g) as an orange oil. $^1$H NMR δ: 1.30-1.50 (1H, m), 1.47 (9H, s), 1.60-1.75 (1H, m), 1.80-1.95 (2H, m), 2.00-2.10 (1H, m), 3.22-3.30 (1H, m) 3.30-3.55 (3H, m), 9.03 (1H, br s).

DESCRIPTION 88

(S)-2-{[Methyl-2,2,2-trifluoro-ethanoyl)-amino]-methyl}-pyrrolidine-1-carboxylic acid tert-butyl ester Sodium hydride (0.23 g, 60% dispersion in oil) was added to a solution of the compound of D87 (1.4 g) in dimethylformamide (30 ml) under argon. After 1 h, iodomethane (0.32 ml) was added and the reaction mixture stirred for a firer 16 h before being partitioned between ethyl acetate and water. The aqueous layer was extracted with ethyl acetate and the combined extracts washed with brine, dried and evaporated to give the title compound (1.6 g) as an orange oil. Mass Spectrum (API$^+$): Found 311 (MH$^+$); $C_{13}H_{21}F_3N_2O_3$ requires 310.

DESCRIPTION 89

(S)-2-Methylaminomethyl-pyrrolidine-1-carboxylic acid tert-butyl ester

A mixture of the compound of D88 (1.47 g) and 1M potassium carbonate (20 ml) in methanol (50 ml) was stirred at ambient temperature for 20 h. After removal of the methanol in vacuo, the residue was partitioned between chloroform and water. The aqueous layer was extracted with chloroform and the combined extracts dried and evaporated to afford the title product (0.82 g) as an orange oil.

DESCRIPTION 90

(S)-2-{[(5-Bromo-pyrimidin-2-yl)-methyl-amino]-methyl}-pyrrolidine-1-carboxylic acid tert-butyl ester The title product (0.85 g) was obtained from the compound of D89 (0.82 g) and 5-bromo-2-chloro pyrimidine (0.77 g) in a similar manner to that described in the procedure of description 81. Mass Spectrum (API$^+$): Found 371 (MH$^+$). $C_{15}H_{23}^{79}BrN_4O_2$ requires 370.

DESCRIPTION 91

(5-Bromo-pyrimidin-2-yl)-methyl-(S)-1-pyrrolidin-2-yl)methylamine

A solution of the compound from D90 (0.82 g) in dichloromethane (50 ml) and trifluoroacetic acid (10 ml) was stirred at ambient temperature for 20 h. evaporated and partitioned between ethyl acetate and 1M sodium hydroxide. The organic phase was separated, dried and evaporated to afford the title product as an orange oil (0.54 g). Mass Spectrum (API$^+$): Found 271 (MH$^+$). $C_{10}H_{15}^{79}BrN_4$ requires 270.

DESCRIPTION 92

(S)-2-[(5-Acetyl-pyrimidin-2-ylamino)-methyl]-pyrrolidine-1-carboxylic acid tert-butyl ester The title compound (0.57 g) was prepared from the compound of D69 (1.06 g) (1-ethoxyvinyl)tributyl tin (1.2 ml) and tetrakis (triphenylphosphine)palladium (0) (0.172 g) according to the method of Example 171. Mass Spectrum (API$^+$): Found 321 (MH$^+$). $C_{16}H_{24}N_4O_3$ requires 320.

DESCRIPTION 93

1-{2-[((S)-1-Pyrroldin-2-ylmethyl)amino]-pyrimidin-5yl}-ethanone trifluoroacetate To a solution of the compound of D92 (0.57 g) in dichloromethane (18 ml) at 0° C. was added trifluoroacetic acid (2 ml) dropwise. The reaction mixture was stirred at ambient temperature for 2 h, and evaporated to afford the title compound as a yellow gum (1.13 g).
Mass Spectrum (API$^+$): Found 221 (MH$^+$). $C_{11}H_{16}N_4O$ requires 220.

DESCRIPTION 94

(S)-2-[(5Chloro-pyrimidin-2-ylamino)methyl]-pyrrolidine-1-carboxylic acid tert-butyl ester (S)-2-Aminomethyl pyrrolidine-1-carboxylic acid tert-butyl ester (3.38 g), 2,5-dichloropyrimidine (2.50 g), potassium carbonate (4.67 g) and diisopropylethylamine (8.79 ml) were heated in xylene (60 ml) at 100° C. for 3.75 h. The cooled reaction mixture was filtered and the filtrate evaporated to a gum which was chromatographed on silica gel, eluting with ethyl acetate-pentane fractions, to afford the title compound as a pale yellow solid (2.55 g). Mass Spectrum (API$^+$): Found 213 (MH$^+$-$^t$Boc). $C_{14}H_{21}{}^{35}ClN_4O_2$ requires 312.

DESCRIPTION 95

(5-Chloro-pyrimidin-2-yl)-(S)-1-pyrrolidin-2-ylmethylamine

The compound of D94 (2.5 g) was dissolved in dichloromethane (63 ml), cooled to 0° C. and trifluoroacetic acid (7 ml) added dropwise. The reaction mixture was stirred at ambient temperature for 2 h, recooled to 0° C. and further trifluoroacetic acid (3 ml) added. After 2 h at ambient temperature the mixture was carefully poured into ice-saturated potassium carbonate and the organic layer separated. The aqueous phase was extracted with dichloromethane (×4) and the combined extracts dried and evaporated to afford the title product (1.74 g) as an orange solid. Mass Spectrum (Electrospray LC/MS): Found 213 (MH$^+$). $C_9H_{13}{}^{35}ClN_4$ requires 212.

DESCRIPTION 96

(S)-2-[(5-Cyano-pyridin-2-ylamino)-methyl]-pyrrolidine-1-carboxylic acid tert-butyl ester (S)-2-Aminomethyl pyrrolidine-1-arboxylic acid tert-butyl ester (0.3 g), 6-chloronicotinonitrile (0.21 g), potassium carbonate (0.41 g) and diisopropylethylamine (0.78 ml) were heated in xylene at 130° C. for 26 h, cooled and the mixture filtered through kieselguhr. The filtrate was evaporated and the residue chromatographed on silica gel, eluting with ethyl acetate-hexane mixtures to afford the title compound (0.2 g). Mass Spectrum (API$^+$): Found 303 (MH$^+$). $C_{16}H_{22}N_4O_2$ requires 302.

DESCRIPTION 97: 6-[((S)-1-Pyrrolidin-2-ylmethyl)-amino]-nicotinonitrile

A solution of the compound of D96 (0.2 g) in dichloromethane (20 ml) and trifluoroacetic acid (2.5 ml) was stirred at ambient temperature for 2 h., evaporated and partitioned between dichloromethane and 1M sodium hydroxide. The aqueous phase was extracted with dichloromethane and the combined extracts dried and evaporated to afford the title compound as a gum (0.137 g). Mass Spectrum (Electrospray LC/MS): Found 203 (MH$^+$). $C_{11}H_{14}N_4$ requires 202.

DESCRIPTION 98

1,1,1-Trifluoromethanesulfonic acid 6-methyl-2-methylsulfanyl-pyrimidin-4-yl ester To a solution of 6-methyl-2-methylsulfanyl-pyrimidin-4-ol (1 g) in dichloromethane (40 ml) containing triethylamine (1.35 ml) at 0° C. under argon was added trifluoromethanesulphonic anhydride (1.46 ml) dropwise. The resulting solution was allowed to reach ambient temperature and stirred for 16 h. before being partitioned between dichloromethane and saturated aqueous sodium hydrogen carbonate solution. The organic phase was washed with brine, dried and evaporated and the residue chromatographed on silica gel, eluting with ethyl acetate-pentane mixtures, to afford the title compound (0.8 g). $^1$H NMR δ: 2.53 (3H, s), 2.55 (3H, s), 6.63 (1H, s).

DESCRIPTION 99

2,2,2-Trifluoro-N-(S)-1-pyrrolidin-2-ylmethyl-acetamide

The title compound (2.31 g) was obtained from the compound of D87 (5.5 g) using the method of D97. $^1$H NMR δ: 1.30-1.50 (1H, m), 1.70-1.95 (3H, m), 2.20 (1H, br s), 2.85-2.90 (1H, m), 2.94-2.97 (1H, m), 3.07-3.12 (1H, m), 3.37-3.39 (1H, m), 3.44-3.48 (1H, m), 7.15 (1H, br s).

DESCRIPTION 100

2,2,2-Trifluoro-N-((S)-1-{1-[5-(4-fluorophenyl)-2-methyl-thiazol4-yl]-methanoyl}-pyrrolidin-2-ylmethyl)-acetamide The title compound (3.84 g) was obtained from the compound of D99 (2.31 g) and 5-(4-fluorophenyl)-2-methyl-thiazole-4-carboxylic acid (3.08 g) using the method of Example 229. Mass Spectrum (Electrospray LC/MS): Found 416 (MH$^+$). $C_{18}H_{17}F_4N_3O_2S$ requires 415.

DESCRIPTION 101

1-((S)-2-Aminomethyl-pyrrolidin-1-yl)-1-[5-(4-fluoro-phenyl)-2-methyl-thiazol4-yl]-methanone The title compound (2.45 g) was obtained from the compound of D100 (3.84 g) using a similar procedure to that described in D78. Mass Spectrum (Electrospray LC/MS): Found 320 (MH$^+$). $C_{16}H_{18}FN_3OS$ requires 319.

DESCRIPTION 102

3-[(2,2,2-Trifluoro-ethanoylamino)-methyl]-morpholine-4-carboxylic acid tert-butyl ester The title compound (0.56 g) was obtained from the compound of D77 (0.55 g) and iodomethane (0.12 ml) using a method similar to that of Description 88. Mass Spectrum (API$^+$): Found 227 (MH$^+$-$^t$Boc). $C_{13}H_{21}F_3N_2O_4$ requires 326.

DESCRIPTION 103

3-Methylaminomethyl-morpholine-4-carboxylic acid tert-butyl ester

The title compound (0.29 g) was obtained from the compound of D102 (0.56 g) using the method of Description 89.

DESCRIPTION 104

3-{[(5-Bromo-pyrimidin-2-yl)-methyl-amino]-methyl}-morpholine-4-carboxylic acid tert-butyl ester The title compound (0.3 g) was obtained from the compound of D103 (0.29 g) and 5-bromo-2-chloropyrimidine (0.26 g) using the method of Description 81. Mass Spectrum (Electrospray LC/MS): Found 287 (MH$^+$-$^t$Boc). $C_{15}H_{23}{}^{79}BrN_4O_3$ requires 386.

DESCRIPTION 105

(5-Bromo-pyrimidin-2-yl)-methyl-morpholin-3-ylmethyl-amine

The title compound (0.19 g) was obtained from the compound of D104 (0.3 g) according to the method of Description 91. Mass Spectrum (API$^+$): Found 287 (MH$^+$). $C_{10}H_{15}{}^{79}BrN_4O$ requires 286.

EXAMPLE 1

1-[2-Benzoxazol-2-ylaminomethyl)-piperidin-1-yl]-1-(2-methyl-5phenyl-thiazol4-yl)-methanone The amine of D3 (0.11 g), triethylamine (0.05 g) and 2-methyl-5-phenyl-thiazole4-carbonyl chloride (0.12 g) were combined in dichloromethane (5 ml) and shaken for 16 hours. The organic phase was washed with water, filtered through a Whatman phase-separation filter tube, solvent removed at reduced pressure to give after column chromatography (silica gel, 0-10% (9:1 methanol/ammonia) in dichloromethane eluant) the title compound (0.13 g).

Mass Spectrum (API$^+$): Found 433 (MH$^+$). $C_{24}H_{24}N_4O_2S$ requires 432.

The compounds of the Examples below were prepared from the appropriate amine and acid chloride using a similar procedure to that described in Example. 1.

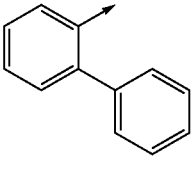

| Example | Amine | Y | Ar$^2$ | Ar$^1$ | Mass Spectrum (Electrospray LC/MS) API$^+$ |
|---|---|---|---|---|---|
| 2 | D3 | CH$_2$ | 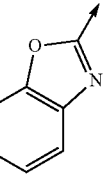 | 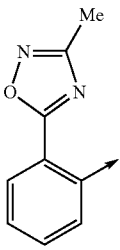 | Found 412 (MH$^+$). $C_{26}H_{25}N_3O_2$ requires 411 |
| 3 | D3 | CH$_2$ | 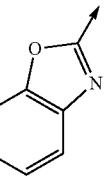 | | Found 418 (MH$^+$). $C_{23}H_{23}N_5O_3$ requires 417 |

-continued
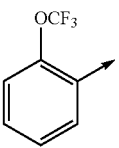
| Example | Amine | Y | Ar² | Ar¹ | Mass Spectrum (Electrospray LC/MS) API⁺ |
|---|---|---|---|---|---|
| 4 | D3 | CH₂ | 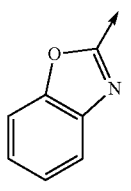 | 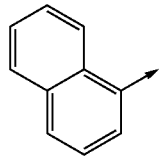 | Found 420 (MH⁺). $C_{21}H_{20}F_3N_3O_3$ requires 419 |
| 5 | D3 | CH₂ | 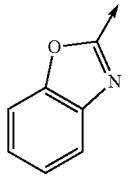 | 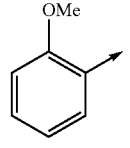 | Found 386 (MH⁺). $C_{24}H_{23}N_3O_2$ requires 385 |
| 6 | D3 | CH₂ | 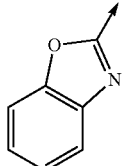 | 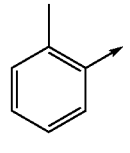 | Found 366 (MH⁺). $C_{21}H_{23}N_3O_3$ requires 365 |
| 7 | D3 | CH₂ | 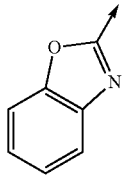 | 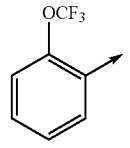 | Found 462 (MH⁺). $C_{20}H_{20}IN_3O_2$ requires 461 |
| 8 | D5 | CH₂ | 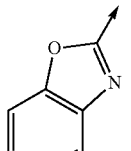 | 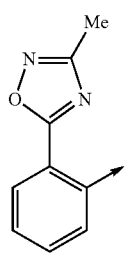 | Found 420 (MH⁺). $C_{21}H_{20}F_3N_3O_3$ requires 419 |
| 9 | D5 | CH₂ | 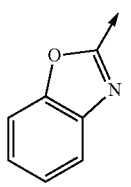 | | Found 418 (MH⁺). $C_{23}H_{23}N_5O_3$ requires 417 |

-continued
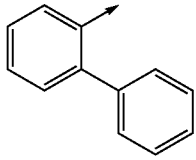
| Example | Amine | Y | Ar² | Ar¹ | Mass Spectrum (Electrospray LC/MS) API⁺ |
|---|---|---|---|---|---|
| 10 | D5 | CH₂ | 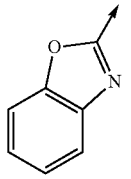 | 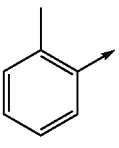 | Found 412 (MH⁺). $C_{26}H_{25}N_3O_2$ requires 411 |
| 11 | D5 | CH₂ | 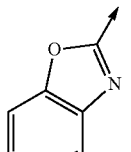 | 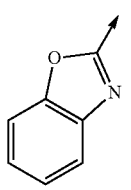 | Found 462 (MH⁺). $C_{20}H_{20}IN_3O_2$ requires 461 |
| 12 | D3 | CH₂ | Ph | 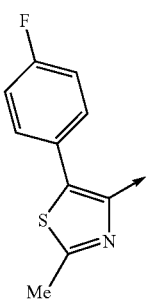 | Found 336 (MH⁺). $C_{20}H_{21}N_3O_2$ requires 335 |
| 13 | D9 | CH₂ | 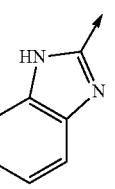 | 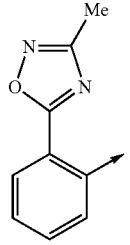 | Found 450 (MH⁺). $C_{24}H_{24}FN_5OS$ requires 449 |
| 14 | D9 | CH₂ | 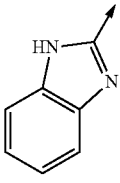 | 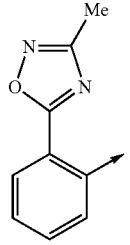 | Found 417 (MH⁺). $C_{23}H_{24}N_6O_2$ requires 416 |

-continued

| Example | Amine | Y | Ar² | Ar¹ | Mass Spectrum (Electrospray LC/MS) API⁺ |
|---------|-------|-----|-----|-----|------------------------------------------|
| 15 | D13 | CH₂ | 3-methyl-1,2,4-oxadiazol-5-yl phenyl | benzothiazol-2-yl | Found 434 (MH⁺). $C_{23}H_{23}N_5O_2S$ requires 433 |
| 16 | D13 | CH₂ | 2-(trifluoromethoxy)phenyl | benzothiazol-2-yl | Found 436 (MH⁺). $C_{21}H_{20}F_3N_3O_2S$ requires 435 |
| 17 | D13 | CH₂ | biphenyl-2-yl | benzothiazol-2-yl | Found 428 (MH⁺). $C_{26}H_{25}N_3OS$ requires 427 |
| 18 | D13 | CH₂ | 2-methyl-5-phenyl-thiazol-4-yl | benzothiazol-2-yl | Found 449 (MH⁺). $C_{24}H_{24}N_4OS_2$ requires 448 |
| 19 | D15 | CH₂ | 5-(4-fluorophenyl)-2-methyl-thiazol-4-yl | isoquinolin-1-yl | Found 461 (MH⁺). $C_{26}H_{25}FN_4OS$ requires 460 |

-continued

| Example | Amine | Y | Ar² | Ar¹ | Mass Spectrum (Electrospray LC/MS) API+ |
|---------|-------|-----|-----|-----|-----------------------------------------|
| 20 | D15 | CH₂ | 3-methyl-1,2,4-oxadiazol-5-yl phenyl | isoquinolin-1-yl | Found 428 (MH⁺). $C_{25}H_{25}N_5O_2$ requires 427 |
| 21 | D15 | CH₂ | 2-(OCF₃)phenyl | isoquinolin-1-yl | Found 430 (MH⁺). $C_{23}H_{22}F_3N_3O_2$ requires 429 |
| 22 | D15 | CH₂ | 2-methylphenyl | isoquinolin-1-yl | Found 472 (MH⁺). $C_{22}H_{22}IN_3O$ requires 471 |
| 23 | D15 | CH₂ | naphth-1-yl | isoquinolin-1-yl | Found 396 (MH⁺). $C_{26}H_{25}N_3O$ requires 395 |
| 24 | D19 | CH₂ | 2-(OCF₃)phenyl | quinoxalin-2-yl | Found 431 (MH⁺). $C_{22}H_{21}F_3N_4O_2$ requires 430 |
| 25 | D19 | CH₂ | 3-(OCF₃)phenyl | quinoxalin-2-yl | Found 431 (MH⁺). $C_{22}H_{21}F_3N_4O_2$ requires 430 |
| 26 | D19 | CH₂ | 2-methylphenyl | quinoxalin-2-yl | Found 473 (MH⁺). $C_{21}H_{21}IN_4O$ requires 472 |

-continued
| Example | Amine | Y | Ar² | Ar¹ | Mass Spectrum (Electrospray LC/MS) API⁺ |
|---|---|---|---|---|---|
| 27 | D19 | CH₂ | 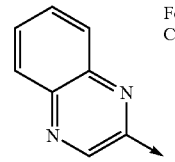 | 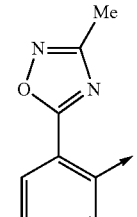 | Found 462 (MH⁺). $C_{25}H_{24}FN_5OS$ requires 461 |
| 28 | D19 | CH₂ | 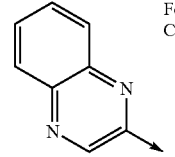 |  | Found 429 (MH⁺). $C_{24}H_{24}N_6O_2$ requires 428 |
| 29 | D33 | CH₂ | 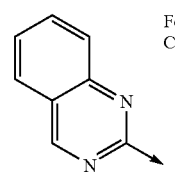 |  | Found 462 (MH⁺). $C_{25}H_{24}FN_5OS$ requires 461 |
| 30 | D35 | CH₂ | 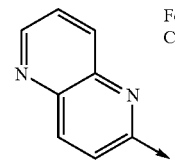 | | Found 462 (MH⁺). $C_{25}H_{24}FN_5OS$ requires 461 |

-continued

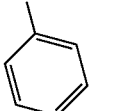

| Example | Amine | Y | Ar² | Ar¹ | Mass Spectrum (Electrospray LC/MS) API⁺ |
|---|---|---|---|---|---|
| 31 | D37 | $CH_2$ | 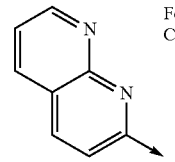 | 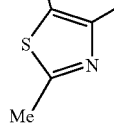 | Found 462 (MH⁺). $C_{25}H_{24}FN_5OS$ requires 461 |

EXAMPLE 32

1-[(S)-2-(Benzoxazol-2-ylaminomethyl)-piperidin-1-yl]-1-[5-(4-fluoro-phenyl-2-methyl-thiazol4-yl] methanone A mixture of amine D5 (0.05 g), 2-methyl-5-phenyl-thiazole-4-carboxylic acid (0.026 g) and diisopropylethylamine (0.06 ml) in dimethylformamide (5 ml) was treated with [O-(7-azabenzotriazol-1-yl)-1,1,3,3-tetramethyluronium hexafluorophosphate] (0.042 g) and the mixture stirred for 48 hours. The mixture was diluted with ethyl acetate, washed with sodium hydrogen carbonate and water, dried, solvent removed at reduced pressure and the residue column chromatographed (silica gel, dichloromethane-1% methanol/dichloromethane) to give the title compound (0.05 g).

Mass Spectrum (API⁺): Found 451 (MH⁺). $C_{24}H_{23}FN_4O_2S$ requires 450.

The compounds of the Examples below were prepared from the appropriate amine and acid using similar procedures to that described in Example 32.

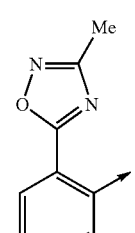

| Example | Amine | Y | Ar² | Ar¹ | Mass Spectrum (Electrospray LC/MS), API⁺ |
|---|---|---|---|---|---|
| 33 | D7 | O | 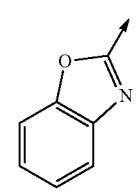 |  | Found 420 (MH⁺). $C_{22}H_{21}N_5O_4$ requires 419 |

-continued
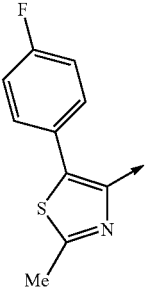
| Example | Amine | Y | Ar² | Ar¹ | Mass Spectrum (Electrospray LC/MS), API⁺ |
|---|---|---|---|---|---|
| 34 | D11 | $CH_2$ | 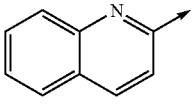 | 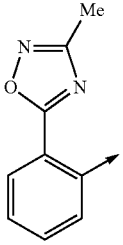 | Found 461 (MH⁺). $C_{26}H_{25}FN_4OS$ requires 460 |
| 35 | D11 | $CH_2$ | 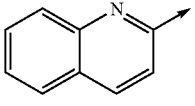 | 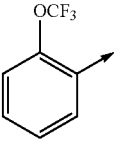 | Found 428 (MH⁺). $C_{25}H_{25}N_5O_2$ requires 427 Prepared as the HCl salt |
| 36 | D11 | $CH_2$ | 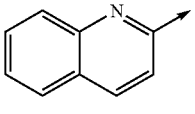 | 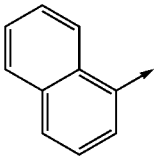 | Found 430 (MH⁺). $C_{23}H_{22}F_3N_3O_2$ requires 429 Prepared as the HCl salt |
| 37 | D13 | $CH_2$ | 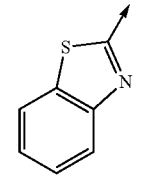 | 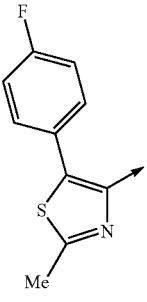 | Found 402 (MH⁺). $C_{24}H_{23}N_3OS$ requires 401 |
| 38 | D17 | $CH_2$ | 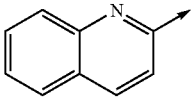 | 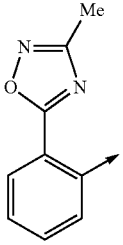 | Found 461 (MH⁺). $C_{26}H_{25}FN_4OS$ requires 460 |

-continued

| Example | Amine | Y | Ar² | Ar¹ | Mass Spectrum (Electrospray LC/MS), API⁺ |
|---|---|---|---|---|---|
| 39 | D21 | CH₂ | 2-methyl-5-(4-fluorophenyl)thiazol-4-yl | pyrimidin-2-yl | Found 412 (MH⁺). $C_{21}H_{22}FN_5OS$ requires 411 |
| 40 | D21 | CH₂ | 5-(2-substituted-phenyl)-3-methyl-1,2,4-oxadiazol | pyrimidin-2-yl | Found 379 (MH⁺). $C_{20}H_{22}N_6O_2$ requires 378 |
| 41 | D23 | CH₂ | 2-methyl-5-(4-fluorophenyl)thiazol-4-yl | pyrazin-2-yl | Found 412 (MH⁺). $C_{21}H_{22}FN_5OS$ requires 411 |
| 42 | D25 | CH₂ | 2-methyl-5-(4-fluorophenyl)thiazol-4-yl | quinazolin-4-yl | Found 462 (MH⁺). $C_{25}H_{24}FN_5OS$ requires 461 |

-continued
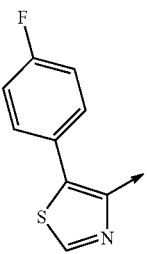
| Example | Amine | Y | Ar² | Ar¹ | Mass Spectrum (Electrospray LC/MS), API⁺ |
|---|---|---|---|---|---|
| 43 | D25 | CH₂ | 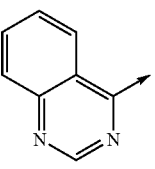 | 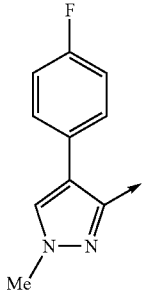 | Found 448 (MH⁺). $C_{24}H_{22}FN_5OS$ requires 447 |
| 44 | D25 | CH₂ | 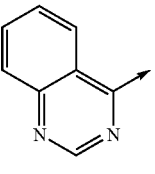 | 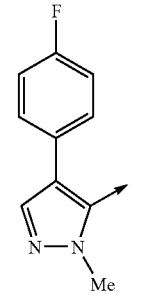 | Found 445 (MH⁺). $C_{25}H_{25}FN_6O$ requires 444 |
| 45 | D25 | CH₂ | 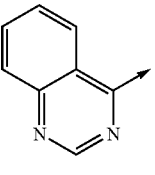 | 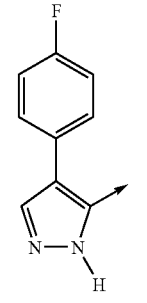 | Found 445 (MH⁺). $C_{25}H_{25}FN_6O$ requires 444 |
| 46 | D25 | CH₂ | 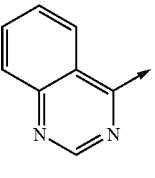 | | Found 431 (MH⁺). $C_{24}H_{23}FN_6O$ requires 430 |

-continued
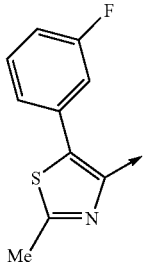
| Example | Amine | Y | Ar² | Ar¹ | Mass Spectrum (Electrospray LC/MS), API⁺ |
|---|---|---|---|---|---|
| 47 | D25 | CH₂ | 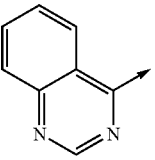 | 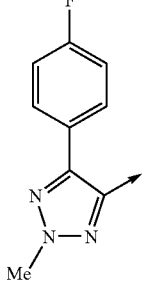 | Found 462 (MH⁺). $C_{25}H_{24}FN_5OS$ requires 461 |
| 48 | D25 | CH₂ | 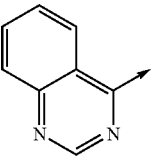 | 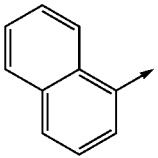 | Found 446 (MH⁺). $C_{24}H_{24}FN_7O$ requires 445 |
| 49 | D25 | CH₂ | 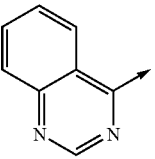 | 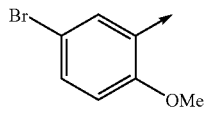 | Found 397 (MH⁺). $C_{25}H_{24}N_4O$ requires 396 |
| 50 | D25 | CH₂ | 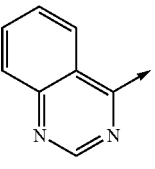 | 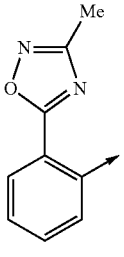 | Found 456 (MH⁺). $C_{22}H_{23}{}^{79}BrN_4O_2$ requires 455 |
| 51 | D25 | CH₂ | 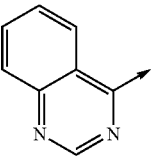 | 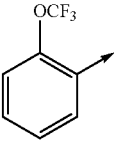 | Found 429 (MH⁺). $C_{24}H_{24}N_6O_2$ requires 428 |
| 52 | D25 | CH₂ | 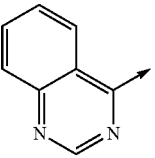 | 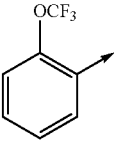 | Found 431 (MH₊). $C_{22}H_{21}F_3N_4O_2$ requires 430 |

-continued

| Example | Amine | Y | Ar² | Ar¹ | Mass Spectrum (Electrospray LC/MS), API⁺ |
|---------|-------|-----|-----|-----|------------------------------------------|
| 53 | D27 | CH₂ | 4-fluorophenyl-2-methylthiazol-5-yl | 6,7-difluoro-3-methylquinoxalin-2-yl | Found 512 (MH⁺). $C_{26}H_{24}F_3N_5OS$ requires 511 |
| 54 | D27 | CH₂ | 5-(4-fluorophenyl)thiazol-4-yl | 6,7-difluoro-3-methylquinoxalin-2-yl | Found 498 (MH⁺). $C_{25}H_{22}F_3N_5OS$ requires 497 |
| 55 | D27 | CH₂ | 4-(4-fluorophenyl)-1-methylpyrazol-3-yl | 6,7-difluoro-3-methylquinoxalin-2-yl | Found 495 (MH⁺). $C_{26}H_{25}F_3N_6O$ requires 494 |
| 56 | D27 | CH₂ | 4-(4-fluorophenyl)-1H-pyrazol-3-yl | 6,7-difluoro-3-methylquinoxalin-2-yl | Found 481 (MH⁺). $C_{25}H_{23}F_3N_6O$ requires 480 |

-continued
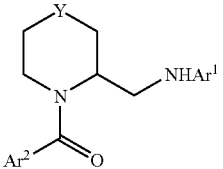
| Example | Amine | Y | Ar² | Ar¹ | Mass Spectrum (Electrospray LC/MS), API⁺ |
|---|---|---|---|---|---|
| 57 | D27 | $CH_2$ | 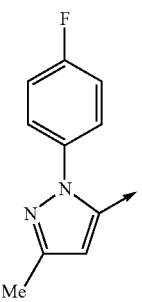 | 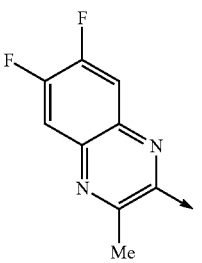 | Found 495 (MH⁺). $C_{26}H_{25}F_3N_6O$ requires 494 |
| 58 | D27 | $CH_2$ | 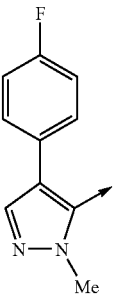 | 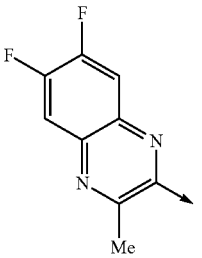 | Found 495 (MH⁺). $C_{26}H_{25}F_3N_6O$ requires 494 |
| 59 | D27 | $CH_2$ | 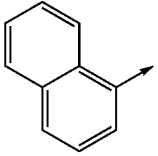 | 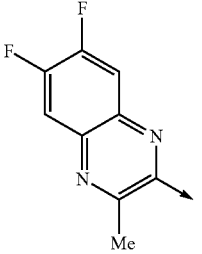 | Found 447 (MH⁺). $C_{26}H_{24}F_2N_4O$ requires 446 |
| 60 | D29 | $CH_2$ | 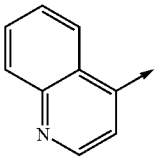 | 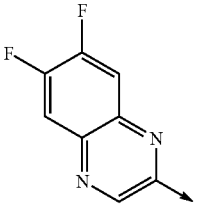 | Found 434 (MH⁺). $C_{24}H_{21}F_2N_5O$ requires 433 |

-continued
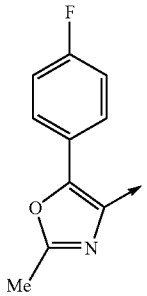
| Example | Amine | Y | Ar² | Ar¹ | Mass Spectrum (Electrospray LC/MS), API⁺ |
|---|---|---|---|---|---|
| 61 | D29 | CH₂ |  | 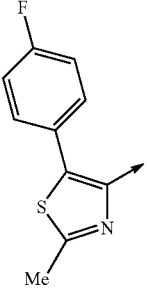 | Found 482 (MH⁺). $C_{25}H_{22}F_3N_5O_2$ requires 481 |
| 62 | D29 | CH₂ | 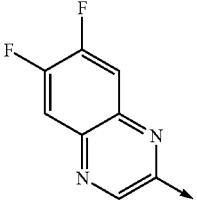 | 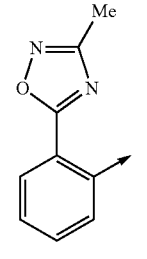 | Found 498 (MH⁺). $C_{25}H_{22}F_3N_5OS$ requires 497 |
| 63 | D29 | CH₂ | 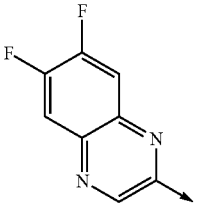 | 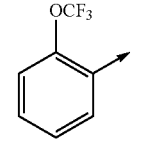 | Found 465 (MH⁺). $C_{24}H_{22}F_2N_6O_2$ requires 464 |
| 64 | D29 | CH₂ | 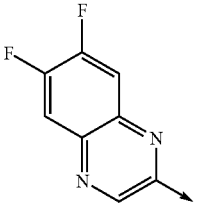 | 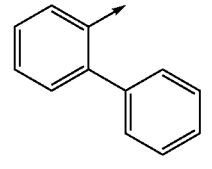 | Found 467 (MH⁺). $C_{22}H_{19}F_5N_4O_2$ requires 466 |
| 65 | D29 | CH₂ | 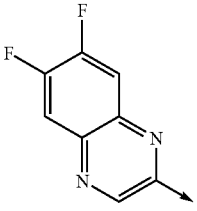 | 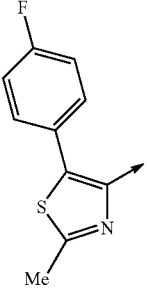 | Found 459 (MH⁺). $C_{27}H_{24}F_2N_4O$ requires 458 |

-continued

| Example | Amine | Y | Ar² | Ar¹ | Mass Spectrum (Electrospray LC/MS), API⁺ |
|---|---|---|---|---|---|
| 66 | D29 | CH₂ | 4-bromo-2-methoxyphenyl | 6,7-difluoroquinoxalin-2-yl | Found 491 (MH⁺). $C_{22}H_{21}{}^{79}BrF_2N_4O_2$ requires 490 |
| 67 | D29 | CH₂ | 4-(4-fluorophenyl)-1-methyl-1H-pyrazol-3-yl | 6,7-difluoroquinoxalin-2-yl | Found 481 (MH⁺). $C_{25}H_{23}F_3N_6O$ requires 480 |
| 68 | D29 | CH₂ | 4-(4-fluorophenyl)-1-methyl-1H-pyrazol-5-yl | 6,7-difluoroquinoxalin-2-yl | Found 481 (MH⁺). $C_{25}H_{23}F_3N_6O$ requires 480 |
| 69 | D29 | CH₂ | 4-(4-fluorophenyl)-2-methyl-2H-1,2,3-triazol-5-yl | 6,7-difluoroquinoxalin-2-yl | Found 482 (MH⁺). $C_{24}H_{22}F_3N_7O$ requires 481 |
| 70 | D29 | CH₂ | naphthalen-1-yl | 6,7-difluoroquinoxalin-2-yl | Found 433 (MH⁺). $C_{25}H_{22}F_2N_4O$ requires 432 |

-continued

| Example | Amine | Y | Ar² | Ar¹ | Mass Spectrum (Electrospray LC/MS), API⁺ |
|---|---|---|---|---|---|
| 71 | D29 | CH₂ | 5-(4-fluorophenyl)thiazol-4-yl | 6,7-difluoroquinoxalin-2-yl | Found 484 (MH⁺). $C_{24}H_{20}F_3N_5OS$ requires 483 |
| 72 | D33 | CH₂ | 4-(4-fluorophenyl)-1-methylpyrazol-3-yl | quinazolin-2-yl | Found 445 (MH⁺). $C_{25}H_{25}FN_6O$ requires 444 |
| 73 | D39 | CH₂ | 5-(2-(3-methyl-1,2,4-oxadiazol-5-yl)phenyl | oxazolo[4,5-b]pyridin-2-yl | Found 419 (MH⁺). $C_{22}H_{22}N_6O_3$ requires 418 |
| 74 | D39 | CH₂ | 2-(trifluoromethoxy)phenyl | oxazolo[4,5-b]pyridin-2-yl | Found 421 (MH⁺). $C_{20}H_{19}F_3N_4O_3$ requires 420 |
| 75 | D39 | CH₂ | 5-(4-fluorophenyl)-2-methylthiazol-4-yl | oxazolo[4,5-b]pyridin-2-yl | Found 452 (MH⁺). $C_{23}H_{22}FN_5O_2S$ requires 451 |

-continued
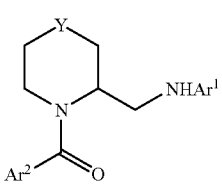
| Example | Amine | Y | Ar² | Ar¹ | Mass Spectrum (Electrospray LC/MS), API⁺ |
|---|---|---|---|---|---|
| 76 | D39 | $CH_2$ | 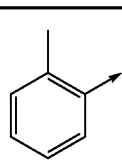 | 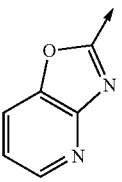 | Found 463 (MH⁺). $C_{19}H_{19}N_4O_2$ requires 462 |
| 77 | D47 | $CH_2$ | 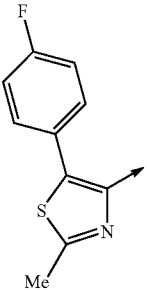 | 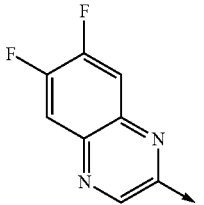 | Found 500 (MH⁺). $C_{24}H_{20}F_3N_5O_2S$ requires 499 |
| 78 | D47 | $CH_2$ | 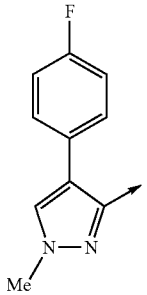 | 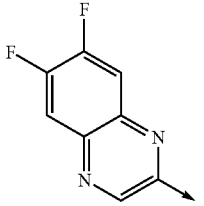 | Found 483 (MH⁺). $C_{24}H_{21}F_3N_6O_2$ requires 482 |
| 79 | D47 | O | 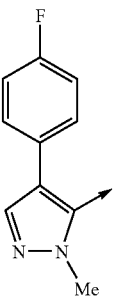 | 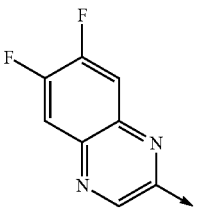 | Found 483 (MH⁺). $C_{24}H_{21}F_3N_6O_2$ requires 482 |

-continued
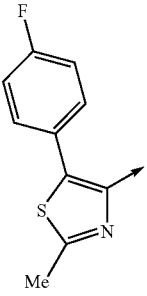
| Example | Amine | Y | Ar² | Ar¹ | Mass Spectrum (Electrospray LC/MS), API⁺ |
|---|---|---|---|---|---|
| 80 | D49 | CH₂ | 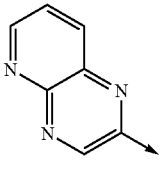 | 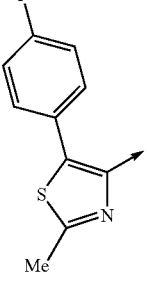 | Found 463 (MH⁺). $C_{24}H_{23}FN_6OS$ requires 462 |
| 81 | D50 | CH₂ | 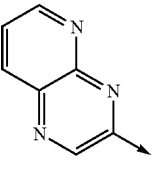 | 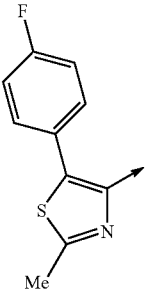 | Found 463 (MH⁺). $C_{24}H_{23}FN_6OS$ requires 462 |
| 82 | D53 | CH₂ | 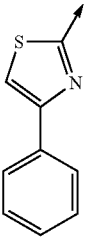 | 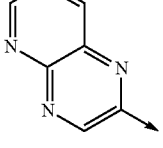 | Found 493 (MH⁺). $C_{26}H_{25}FN_4OS_2$ requires 492 |
| 83 | D29 | CH₂ | 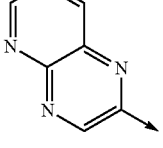 | 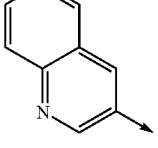 | Found 435 (MH⁺). $C_{23}H_{20}F_2N_6O$ requires 434 |
| 84 | D29 | CH₂ | 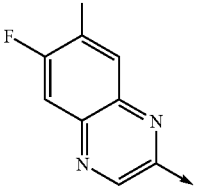 | | Found 434 (MH⁺). $C_{24}H_{21}F_2N_5O$ requires 433 |

-continued
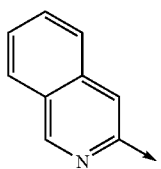
| Example | Amine | Y | Ar² | Ar¹ | Mass Spectrum (Electrospray LC/MS), API⁺ |
|---|---|---|---|---|---|
| 85 | D29 | CH₂ | 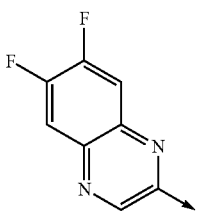 | 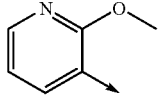 | Found 434 (MH⁺). $C_{24}H_{21}F_2N_5O$ requires 433 |
| 86 | D29 | CH₂ | 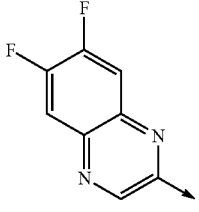 | 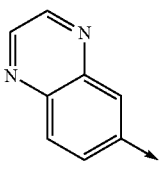 | Found 414 (MH⁺). $C_{21}H_{21}F_2N_5O_2$ requires 413 |
| 87 | D29 | CH₂ | 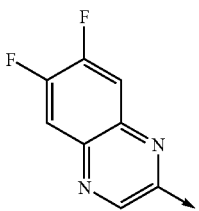 | 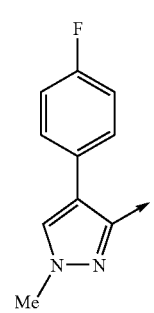 | Found 435 (MH⁺). $C_{23}H_{20}F_2N_6O$ requires 434 |
| 88 | D55 | CH₂ | 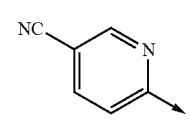 | 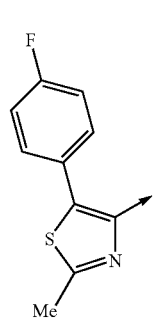 | Found 419 (MH⁺). $C_{23}H_{23}FN_6O$ requires 418 |
| 89 | D57 | CH₂ | 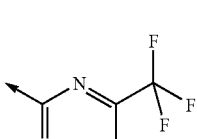 | | Found 480 (MH⁺). $C_{22}H_{21}F_4N_5OS$ requires 479 |

-continued

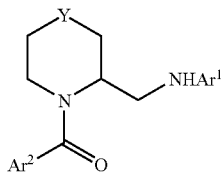

| Example | Amine | Y | Ar² | Ar¹ | Mass Spectrum (Electrospray LC/MS), API⁺ |
|---|---|---|---|---|---|
| 90 | D49 | $CH_2$ | 1H-benzimidazol-5-yl | pyrido[2,3-b]pyrazin-3-yl | Found 388 (MH⁺). $C_{21}H_{21}N_7O$ requires 387 |
| 91 | D29 | $CH_2$ | 2-dimethylamino-5-(4-fluorophenyl)thiazol-4-yl | 6,7-difluoroquinoxalin-2-yl | Found 527 (MH⁺). $C_{26}H_{25}F_3N_6OS$ requires 526 |
| 92 | D29 | $CH_2$ | 2-(3-dimethylaminopropoxy)phenyl | 6,7-difluoroquinoxalin-2-yl | Found 484 (MH⁺). $C_{26}H_{31}F_2N_5O_2$ requires 483 |
| 109 | D29 | $CH_2$ | 4-fluorobenzofuran-2-yl | 6,7-difluoroquinoxalin-2-yl | Found 441 (MH⁺). $C_{23}H_{19}F_3N_4O_2$ requires 440 |
| 110 | D62 | $CH_2$ | 5-(4-fluorophenyl)-2-methylthiazol-4-yl | 3-cyanopyridin-2-yl | Found 436 (MH⁺). $C_{23}H_{22}FN_5OS$ requires 435 |

-continued

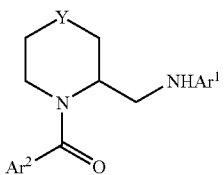

| Example | Amine | Y | Ar² | Ar¹ | Mass Spectrum (Electrospray LC/MS), API⁺ |
|---|---|---|---|---|---|
| 111 | D62 | $CH_2$ | 3-methyl-1,2,4-oxadiazol-5-yl phenyl | 3-cyanopyridin-2-yl | Found 403 (MH⁺). $C_{22}H_{22}N_6O_2$ requires 402 |
| 112 | D64 | $CH_2$ | 5-(4-fluorophenyl)-2-methylthiazol-4-yl | 5-cyanopyridin-2-yl | Found 436 (MH⁺). $C_{23}H_{22}FN_5OS$ requires 435 |
| 113 | D29 | $CH_2$ | benzo[b]thiophen-2-yl | 6,7-difluoroquinoxalin-2-yl | Found 439 (MH⁺). $C_{23}H_{20}F_2N_4OS$ requires 438 |
| 114 | D29 | $CH_2$ | 1H-benzimidazol-5-yl | 6,7-difluoroquinoxalin-2-yl | Found 423 (MH⁺). $C_{22}H_{20}F_2N_6O$ requires 422 |
| 115 | D29 | $CH_2$ | 1H-benzotriazol-5-yl | 6,7-difluoroquinoxalin-2-yl | Found 424 (MH⁺). $C_{21}H_{19}F_2N_7O$ requires 423 |

-continued
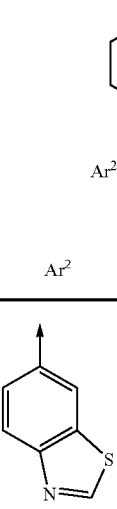
| Example | Amine | Y | Ar² | Ar¹ | Mass Spectrum (Electrospray LC/MS), API⁺ |
|---|---|---|---|---|---|
| 116 | D29 | $CH_2$ | 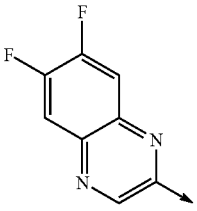 | 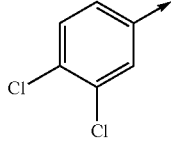 | Found 440 (MH⁺). $C_{22}H_{19}F_2N_5OS$ requires 439 |
| 117 | D29 | $CH_2$ | 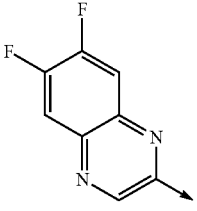 | 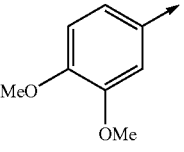 | Found 452 (MH⁺). $C_{21}H_{18}Cl_2F_2N_4O$ requires 451 |
| 118 | D29 | $CH_2$ | 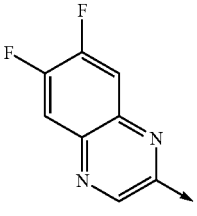 | 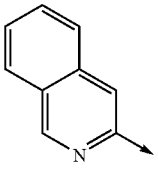 | Found 443 (MH⁺). $C_{23}H_{24}F_2N_4O_3$ requires 442 |
| 121 | D49 | $CH_2$ | 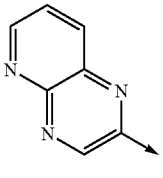 | 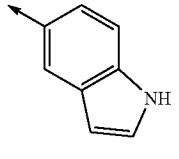 | Found 399 (MH⁺). $C_{23}H_{22}N_6O$ requires 398 |
| 122 | D49 | $CH_2$ | 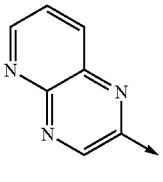 | 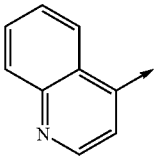 | Found 387 (MH⁺). $C_{22}H_{22}N_6O$ requires 386 |
| 123 | D49 | $CH_2$ | 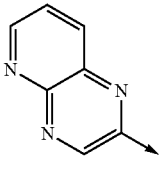 | | Found 399 (MH⁺). $C_{23}H_{22}N_6O$ requires 398 |

-continued

| Example | Amine | Y | Ar² | Ar¹ | Mass Spectrum (Electrospray LC/MS), API⁺ |
|---|---|---|---|---|---|
| 124 | D29 | $CH_2$ | 4-fluorophenyl-pyrazole-N-(2-methoxyethyl) | 6,7-difluoroquinoxalin-2-yl | Found 525 (MH⁺). $C_{27}H_{27}F_3N_6O_2$ requires 524 |
| 125 | D29 | $CH_2$ | 2,4-dimethylthiazol-5-yl | 6,7-difluoroquinoxalin-2-yl | Found 418 (MH⁺). $C_{20}H_{21}F_2N_5OS$ requires 417 |
| 126 | D29 | $CH_2$ | 5-(4-fluorophenyl)-1-methyl-1,2,3-triazol-4-yl | 6,7-difluoroquinoxalin-2-yl | Found 482 (MH⁺). $C_{24}H_{22}F_3N_7O$ requires 481 |
| 127 | D55 | $CH_2$ | 4-(4-fluorophenyl)-1-(2-methoxyethyl)pyrazol-3-yl | 5-cyanopyridin-2-yl | Found 463 (MH⁺). $C_{25}H_{27}FN_6O_2$ requires 462 |

-continued
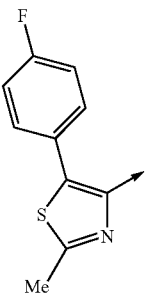
| Example | Amine | Y | Ar² | Ar¹ | Mass Spectrum (Electrospray LC/MS), API⁺ |
|---|---|---|---|---|---|
| 128 | D66 | $CH_2$ | 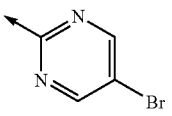 | 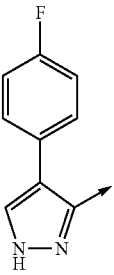 | Found 490 (MH⁺). $C_{21}H_{21}{}^{79}BrFN_5OS$ requires 489 |
| 129 | D66 | $CH_2$ | 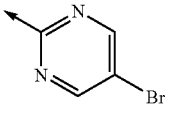 | 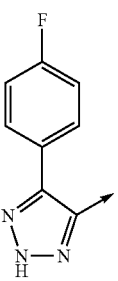 | Found 459 (MH⁺). $C_{20}H_{20}{}^{79}BrFN_6O$ requires 458 |
| 130 | D66 | $CH_2$ | 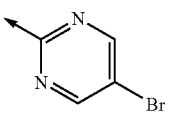 | 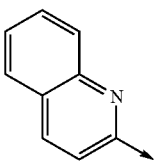 | Found 460 (MH⁺). $C_{19}H_{19}{}^{79}BrFN_7O$ requires 459 |
| 131 | D66 | $CH_2$ | 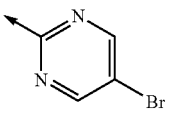 | 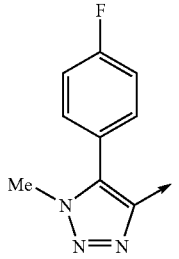 | Found 426 (MH⁺). $C_{20}H_{20}{}^{79}BrN_5O$ requires 425 |
| 132 | D66 | $CH_2$ | 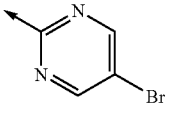 |  | Found 474 (MH⁺). $C_{20}H_{21}{}^{79}BrFN_7O$ requires 473 |

-continued
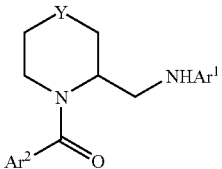
| Example | Amine | Y | Ar² | Ar¹ | Mass Spectrum (Electrospray LC/MS), API⁺ |
|---|---|---|---|---|---|
| 133 | D66 | CH₂ | 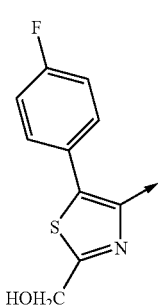 | 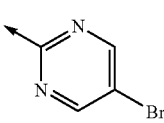 | Found 506 (MH⁺). $C_{21}H_{21}{}^{79}BrFN_5O_2S$ requires 505 |
| 134 | D66 | CH₂ | 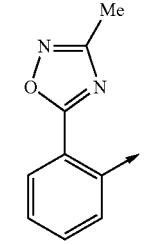 | 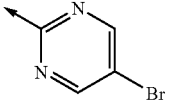 | Found 457 (MH⁺). $C_{20}H_{21}{}^{79}BrN_6O_2$ requires 456 |
| 135 | D66 | CH₂ | 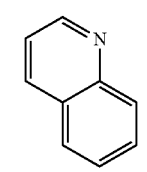 | 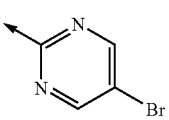 | Found 426 (MH⁺). $C_{20}H_{20}{}^{79}BrN_5O$ requires 425 |
| 136 | D68 | CH₂ | 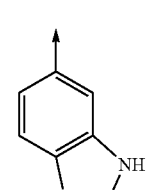 | 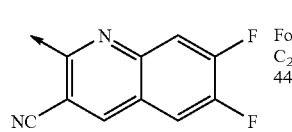 | Found 447 (MH⁺). $C_{24}H_{20}F_2N_6O$ requires 446 |
| 137 | D68 | CH₂ | 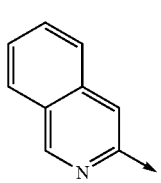 | 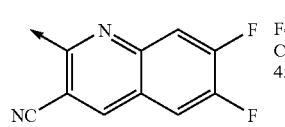 | Found 458 (MH⁺). $C_{26}H_{21}F_2N_5O$ requires 457 |

-continued
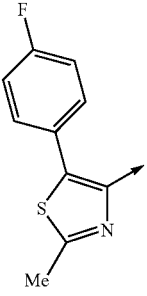
| Example | Amine | Y | Ar² | Ar¹ | Mass Spectrum (Electrospray LC/MS), API⁺ |
|---|---|---|---|---|---|
| 138 | D68 | CH₂ | 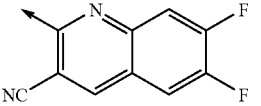 | 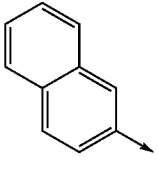 | Found 522 (MH⁺). $C_{27}H_{22}F_3N_5OS$ requires 521 |
| 139 | D68 | CH₂ | 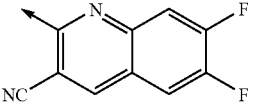 | 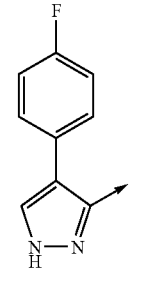 | Found 457 (MH⁺). $C_{27}H_{22}F_2N_4O$ requires 456 |
| 140 | D68 | CH₂ | 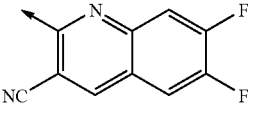 | 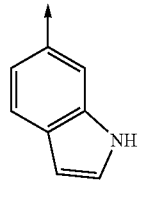 | Found 491 (MH⁺). $C_{26}H_{21}F_3N_6O$ requires 490 |
| 141 | D68 | CH₂ | 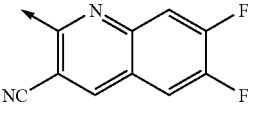 | 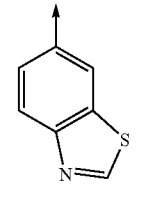 | Found 446 (MH⁺). $C_{25}H_{21}F_2N_5O$ requires 445 |
| 142 | D68 | CH₂ | 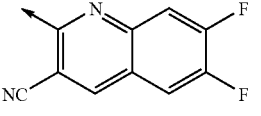 | 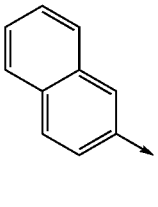 | Found 464 (MH⁺). $C_{24}H_{19}F_2N_5OS$ requires 463 |
| 143 | D29 | CH₂ | 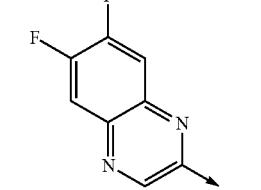 |  | Found 433 (MH⁺). $C_{25}H_{22}F_2N_4O$ requires 432 |

-continued
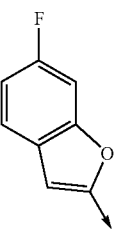
| Example | Amine | Y | Ar² | Ar¹ | Mass Spectrum (Electrospray LC/MS), API⁺ |
|---|---|---|---|---|---|
| 144 | D29 | $CH_2$ | 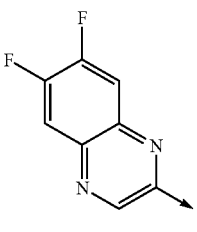 | 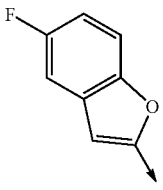 | Found 441 (MH⁺). $C_{23}H_{19}F_3N_4O_2$ requires 440 |
| 145 | D29 | $CH_2$ | 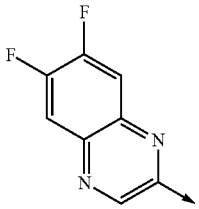 | 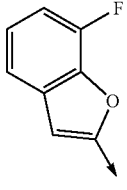 | Found 441 (MH⁺). $C_{23}H_{19}F_3N_4O_2$ requires 440 |
| 146 | D29 | $CH_2$ | 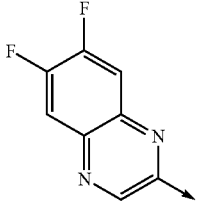 | 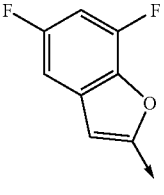 | Found 441 (MH⁺). $C_{23}H_{19}F_3N_4O_2$ requires 440 |
| 147 | D29 | $CH_2$ | 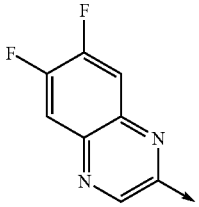 | 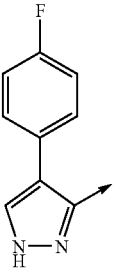 | Found 459 (MH⁺). $C_{23}H_{18}F_4N_4O_2$ requires 458 |
| 148 | D62 | $CH_2$ | 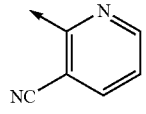 |  | Found 405 (MH⁺). $C_{22}H_{21}FN_6O$ requires 404 |

-continued

| Example | Amine | Y | Ar² | Ar¹ | Mass Spectrum (Electrospray LC/MS), API⁺ |
|---|---|---|---|---|---|
| 149 | D62 | CH₂ | 4-(4-fluorophenyl)-1-methyl-pyrazol-3-yl | 3-cyanopyridin-2-yl | Found 419 (MH⁺). $C_{23}H_{23}FN_6O$ requires 418 |
| 150 | D64 | CH₂ | 4-(4-fluorophenyl)-1-methyl-pyrazol-3-yl | 4-cyanopyridin-2-yl | Found 419 (MH⁺). $C_{23}H_{23}FN_6O$ requires 418 |
| 151 | D66 | CH₂ | 2-(3-(3-dimethylaminopropoxy)phenyl)thiophen-3-yl | 5-bromopyrimidin-2-yl | Found 558 (MH⁺). $C_{26}H_{32}{}^{79}BrN_5O_2S$ requires 557 |
| 152 | D29 | CH₂ | 2-(3-(3-dimethylaminopropoxy)phenyl)thiophen-3-yl | 6,7-difluoroquinoxalin-2-yl | Found 566 (MH⁺). $C_{30}H_{33}F_2N_5O_2S$ requires 565 |
| 153 | D29 | CH₂ | quinolin-8-yl | 6,7-difluoroquinoxalin-2-yl | Found 427 (MH⁺). $C_{20}H_{20}BrN_5O$ requires 426 |

-continued
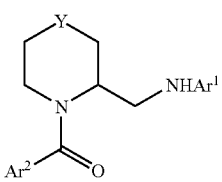
| Example | Amine | Y | Ar² | Ar¹ | Mass Spectrum (Electrospray LC/MS), API⁺ |
|---|---|---|---|---|---|
| 154 | D29 | CH₂ | 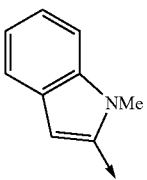 | 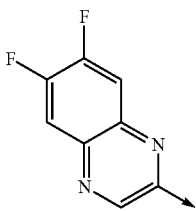 | Found 436 (MH⁺). $C_{24}H_{23}F_2N_5O$ requires 435 |
| 155 | D29 | CH₂ | 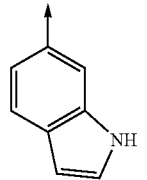 | 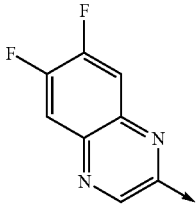 | Found 422 (MH⁺). $C_{23}H_{21}F_2N_5O$ requires 421 |
| 156 | D29 | CH₂ | 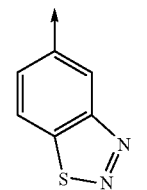 | 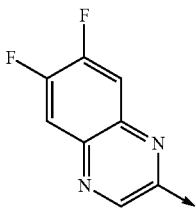 | Found 441 (MH⁺). $C_{21}H_{18}F_2N_6OS$ requires 440 |
| 157 | D29 | CH₂ | 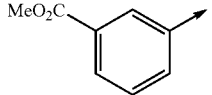 | 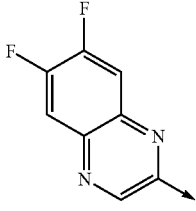 | Found 441 (MH⁺). $C_{23}H_{22}F_2N_4O_3$ requires 440 |
| 158 | D29 | CH₂ | 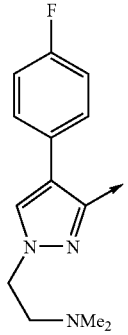 | 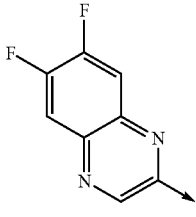 | Found 538 (MH⁺). $C_{28}H_{30}F_3N_7O$ requires 537 |

-continued

| Example | Amine | Y | Ar² | Ar¹ | Mass Spectrum (Electrospray LC/MS), API⁺ |
|---|---|---|---|---|---|
| 159 | D66 | CH₂ | 4-(4-fluorophenyl)-1-(2-(dimethylamino)ethyl)-1H-pyrazol-3-yl | 5-bromopyrimidin-2-yl | Found 530 (MH⁺). $C_{24}H_{29}{}^{79}BrFN_7O$ requires 529 |
| 160 | D49 | CH₂ | 4-(4-fluorophenyl)-1-(2-methoxyethyl)-1H-pyrazol-3-yl | pyrido[2,3-b]pyrazin-3-yl | Found 490 (MH⁺). $C_{26}H_{28}FN_7O_2$ requires 489 |
| 161 | D49 | CH₂ | 1H-benzimidazol-5-yl | pyrido[2,3-b]pyrazin-3-yl | Found 388 (MH⁺). $C_{21}H_{21}N_7O$ requires 387 |
| 162 | D66 | CH₂ | 1H-benzimidazol-5-yl | 5-bromopyrimidin-2-yl | Found 415 (MH⁺). $C_{18}H_{19}{}^{79}BrN_6O$ requires 414 |
| 163 | D66 | CH₂ | benzofuran-2-yl | 5-bromopyrimidin-2-yl | Found 415 (MH⁺). $C_{19}H_{19}{}^{79}BrN_4O_2$ requires 414 |

-continued
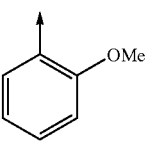
| Example | Amine | Y | Ar² | Ar¹ | Mass Spectrum (Electrospray LC/MS), API⁺ |
|---|---|---|---|---|---|
| 164 | D66 | CH₂ | 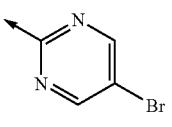 | 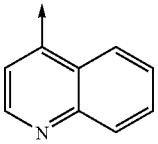 | Found (MH⁺) 405 $C_{18}H_{21}{}^{79}BrN_4O_2$ requires 404 |
| 165 | D66 | CH₂ | 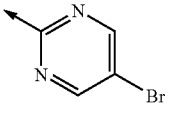 | 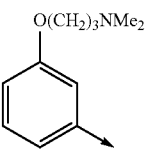 | Found 426 (MH⁺). $C_{20}H_{20}{}^{79}BrN_5O$ requires 425 |
| 166 | D29 | CH₂ | 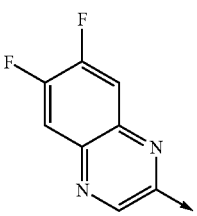 | 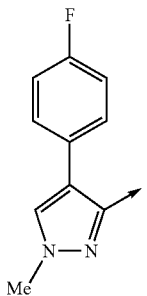 | Found 484 (MH⁺). $C_{26}H_{31}F_2N_5O_2$ requires 483 |
| 170 | D66 | CH₂ | 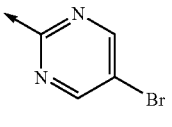 | 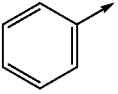 | Found 473 (MH⁺). $C_{21}H_{22}{}^{79}BrFN_6O$ requires 472 |
| 175 | D66 | CH₂ | 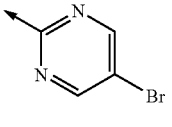 | 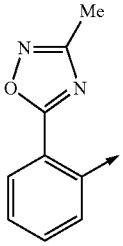 | Found 375 (MH⁺). $C_{17}H_{19}{}^{79}BrN_4O$ requires 374. |
| 199 | D7 | O | 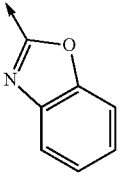 |  | Found 420 (MH⁺). $C_{22}H_{21}N_5O_4$ requires 419. |

-continued
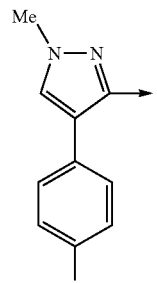
| Example | Amine | Y | Ar² | Ar¹ | Mass Spectrum (Electrospray LC/MS), API⁺ |
|---|---|---|---|---|---|
| 204 | D82 | CH$_2$ | 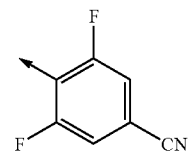 | 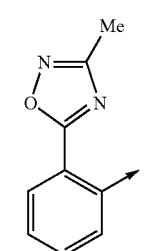 | Found 454 (MH⁺). C$_{24}$H$_{22}$F$_3$N$_5$O requires 453 |
| 206 | D82 | CH$_2$ | 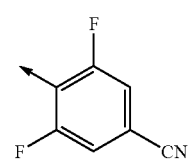 | 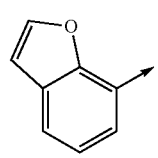 | Found 438 (MH⁺). C$_{23}$H$_{21}$F$_2$N$_5$O$_2$ requires 437. |
| 207 | D82 | CH$_2$ | 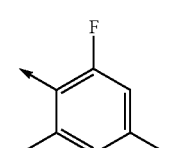 | 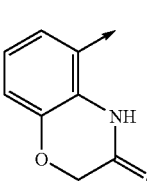 | Found 396 (MH⁺). C$_{22}$H$_{19}$F$_2$N$_3$O$_2$ requires 395. |
| 230 | D66 | CH$_2$ | 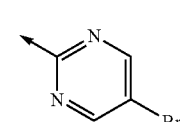 | 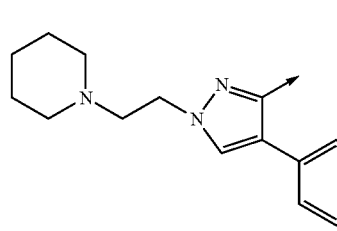 | Found 446 (MH⁺). C$_{19}$H$_{20}$$^{79}$BrN$_5$O$_3$ requires 445. |
| 231 | D66 | CH$_2$ | 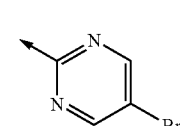 | 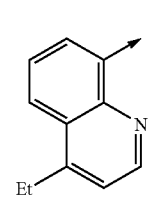 | Found 570 (MH⁺). C$_{27}$H$_{33}$$^{79}$BrFN$_7$O requires 569. |
| 241 | D66 | CH$_2$ | 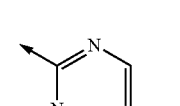 | 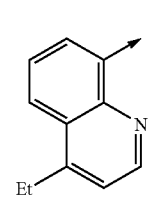 | Found 454 (MH⁺). C$_{22}$H$_{24}$$^{79}$BrN$_5$O requires 453 |

-continued
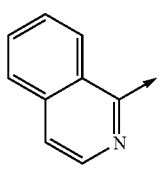
| Example | Amine | Y | Ar² | Ar¹ | Mass Spectrum (Electrospray LC/MS), API⁺ |
|---|---|---|---|---|---|
| 242 | D66 | $CH_2$ | 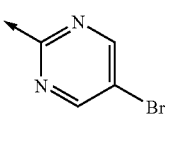 | 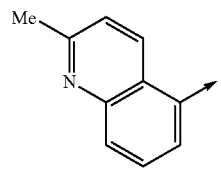 | Found 448 (MNa⁺). $C_{20}H_{20}{}^{79}BrN_5O$ requires 425. |
| 243 | D66 | $CH_2$ | 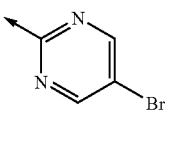 | 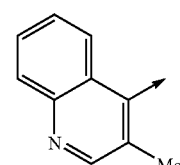 | Found 440 (MH⁺). $C_{21}H_{22}{}^{79}BrN_5O$ requires 439. |
| 244 | D66 | $CH_2$ | 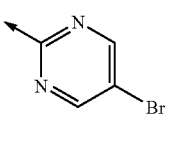 | 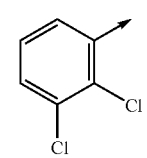 | Found 440 (MH⁺). $C_{21}H_{22}{}^{79}BrN_5O$ requires 439. |
| 245 | D66 | $CH_2$ | 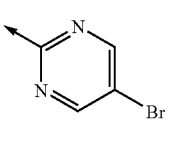 | 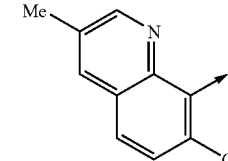 | Found 443 (MH⁺). $C_{17}H_{17}{}^{79}Br{}^{35}Cl_2N_4O$ requires 442. |
| 246 | D66 | $CH_2$ | 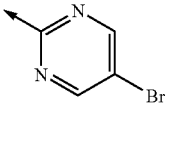 | 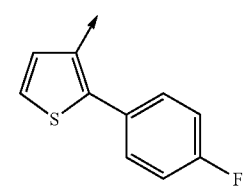 | Found 474 (MH⁺). $C_{21}H_{21}{}^{79}Br{}^{35}ClN_5O$ requires 473. |
| 259 | D80 | O | 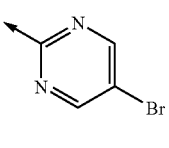 | 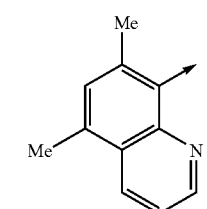 | Found 476 (MH⁺). $C_{21}H_{19}{}^{79}BrFN_3O_2S$ requires 475. |
| 260 | D66 | $CH_2$ | 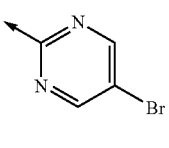 | | Found 454 (MH⁺). $C_{22}H_{24}{}^{79}BrN_5O$ requires 453. |

-continued
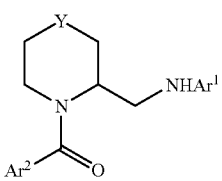
| Example | Amine | Y | Ar² | Ar¹ | Mass Spectrum (Electrospray LC/MS), API⁺ |
|---|---|---|---|---|---|
| 261 | D66 | CH₂ | 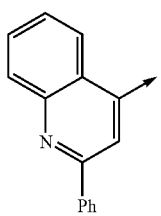 | 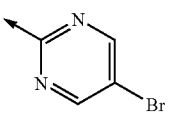 | Found 502 (MH⁺). $C_{26}H_{24}{}^{79}BrN_5O$ requires 501. |
| 262 | D66 | CH₂ | 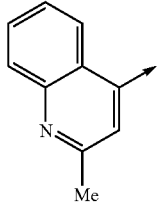 | 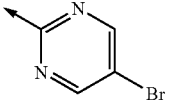 | Found 440 (MH⁺). $C_{21}H_{22}{}^{79}BrN_5O$ requires 439. |
| 263 | D66 | CH₂ | 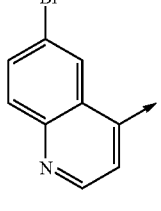 | 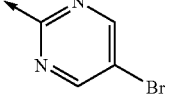 | Found 504 (MH⁺). $C_{20}H_{19}{}^{79}Br_2N_5O$ requires 503. |
| 264 | D66 | CH₂ | 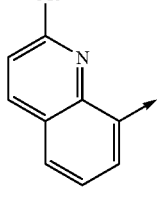 | 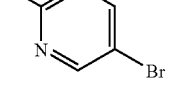 | Found 440 (MH⁺). $C_{21}H_{22}{}^{79}BrN_5O$ requires 439. |
| 265 | D66 | CH₂ | 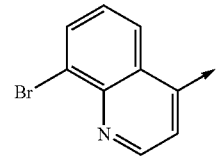 | 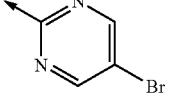 | Found 504 (MH⁺). $C_{20}H_{19}{}^{79}Br_2N_5O$ requires 503. |
| 266 | D66 | CH₂ | 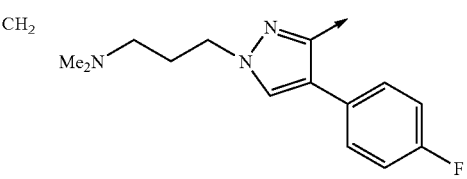 | 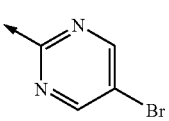 | Found 544 (MH⁺). $C_{25}H_{31}{}^{79}BrFN_7O$ requires 543. |

EXAMPLE 93

1-{2-[(6,7-Difluoro-quinoxalin-2-ylamino)-methyl]-pyrrolidin-1-yl}-1-[4-(4-fluoro-phenyl)-2-H-pyrazol-3-yl]-methanone The amine of D31 (0.085 g) in dimethylformamide (3 ml) was treated with 4-(fluoro-phenyl)-2H-pyrazole-3-carboxylic acid (0.125 g), diisopropylethylamine (0.07 ml) and [O-(7-azabenzotriazol-1-yl)-1,1,3,3-tetramethyluronium hexafluorophosphate] (0.11 g). the mixture was shaken for 48 hours. Solvent was removed at reduced pressure and the residue extracted with dichloromethane. The filtrate was evaporated under reduced pressure and the residue column chromatographed (silica gel, 3% methanol/diethyl ether) to give the title compound (0.1 g).

Mass Spectrum (API$^+$): Found 453 (MH$^+$). $C_{23}H_{19}F_3N_6O$ requires 452.

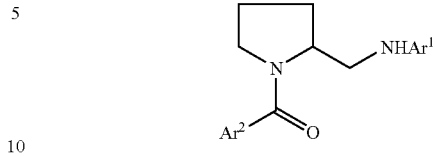

residue column chromatographed (silica gel, 3% methanoly-diethyl ether) to give the title compound (0.1 g).

Mass Spectrum (API$^+$): Found 453 (MH$^+$). $C_{23}H_{19}F_3N_6O$ requires 452.

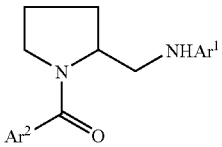

| Example | Amine | Ar$^2$ | Ar$^1$ | Mass Spectrum (Electrospray LC/MS), API$^+$ |
|---|---|---|---|---|
| 94 | D31 | 5-(4-fluorophenyl)-2-methylthiazol-4-yl | 6,7-difluoroquinoxalin-2-yl | Found 484 (MH$^+$). $C_{24}H_{20}F_3N_5OS$ requires 483 |
| 95 | D31 | 1-(4-fluorophenyl)-3-methyl-1H-pyrazol-5-yl | 6,7-difluoroquinoxalin-2-yl | Found 467 (MH$^+$). $C_{24}H_{21}F_3N_6O$ requires 466 |
| 96 | D31 | 5-(4-fluorophenyl)-2-methyl-2H-1,2,3-triazol-4-yl | 6,7-difluoroquinoxalin-2-yl | Found 468 (MH$^+$). $C_{23}H_{20}F_3N_7O$ requires 467 |

-continued
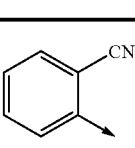
| Example | Amine | Ar² | Ar¹ | Mass Spectrum (Electrospray LC/MS), API⁺ |
|---|---|---|---|---|
| 97 | D31 | 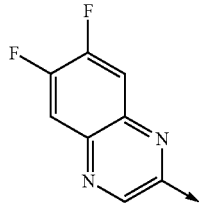 | 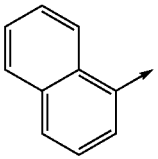 | Found 394 (MH⁺). $C_{21}H_{17}F_2N_5O$ requires 393 |
| 98 | D31 | 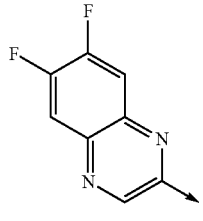 | 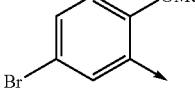 | Found 419 (MH⁺). $C_{24}H_{20}F_2N_4O$ requires 418 |
| 99 | D31 | 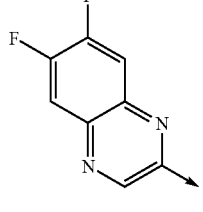 | 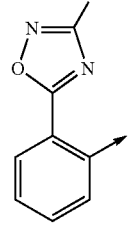 | Found 478 (MH⁺). $C_{21}H_{19}BrF_2N_4O_2$ requires 477 |
| 100 | D31 | 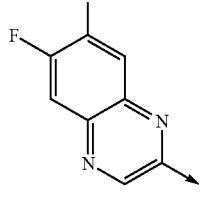 | 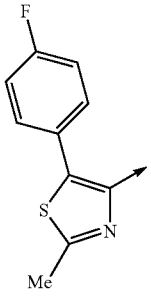 | Found 451 (MH⁺). $C_{23}H_{20}F_2N_6O_2$ requires 450 |
| 101 | D45 | 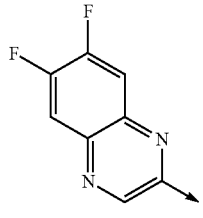 | 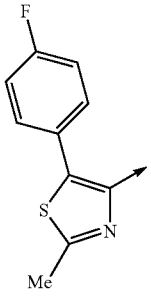 | Found 484 (MH⁺). $C_{24}H_{20}F_3N_5OS$ requires 483 |

-continued

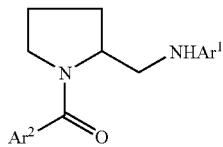

| Example | Amine | Ar² | Ar¹ | Mass Spectrum (Electrospray LC/MS), API⁺ |
|---|---|---|---|---|
| 102 | D45 | 5-(4-fluorophenyl)thiazol-4-yl | 6,7-difluoroquinoxalin-2-yl | Found 470 (MH⁺). $C_{23}H_{18}F_3N_5OS$ requires 469 |
| 103 | D45 | 3-methyl-5-(2-fluorophenyl)-1,2,4-oxadiazol-5-yl | 6,7-difluoroquinoxalin-2-yl | Found 451 (MH⁺). $C_{23}H_{20}F_2N_6O_2$ requires 450 |
| 104 | D45 | 4-(4-fluorophenyl)-1H-pyrazol-3-yl | 6,7-difluoroquinoxalin-2-yl | Found 453 (MH⁺). $C_{23}H_{19}F_3N_6O$ requires 452 |
| 119 | D45 | 4-(4-fluorophenyl)-1-ethyl-1H-pyrazol-3-yl | 6,7-difluoroquinoxalin-2-yl | Found 481 (MH⁺). $C_{25}H_{23}F_3N_6O$ requires 480 |

-continued
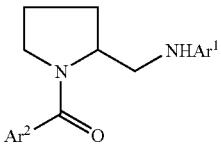
| Example | Amine | Ar² | Ar¹ | Mass Spectrum (Electrospray LC/MS), API⁺ |
|---|---|---|---|---|
| 120 | D45 |  | 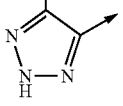 | Found 454 (MH⁺). $C_{22}H_{18}F_3N_7O$ requires 453 |
| 167 | D70 | 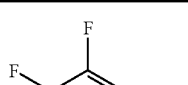 | 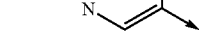 | Found 459 (MH⁺). $C_{20}H_{20}{}^{79}BrFN_6O$ requires 458 |
| 168 | D45 |  | 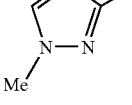 | Found 470 (MH⁺). $C_{23}H_{18}F_3N_5OS$ requires 469 |
| 169 | D45 | 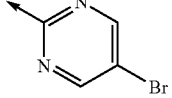 |  | Found 467 (MH⁺). $C_{24}H_{21}F_3N_6O$ requires 466 |

-continued
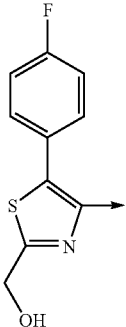
| Example | Amine | Ar² | Ar¹ | Mass Spectrum (Electrospray LC/MS), API⁺ |
|---|---|---|---|---|
| 176 | D70 | 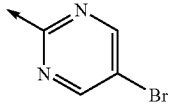 | 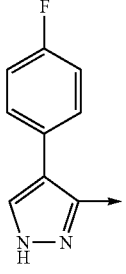 | Found 514 (MNa⁺). $C_{20}H_{19}{}^{79}BrFN_5O_2S$ requires 491. |
| 177 | D70 | 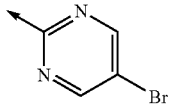 | 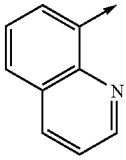 | Found 445 (MH⁺). $C_{19}H_{18}{}^{79}BrFN_6O$ requires 444. |
| 178 | D70 | 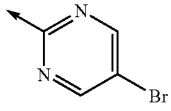 | 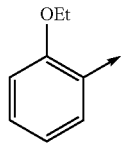 | Found 434 (MNa⁺). $C_{19}H_{18}{}^{79}BrN_5O$ requires 411. |
| 179 | D70 | 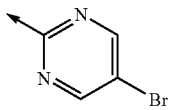 | 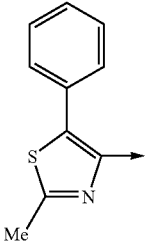 | Found 405 (MH⁺). $C_{18}H_{21}{}^{79}BrN_4O_2$ requires 404. |
| 180 | D70 | 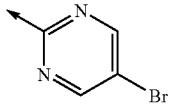 | | Found 458 (MH⁺). $C_{20}H_{20}{}^{79}BrN_5OS$ requires 457. |

-continued
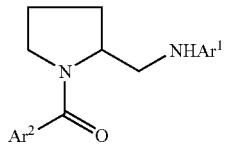
| Example | Amine | Ar² | Ar¹ | Mass Spectrum (Electrospray LC/MS), API⁺ |
|---|---|---|---|---|
| 181 | D70 | 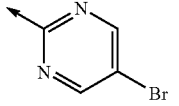 | 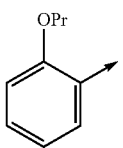 | Found 559 (MH⁺). $C_{25}H_{31}{}^{79}BrN_6O_2S$ requires 558. |
| 182 | D70 | 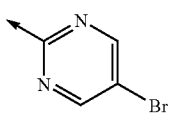 | 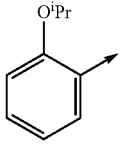 | Found 419 (MH⁺). $C_{19}H_{23}{}^{79}BrN_4O_2$ requires 418. |
| 183 | D70 | 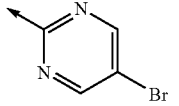 | 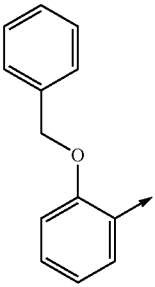 | Found 419 (MH⁺). $C_{19}H_{23}{}^{79}BrN_4O_2$ requires 418. |
| 184 | D70 | 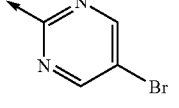 | 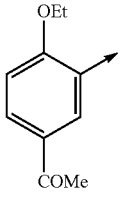 | Found 467 (MH⁺). $C_{23}H_{23}{}^{79}BrN_4O_2$ requires 466. |
| 185 | D70 | 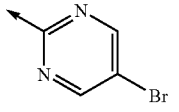 | 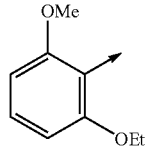 | Found 447 (MH⁺). $C_{20}H_{23}{}^{79}BrN_4O_3$ requires 446. |
| 186 | D70 | 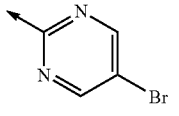 | | Found 435 (MH⁺). $C_{19}H_{23}{}^{79}BrN_4O_3$ requires 434. |

-continued

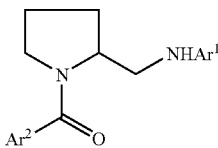

| Example | Amine | Ar² | Ar¹ | Mass Spectrum (Electrospray LC/MS), API⁺ |
|---|---|---|---|---|
| 187 | D70 | 2-Me-6-OEt-phenyl | 5-Br-pyrimidin-2-yl | Found 419 (MH⁺). $C_{19}H_{23}^{79}BrN_4O_2$ requires 418 |
| 188 | D70 | 2-OEt-naphth-1-yl | 5-Br-pyrimidin-2-yl | Found 455 (MH⁺). $C_{22}H_{23}^{79}BrN_4O_2$ requires 454. |
| 189 | D70 | 5-(2-F-phenyl)-2-Me-thiazol-4-yl | 5-Br-pyrimidin-2-yl | Found 476 (MH⁺). $C_{20}H_{19}^{79}BrFN_5OS$ requires 475. |
| 190 | D70 | 5-(3-F-phenyl)-2-Me-thiazol-4-yl | 5-Br-pyrimidin-2-yl | Found 476 (MH⁺). $C_{20}H_{19}^{79}BrFN_5OS$ requires 475. |
| 191 | D70 | 5-(2-F-phenyl)-thiazol-4-yl | 5-Br-pyrimidin-2-yl | Found 462 (MH⁺). $C_{19}H_{17}^{79}BrFN_5OS$ requires 461. |
| 192 | D70 | 5-phenyl-thiazol-4-yl | 5-Br-pyrimidin-2-yl | Found 444 (MH⁺). $C_{19}H_{18}^{79}BrN_5OS$ requires 443. |

-continued
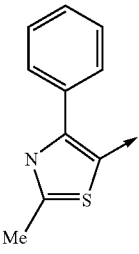
| Example | Amine | Ar² | Ar¹ | Mass Spectrum (Electrospray LC/MS), API⁺ |
|---|---|---|---|---|
| 193 | D70 | 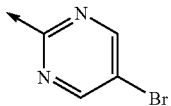 | 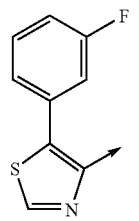 | Found 458 (MH⁺). $C_{20}H_{20}^{79}BrN_5OS$ requires 457. |
| 201 | D70 | 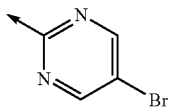 | 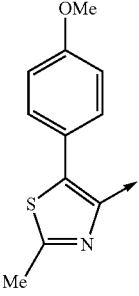 | Found 462 (MH⁺). $C_{20}H_{17}^{79}BrFN_5OS$ requires 461. |
| 202 | D70 | 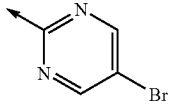 | 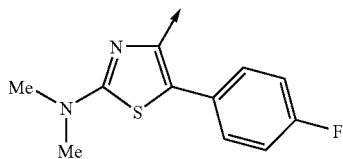 | Found 488 (MH⁺). $C_{21}H_{22}^{79}BrN_5O_2S$ requires 487. |
| 209 | D70 | 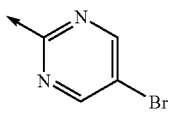 | 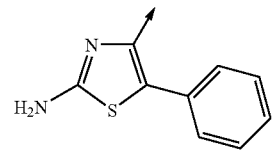 | Found 505 (MH⁺). $C_{21}H_{22}^{79}BrFN_6OS$ requires 504 |
| 210 | D70 | 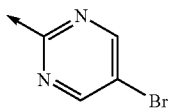 | 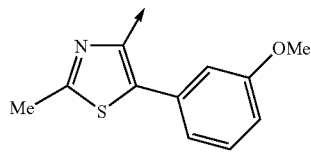 | Found 459 (MH⁺). $C_{19}H_{19}^{79}BrN_6OS$ requires 458. |
| 211 | D70 | 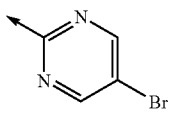 | | Found 488 (MH⁺). $C_{21}H_{22}^{79}BrN_5O_2S$ requires 487. |

-continued

| Example | Amine | Ar² | Ar¹ | Mass Spectrum (Electrospray LC/MS), API⁺ |
|---|---|---|---|---|
| 212 | D70 | 2-(4-fluorophenyl)thiophen-3-yl | 5-bromopyrimidin-2-yl | Found 461 (MH⁺). $C_{20}H_{18}{}^{79}BrFN_4OS$ requires 460. |
| 213 | D70 | 2-(pyridin-2-yl)phenyl | 5-bromopyrimidin-2-yl | Found 460 (MH⁺). $C_{21}H_{20}{}^{79}BrN_5O$ requires 437. |
| 214 | D70 | 5-fluoro-2-(3-methyl-1,2,4-oxadiazol-5-yl)phenyl | 5-bromopyrimidin-2-yl | Found 461 (MH⁺). $C_{19}H_{18}{}^{79}BrFN_6O_2$ requires 460. |
| 215 | D70 | 2-(4-methoxyphenyl)thiophen-3-yl | 5-bromopyrimidin-2-yl | Found 473 (MH⁺). $C_{21}H_{21}{}^{79}BrN_4O_2$ requires 472. |
| 219 | D70 | 2-methoxy-5-(4-fluorophenyl)thiazol-4-yl | 5-bromopyrimidin-2-yl | Found 492 (MH⁺). $C_{20}H_{19}{}^{79}BrFN_5O_2S$ requires 491. |
| 220 | D70 | 4-fluoro-2-(3-methyl-1,2,4-oxadiazol-5-yl)phenyl | 5-bromopyrimidin-2-yl | Found 461 (MH⁺). $C_{19}H_{18}{}^{79}BrFN_6O_2$ requires 460. |
| 221 | D70 | 2-phenylthiophen-3-yl | 5-bromopyrimidin-2-yl | Found 443 (MH⁺). $C_{20}H_{19}{}^{79}BrN_4OS$ requires 442. |
| 222 | D70 | 4'-cyanobiphenyl-2-yl | 5-bromopyrimidin-2-yl | Found 462 (MH⁺). $C_{23}H_{20}{}^{79}BrN_5O$ requires 461. |

-continued

| Example | Amine | Ar² | Ar¹ | Mass Spectrum (Electrospray LC/MS), API⁺ |
|---|---|---|---|---|
| 223 | D70 | 2-(3-methoxyphenyl)thiophen-3-yl | 5-bromopyrimidin-2-yl | Found 473 (MH⁺). $C_{21}H_{21}{}^{79}BrN_4O_2S$ requires 472. |
| 224 | D70 | 2-(1H-pyrazol-1-yl)phenyl | 5-bromopyrimidin-2-yl | Found 449 (MNa⁺). $C_{19}H_{19}{}^{79}BrN_6O$ requires 426. |
| 232 | D70 | 1-(2-(dimethylamino)ethyl)-4-(4-fluorophenyl)-1H-pyrazol-3-yl | 5-bromopyrimidin-2-yl | Found 516 (MH⁺). $C_{23}H_{27}{}^{79}BrFN_7O$ requires 515. |
| 233 | D70 | 2-ethyl-5-(4-fluorophenyl)thiazol-4-yl | 5-bromopyrimidin-2-yl | Found 490 (MH⁺). $C_{21}H_{21}{}^{79}BrFN_5OS$ requires 489. |
| 247 | D95 | 2-methyl-5-(4-chlorophenyl)thiazol-4-yl | 5-chloropyrimidin-2-yl | Found 448 (MH⁺). $C_{20}H_{19}{}^{35}Cl_2N_5OS$ requires 447. |
| 248 | D93 | 3-methyl-5-(2-phenyl)-1,2,4-oxadiazol | 5-acetylpyrimidin-2-yl | Found 407 (MH⁺). $C_{21}H_{22}N_6O_3$ requires 406. |
| 250 | D70 | 4-ethylquinolin-8-yl | 5-bromopyrimidin-2-yl | Found 440 (MH⁺). $C_{21}H_{22}{}^{79}BrN_5O$ requires 439. |

-continued
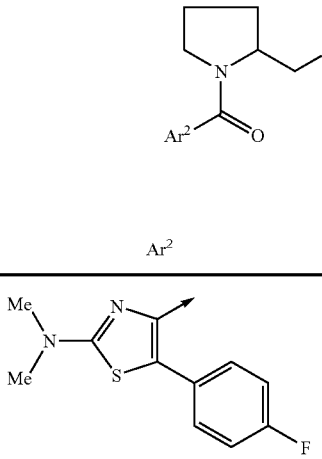
| Example | Amine | Ar² | Ar¹ | Mass Spectrum (Electrospray LC/MS), API⁺ |
|---|---|---|---|---|
| 251 | D95 | 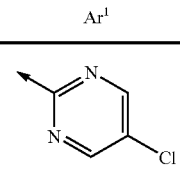 | 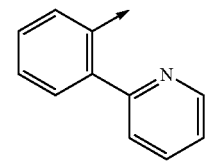 | Found 461 (MH⁺). $C_{21}H_{22}{}^{35}ClFN_6OS$ requires 460. |
| 252 | D95 | 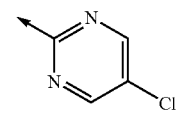 | 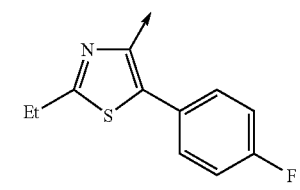 | Found 416 (MNa⁺). $C_{21}H_{20}{}^{35}ClN_5O$ requires 393. |
| 253 | D95 | 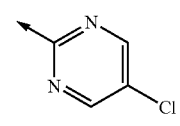 | 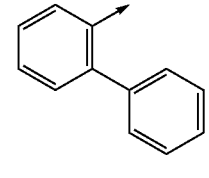 | Found 468 (MNa⁺). $C_{21}H_{21}{}^{35}ClFN_5OS$ requires 445. |
| 254 | D95 | 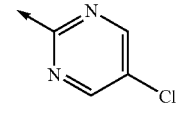 | 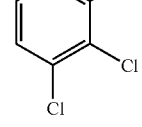 | Found 393 (MH⁺). $C_{22}H_{21}{}^{35}ClN_4O$ requires 392. |
| 255 | D70 | 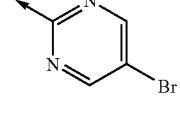 | 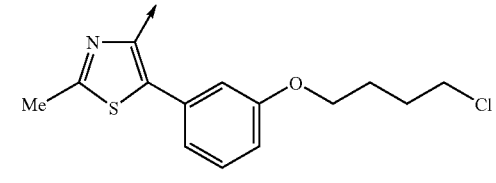 | Found 429 (MH⁺). $C_{16}H_{15}{}^{79}Br{}^{35}Cl_2N_4O$ requires 428. |
| 256 | D95 | 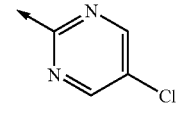 | 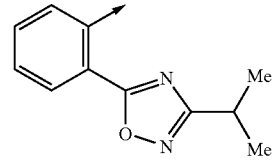 | Found 520 (MH⁺). $C_{24}H_{27}{}^{35}Cl_2N_5O_2S$ requires 519. |
| 257 | D95 | 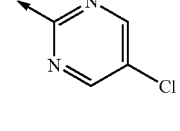 | | Found 427 (MH⁺). $C_{21}H_{23}{}^{35}ClN_6O_2$ requires 426. |

-continued

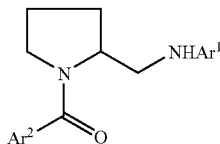

| Example | Amine | Ar² | Ar¹ | Mass Spectrum (Electrospray LC/MS), API⁺ |
|---|---|---|---|---|
| 258 | D70 | (2-phenyl group with 3-(1-methylethyl)-1,2,4-oxadiazol-5-yl) | 5-bromo-pyrimidin-2-yl | Found 471 (MH⁺). $C_{21}H_{23}{}^{79}BrN_6O_2$ requires 470. |

EXAMPLE 105

1-[2-(3-Methyl-[1,2,4]oxadiazol-5-yl)-phenyl]-1-[(S)-2-(oxazolo[4,5-b]]pyridin-2-ylaminomethyl)-piperidin-1-yl]-methanone The compound of D41 (0.51 g) and 2-methylsulfanyl-oxazolo[4,5-b]pyridine (0.25 g) were combined and heated under argon at 90° C. for 18 hours The mixture was column chromatographed (5% methanol, diethyl ether eluant) to give the title compound (0.26 g)
Mass Spectrum (API⁺): Found 419 (MH⁺). $C_{22}H_{22}N_6O_3$ requires 418.

EXAMPLE 106

1-[2-(3-Methyl-[1,2,4]oxadiazol-5-yl)-phenyl]-{(R)-2-[(methyl-oxazolo[4,5b]pyridin-2-yl-amino)-methyl]piperidin-1-yl}-methanone The title compound (0.015 g) was prepared from the compound of D43 (0.15 g) according to the method of Example 105.
Mass Spectrum (API⁺): Found 433 (MH⁺). $C_{23}H_{24}N_6O_3$ requires 432.

EXAMPLE 107

6-[((S)-1-{1-[4-(4-Fluoro-phenyl)-1-methyl-1H-pyrazol-3-yl]-methanoyl}-piperidin-2-ylmethyl)-methyl-amino]-nicotinonitrile The title compound (0.078 g) was prepared from the compound of D60 (0.45 g) and 2-chloro-5-cyanopyridine (0.189 g) according to the method of D26
Mass Spectrum (API⁺): Found 433 (MH⁺). $C_{24}H_{25}FN_6O$ requires 432.

EXAMPLE 108

1-((S)2-{[(6,7-Difluoro-quinoxalin-2-yl)methyl-amino]-methyl}-piperidin-1-yl)-1-[4-(4-fluoro-phenyl)-1-methyl-1H-pyrazol-3-yl]-methanone The title compound (0.031 g) was prepared from the compound of D60 (0.15 g) and 2-chloro-6,7difluoroquinoxaline (0.091 g) according to the method of D26

Mass Spectrum (API⁺): Found 495 (MH⁺). $C_{26}H_{25}F_3N_6O$ requires 494.

EXAMPLE 171

1-{2-[((S)1-{1-[4-(4-Fluoro-phenyl)-1-methyl-1H-pyrazol-3-yl]-methanoyl}-piperidin-2-ylmethyl)-amino]-pyrimidin-5yl}-ethanone A mixture of 1-{(S)-2-[(5-Bromo-pyrimidin-2-ylamino)-methyl]-piperidin-1-yl}-1-[4-(4-fluoro-phenyl)-1-methyl-1H-pyrazol-3-yl]-methanone (0.5 g) and 1-ethoxyvinyl) tributyltin (0.42 ml) tetrakis(triphenylphosphine)palladium [0] (0.06 g) was boiled in dioxane (8 ml) for 16 h. 2N Hydrochloric acid was added, the mixture stirred for 90 min, water was added and the mixture extracted (×3) with ethyl acetate. The combined ethyl acetate extracts were dried, solvent removed at reduced pressure and the residue column chromatographed (silica gel, ethyl acetate→2% methanol ethyl acetate to give the title compound (0.3 g) as a yellow foam.
Mass Spectrum (API⁺): Found 437 (MH⁺). $C_{23}H_{25}FN_6O_2$ requires 436.

EXAMPLE 172

1-[4-(4-Fluoro-phenyl)-1-methyl-1H-pyrazol-3-yl]-1-((S)-2-{[5-(1-hydroxy-ethyl)-pyrimidin-2-ylamino]-methyl}-piperidin-1-yl)-methanone 1-{2-[((S)-1-{1-[4-(4-Fluoro-phenyl)-1-methyl-1H-pyrazol-3-yl]-methanoyl}-piperidin-2-ylmethyl)-amino]-pyrimidin-5-yl}-ethanone (0.2 g) was dissolved in methanol 20 ml) and sodium borohydride (0.4 g) added. The reaction was stirred overnight, water was added and stirring continued for 30 min. The reaction mixture was extracted with ethyl acetate (×3), the organic extracts combined, dried (MgSO₄) and solvent removed at reduced pressure to give the title compound as a colourless foam.
Mass Spectrum (API⁺): Found 439 (MH⁺). $C_{23}H_{27}FN_6O_2$ requires 438.

EXAMPLE 173

2-[((S)-1-{1-[4-(4-Fluoro-phenyl)-1-methyl-1H-pyrazol-3-yl]-methanoyl}-piperidin-2-ylmethyl)-amino]-pyrimidine-5-carbonitrile 1-{(S)-2-[(5-Bromo-pyrimidin-2-ylamino)methyl]-piperidin-1-yl}-1-[4-4-fluoro-phenyl)-1-methyl-1H-pyrazol-3-yl]-methanone (0.35 g) in N-methylpyrrolidinone (10 ml) containing copper(I)cyanide (0.13 g) was heated to reflux for 5 h. The reaction mixture was diluted with water, filtered (Kieselguhr) and the filtrate extracted with ethyl acetate. The ethyl acetate phase was washed with water and brine, dried (MgSO4), filtered and solvent removed at reduced pressure. The residue was column chromatographed (silica gel; ethyl acetate:pentane 1:1→ ethyl acetate eluant), the appropriate fractions combined and solvent removed at reduced pressure to give the title compound (0.019 g).
Mass Spectrum (API$^+$): Found 420 (MH$^+$). $C_{22}H_{22}FN_7O$ requires 419.

EXAMPLE 174

3-(1-{(S)-2-[(6,7-Difluoro-quinoxalin-2-ylamino)-methyl]-piperidin-1-yl}-methanoyl)-N-methyl-benzamide The compound of description 71 (0.10 g) was dissolved in dimethylformamide (5 ml) containing HATU (0.095 g) and diisopropylethylamine (0.131 ul) and stirred for 30 in. Methylamine (1M in tetrahydrofuran, 0.125 ml) was added and stirring continued for 16. The reaction mixture was diluted with diethyl ether, washed with water (×3), saturated brine and dried (MgSO$_4$). Solvent was removed at reduced pressure and the residue column chromatographed (silica gel; ethyl acetate→10% methanol:ethyl acetate to give the title compound (0.018 g).
Mass Spectrum (API$^+$): Found 440 (MH$^+$). $C_{23}H_{23}F_2N_5O_2$ requires 439.

EXAMPLE 194

1-{(S)-2-[(5-Bromo-pyrimidin-2-ylamino)methyl]-pyrrolidin-1-yl}-1-[5-(4-fluoro-phenyl)-2-methyl-thiazol-4-yl]-methanone A mixture of the amine of D70 (0.070 g), 5-(4-fluoro-phenyl)-2-methyl-thiazole-4-carboxylic acid (0.065 g), 1-(3-dimethylaminopropyl)-3-ethylcarbodiimide hydrochloride (EDC) (0.042 g) and 1-hydroxybenzotriazole hydrate (0.037 g) in dimethylformamide (2 ml) was stirred at ambient temperature for 18 h, evaporated in vacuo and the residue partitioned between ethyl acetate and water. The organic layer was dried (Na$_2$SO$_4$), evaporated and the residue chromatographed on silica gel eluting with a 30% -100% ethyl acetate in pentane gradient to afford the title product (0.083 g) as a white solid. Mass-Spectrum (Electrospray LC/MS), API$^+$: Found 476 (MH$^+$). $C_{20}H_{19}{}^{79}FN_5OS$ requires 475.

EXAMPLE 195

1-{(S)-[(5-Bromo-pyrimidin-2-ylamino)-methyl]-pyrrolidin-1-yl}-1-[2-(3-methyl-[1,2,4]oxadiazol-5-yl)-phenyl]-methanone The title compound (0.053 g) was obtained from the amine of D70 (0.070 g) and 2-(3-methyl-[1,2,4]oxadiazol-5-yl)-benzoic acid (0.056 g) using the method of Example 194. Mass Spectrum (Electrospray LC/MS): Found 443 (MH$^+$). $C_{19}H_{19}{}^{79}BrN_6O_2$ requires 442.

EXAMPLE 196

1-{(S)-2-[5-Bromo-pyrimidin-2-ylamino)-methyl]-pyrrolidin-1-yl}-1-[5-(4-chloro-phenyl)-2-methyl-thiazol4-yl]-methanone The title compound (0.078 g) was obtained from the amine of D70 (0.077 g) and 5-(4-chloro-phenyl)-2-methyl-thiazole-4-carboxylic acid (0.076 g) according to the method of Example 32. Mass spectrum (Electrospray LC/MS), API$^+$: Found 492 (MH$^+$). $C_{20}H_{19}{}^{79}Br^{35}ClN_5OS$ requires 491.

EXAMPLE 197

1-{(S)-2-[(5-Bromo-pyridin-2-ylamino)-methyl]-pyrrolidin-1-yl}-1-[5-(4-fluoro-phenyl)-2-methyl-thiazol4-yl]-methanone The title compound (0.135 g) was obtained from the amine of D74 (0.11 g) and 5-(4fluoro-phenyl)-2-methyl-thiazole-4-carboxylic acid (0.12 g) according to the method of Example 32. Mass Spectrum API$^+$: Found 475 (MH$^+$). $C_{21}H_{20}{}^{79}BrFN_4OS$ requires 474.

EXAMPLE 198

1-{(S)-2-[(5-Bromo-pyridin-2-ylamino)-methyl]-pyrrolidin-1-yl}-1-[4-(4-fluoro-phenyl)-1-methyl-1H-pyrazol-3-yl]-methanone The title compound (0.10 g) was obtained from the amine of D74 (0.11 g) and 4-(4-fluoro-phenyl)-1-methyl-1H-pyrazole-3 carboxylic acid (0.12 g) according to the method of Example 32. Mass Spectrum API$^+$: Found 458 (MH$^+$). $C_{21}H_{21}{}^{79}BrFN_5O$ requires 457.

EXAMPLE 200

1-{3-[(5-Bromo-pyrimidin-2-ylamino)-methyl]-morpholin-4-yl}-1-[4-(4-fluoro-phenyl)-1-methyl-1H-pyrazol-3-yl]-methanone The title compound (0.393 g) was obtained from the compound of D80 (0.3 g) and 4-4-fluorophenyl)-1-methyl-1H-pyrazole-3-carboxylic acid (0.242 g) according to the method of Example 32. Mass Spectrum (API$^+$): Found 475 (MH$^+$). $C_{20}H_{20}{}^{79}BrFN_6O_2$ requires 474.

EXAMPLE 203

3,5-Difluoro4-[((S)1-1-[5-4-fluorophenyl)-2-methyl-thiazol-4yl]-methanoyl)-piperidin-2-ylmethyl)-amino]-benzonitrile The title compound (0.090 g) was obtained from the compound of D82 (0.073 g) and 5-(4-fluorophenyl)-2-methyl-thiazole-4-carboxylic acid (0.069 g) according to the method of Example 32. Mass Spectrum (Electrospray LC/MS): Found 471. $C_{24}H_{21}F_3N_4OS$ requires 470.

EXAMPLE 208

3,5-Difluoro-4-[((S)-1-{1-[5-(4-fluoro-phenyl)-2-methyl-thiazol-4-yl]-methanoyl}-pyrrolidin-2-ylmethyl)-amino]-benzonitrile The title compound (0.09 g) was obtained from the compound of D84 and 5-(4-fluoro-phenyl)-2-methyl-thiazolecarboxylic acid (0.095 g) according to the method of Example 32. Mass Spectrum (Electrospray LC/MS): Found 457 (MH$^+$). $C_{23}H_{19}F_3N_4OS$ requires 456.

EXAMPLE 216

1-{(S)-2-[(5-Ethyl-pyrimidin-2-ylamino)-methyl]-pyrrolidin-1-yl}-1-[5-(4-fluoro-phenyl)-2-methyl-thiazol-4-yl]-methanone The title compound (0.05 g) was obtained from the compound of D86 (0.07 g) and 5-(4-fluoro-phenyl)-2-methyl-thiazole-4-carboxylic acid (0.068 g) according to the method of Example 32. Mass Spectrum (Electrospray LC/MS): Found 426 (MH$^+$). $C_{22}H_{24}FN_5OS$ requires 425.

EXAMPLE 217

1((S)-2-{[(5-Bromo-pyrimidin-2-yl)-methyl-amino]-methyl}-pyrrolidin-1-yl)-1-[5-(4-fluoro-phenyl)-2-methyl-thiazol-4-yl]-methanone The title compound (0.1g) was obtained from the compound of D91 (0.275 g) and 5-(4-fluoro-phenyl)-2-methyl-thiazole-4-carboxylic acid (0.285 g) according to the method of Example 32. Mass Spectrum (Electrospray LC/MS): Found 490 (MH$^+$). $C_{21}H_{21}{}^{79}FN_5OS$ requires 489.

EXAMPLE 218

1-((S)-2-{([(5-Bromo-pyrimidin-2-yl)-methyl-amino]-methyl}-pyrrolidin-1-yl)-1-[4-(4-fluoro-phenyl)-1-methyl-1H-pyrazol-3-yl]-methanone The title compound (0.02 g) was obtained from the compound of D91 (0.275 g) and 4-(4-fluoro-phenyl)-1-methyl-1H-pyrazole-3-carboxylic acid (0.260 g) according to the method of Example 32. Mass Spectrum (Electrospray LC/MS): Found 473 (MH$^+$). $C_{21}H_{22}{}^{79}BrFN_6O$ requires 472.

EXAMPLE 225

1-{2-[((S)-1-{1-[5-(4-Chloro-phenyl)-2-methyl-thiazol-4-yl]-methanoyl}-pyrrolidin-2-ylmethyl)-amino]-pyrimidin-5-yl}-ethanone The title product (0.04 g) was obtained from the compound of D93 (0.133 g) and 5-(4-chloro-phenyl)-2-methyl-thiazole-4-carboxylic acid (0.076 g) using a similar procedure to that described in Example 32. Mass Spectrum (Electrospray LC/MS): Found 456 (MH$^+$). $C_{22}H_{22}{}^{35}ClN_5O_2S$ requires 455.

EXAMPLE 226

1-{(S)-2-[(5-Chloro-pyrimidin-2-ylamino)-methyl]-pyrrolidin-1-yl}-1-[5-(4-fluoro-phenyl)-2-methyl-thiazol-4-yl]-methanone The title product (0.095 g) was obtained from the amine of D95 (0.064 g) and 5-(4-fluorophenyl)-2-methyl-thiazole-4-carboxylic acid (0.071 g) using the method of Example 32. Mass Spectrum (Electrospray LC/MS): Found 432 (MH$^+$). $C_{20}H_{19}{}^{35}ClFN_5OS$ requires 431.

EXAMPLE 227

1-{(S)-2-[(5-Chloro-pyrimidin-2-ylamino)-methyl]-pyrrolidin-1-yl}-1-[2-(3-methyl-[1,2,4]oxadiazol-5-yl)-phenyl]-methanone The title compound (0.052 g) was obtained from the amine of D95 (0.064 g) and 2-(3-methyl-[1,2,4]oxadiazol-5-yl)-benzoic acid (0.061 g) according to the method of Example 32. Mass Spectrum (Electrospray LC/MS): Found 399 (MH$^+$). $C_{19}H_{19}{}^{35}ClN_6O_2$ requires 398.

EXAMPLE 228

1-[5-(4-Fluoro-phenyl)-2-methyl-thiazol-4-yl]-1-{(S)-2-[(5-methyl-pyrimidin-2-ylamino)-methyl]-pyrrolidin-1-yl}-methanone To the compound of Example 194 (0.36 g) in dimethylformamide was added lithium chloride (0.096 g), tetramethyl tin (0.126 ml) and dichlorobis(triphenylphosphine) palladium (0) (0.035 g) and the resulting mixture heated at 100° C. under argon for 18 h. The reaction was then evaporated, diluted with dichloromethane, filtered and the filtrate washed with water, dried and evaporated. Chromatography of the residue on silica gel, eluting with methanol-dichloromethane mixtures, afforded the title product (0.2 g) as a yellow amorphous solid. Mass Spectrum (API$^+$): Found 412 (MH$^+$). $C_{21}H_{22}FN_5OS$ requires 411.

EXAMPLE 229

6-[((S)-1-{1-[5-(4Fluoro-phenyl)-2-methyl-thiazol-4-yl]-methanoyl}-pyrrolidin-2-ylmethyl)-amino]-nicotinonitrile A mixture of the amine of D97 (0.134 g), 5-(4-fluoro-phenyl)-2-methyl-thiazole-4-carboxylic acid (0.172 g), EDC (0.139 g) and 1-hydroxybenzotriazole (0.01 g) in dichloromethane (8 ml) was stirred at ambient temperature for 7 days. The reaction was washed with saturated aqueous sodium bicarbonate solution, dried and evaporated. Chromatography of the residue on silica gel, eluting with ethyl acetate-hexane mixtures afforded the title product (0.196 g). Mass Spectrum (Electrospray LC/MS): Found 422 (MH$^+$). $C_{22}H_{20}FN_5OS$ requires 421.

EXAMPLE 234

1-[5-(4-Fluoro-phenyl)-2-methyl-thiazol-4-yl]-1-{(S)-2-[6-methyl-2-methylsulfanyl-pyrimidin-4-ylamino)-methyl]-pyrrolidin-1-yl}-methanone The title product (0.095 g) was obtained from the amine of D101 (0.15 g) and the compound of D98 (0.14 g) using a similar method to that described in D69. Mass Spectrum (Electrospray LC/MS): Found 458 (MH$^+$). $C_{22}H_{24}FN_5OS_2$ requires 457.

EXAMPLE 235

1-[5-(4-Fluoro-phenyl)2-methyl-thiazol-4-yl]-1-{(S)-2-[(2-methylsulfanyl-pyrimidin-4-ylamino)-methyl]-pyrrolidin-1-yl}-methanone The title compound (0.05 g) was obtained from the amine of D101 (0.15 g) and 4-chloro-2-methylsulfanyl-pyrimidine (0.076 g) using a similar method to that described in D69. Mass Spectrum (Electrospray LC/MS): Found 444 (MH$^+$). $C_{21}H_{22}FN_5OS_2$ requires 443.

The following compounds were prepared using methods similar to that described in Examples 234 and 235.

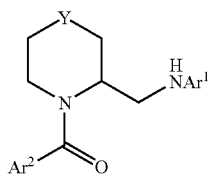

| Example | Amine | Y | Ar$^2$ | Ar$^1$ | Mass spectrum (Electrospray LC/MS), API$^+$ |
|---|---|---|---|---|---|
| 236 | D101 | Bond | 2-Me-thiazol-5-yl-(4-F-phenyl) | 4,6-diMe-2-CF$_3$-pyrimidin-5-yl | Found 494 (MH$^+$). $C_{23}H_{23}F_4N_5OS$ requires 493. |
| 237 | D101 | Bond | 2-Me-thiazol-5-yl-(4-F-phenyl) | 2,6-diMe-pyrimidin-4-yl | Found 426 (MH$^+$). $C_{22}H_{24}FN_5OS$ requires 425. |
| 238 | D101 | Bond | 2-Me-thiazol-5-yl-(4-F-phenyl) | 6-CF$_3$-pyrimidin-4-yl | Found 466 (MH$^+$). $C_{21}H_{19}F_4N_5OS$ requires 465. |

EXAMPLE 239

1-(3-{[(5-Bromo-pyrimidin-2-yl)-methyl-amino]-methyl}-morpholin-4-yl)-1-[5-(4-fluoro-phenyl)-2-methyl-thiazol-4-yl]-methanone The title compound (0.056 g) was obtained from the compound of D105 (0.095 g) and 5-(4-fluorophenyl)-2-methyl-thiazole-4-carboxylic acid (0.10 g) according to the method of Example 32. Mass Spectrum (Electrospray LC/MS): Found 506 (MH$^+$). $C_{21}H_{21}{}^{79}BrFN_5O_2S$ requires 505.

EXAMPLE 240

1-(3-{[(5-Bromo-pyrimidin-2-yl)methyl-amino]-methyl}-morpholin-4-yl)-1-[2-(4fluoro-phenyl)-thiophen-3-yl]-methanone To the compound of D105 (0.095 g) in dichloromethane (8 ml) containing triethylamine (0.06 ml) was added 2-(4-fluorophenyl)-thiophene-3-carbonyl chloride (0.084 g). After 72 h at ambient temperature the reaction mixture was washed with brine, dried and evaporated; the residue was chromatographed on silica gel, eluting with ethyl acetate-pentane mixtures to afford the title product (0.093 g). Mass Spectrum (Electrospray LC/MS): Found 491 (MH$^+$). $C_{21}H_{20}{}^{79}BrFN_4O_2S$ requires 490.

EXAMPLE 249

1-[5-(4Fluoro-phenyl)-2-methyl-thiazol-4-yl]-1-{(S)-2-[(5-trifluoromethyl-pyrimidin-2-ylamino)-methyl]-pyrrolidin-1-yl}-methanone

EXAMPLE 249

1-[5-(4-Fluoro-phenyl)-2-methyl-thiazol-4-yl]-1-{(S)-2-[(5-trifluoromethyl-pyrimidin-2-ylamino)-methyl]-pyrrolidin-1-yl}-methanone To the compound from Example 194 (0.36 g) in dimethylformamide (5 ml) was added potassium trifluoroacetate (0.23 g), copper iodide (0.3 g) and toluene (5 ml) and the resulting mixture heated at reflux under Dean-Stark conditions for 3 h, before refluxing for a further 20 h. The reaction mixture was cooled, poured into water/ether and filtered through kieselguhr. The aqueous layer from the filtrate was extracted with ether, and the combined ether extracts washed with water, dried and evaporated. The aqueous was re-extracted with dichloromethane and the extract evaporated. The combined extracts were chromatographed on silica gel, eluting with methanol-dichloromethane mixtures, to afford the title product (0.001 g). Mass Spectrum (lectrospray LC/MS): Found 466 (MH$^+$). $C_{21}H_{19}F_4N_5OS$ requires 465.

The compounds in the table below were prepared using methods described above

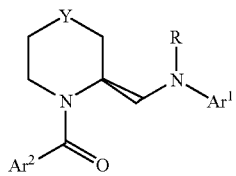

| Example | X | R | Ar$^2$ | Ar$^1$ | Mass Spectrum (Electrospray LC/MS), API$^+$ |
|---|---|---|---|---|---|
| 267 | CH$_2$ | H | 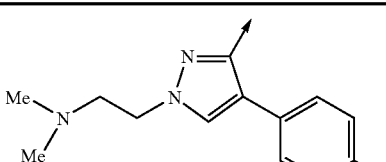 | 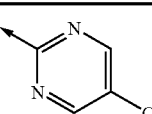 | Found 486 (MH$^+$). $C_{24}H_{29}{}^{35}ClFN_7O$ requires 485. |
| 268 | CH$_2$ | H | 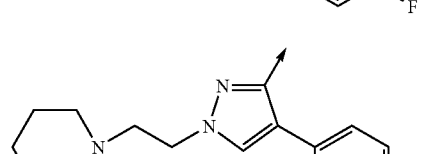 | 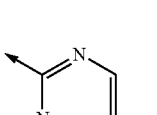 | Found 526 (MH$^+$). $C_{27}H_{33}{}^{35}ClFN_7O$ requires 525. |
| 269 | CH$_2$ | H | 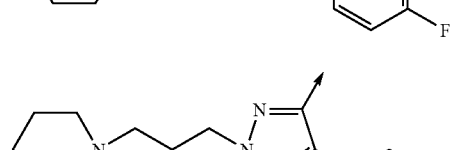 | 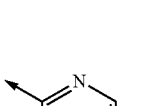 | Found 540 (MH$^+$). $C_{28}H_{35}{}^{35}ClFN_7O$ requires 539. |

-continued

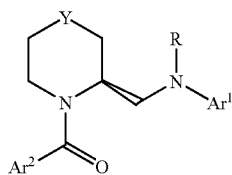

| Example | X | R | Ar² | Ar¹ | Mass Spectrum (Electrospray LC/MS), API⁺ |
|---|---|---|---|---|---|
| 270 | CH₂ | Me | isoquinolin-1-yl | 5-bromopyrimidin-2-yl | Found 440 (MH⁺). $C_{21}H_{22}{}^{79}BrN_5O$ requires 439. |
| 271 | CH₂ | Me | 2,3-dichlorophenyl | 5-bromopyrimidin-2-yl | Found 457 (MH⁺). $C_{18}H_{19}{}^{79}Br^{35}Cl_2N_4O$ requires 456. |
| 272 | CH₂ | H | 2-(dimethylaminomethyl)-5-(4-fluorophenyl)thiazol-4-yl | 5-chloropyrimidin-2-yl | Found 489 (MH⁺). $C_{23}H_{26}{}^{35}ClFN_6OS$ requires 488. |
| 273 | CH₂ | Me | 3-methylquinolin-4-yl | 5-bromopyrimidin-2-yl | Found 454 (MH⁺). $C_{22}H_{24}{}^{79}BrN_5O$ requires 453. |
| 274 | CH₂ | Me | 2-methylquinolin-4-yl | 5-bromopyrimidin-2-yl | Found: 454 (MH⁺). $C_{22}H_{24}{}^{79}BrN_5O$ requires 453. |
| 275 | CH₂ | H | 2-methyl-5-(4-fluorophenyl)thiazol-4-yl | 5-chloropyrimidin-2-yl | Found 446 (MH⁺). $C_{21}H_{21}{}^{35}ClFN_5OS$ requires 445. |

It is understood that the present invention covers all combinations of particular and preferred groups described herein above.

Determination of Orexin-1 Receptor Antagonist Activity

The orexin-1 receptor antagonist activity of the compounds of formula (I) was determined in accordance with the following experimental method.

Experimental Method

CHO-DG44 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been precoated with 10 μg/well of poly-L-lysine from SIGMA. The seeded plates were incubated overnight at 37C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5mM probenecid; pH7.4). Antagonists were prepared as 10 mM stocks in DMSO (100%). Antagonist IC50 values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37° C. in 5% CO2. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37C in 5% $CO_2$ for 30 minutes. Cell plates were then transferred to the Fluorescent Imaging Plate Reader (FLIPR, Molecular Devices) instrument Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 seconds (during continuous reading). From each well peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS,* 1995, 16, 413-417) to generate a concentration effect value. Antagonist Kb values were calculated using the equation:

$$Kb = IC50/(1+([3/EC50])$$

where EC50 was the potency of human orexin-A determined in the assay (in nM terms) and IC50 is expressed in molar terms.

Compounds of Examples tested according to this method had pKb values in the range 6.7-9.7 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11× half log unit dilutions (Biomek 2000, Beckman) in Tyrode's buffer containing probenecid (10 mn HEPES with 145 mM NaCl, 10 mM glucose, 2.5 mM KCl, 1.5 mM $CaCl_2$, 1.2 mM $MgCl_2$ and 2.5mM probenecid; pH7.4). Antagonists were prepared as 10 mM stocks in DMSO (100%). Antagonist IC50 values (the concentration of compound needed to inhibit 50% of the agonist response) were determined against 10.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37 C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37 C in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1-19 inclusive was subtracted from this figure. The peak increase in fluorescence was plotted against compound concentration and iteratively curve fitted using a four parameter logistic fit (as described by Bowen and Jerman, *TiPS,* 1995, 16, 413-417) to generate a concentration effect value. Antagonist Kb values were calculated using the equation:

$$Kb = IC50/(1+([3/EC50])$$

where EC50 was the potency of human orexin-A determined in the assay (in nM terms) and IC50 is expressed in molar terms. Compounds of Examples tested according to this method had pKb values in the range <6.3-9.1 at the human cloned orexin-2 receptor.

The application of which this description and claims forms part may be used as a basis for priority in respect of any subsequent application. The claims of such subsequent application maybe directed to any feature or combination of features described herein. They may take the form of product, composition, process, or use claims and may include, by way of example and without limitation the following claims:

The invention claimed is:

1. A compound of formula (I):

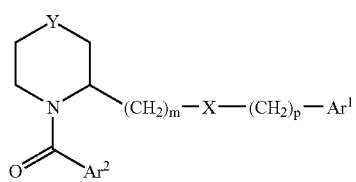

wherein:
Y represents a group $(CH_2)_n$, wherein n represents 1;
m represents 1;
p represents 0;
X is NR, wherein R is H or $(C_{1-4})$alkyl;
$Ar^1$ is optionally substituted quinoxalinyl;
$Ar^2$ represents a 5- or 6-membered heterocyclyl group selected from furanyl, thienyl, thiazolyl, imidazolyl, pyridyl, triazolyl, and pyrazolyl, and wherein the heterocyclyl group is substituted by $R^1$ and is further optionally substituted, or
$Ar^2$ represents an optionally substituted bicyclic heteroaromatic group selected from benzofuryl, benzimidazolyl, quinolinyl, quinoxalinyl, benzotriazolyl, benzothienyl, isoquinolyl, indolyl, and benzothiazolyl;
$R^1$ represents hydrogen, optionally substituted$(C_{1-4})$alkoxy, halo, cyano, optionally substituted$(C_{1-6})$alkyl, or optionally substituted phenyl;
wherein said optionally substituted $Ar^1$, $Ar^2$, and $R^1$ is optionally substituted by halogen, hydroxy, oxo, cyano, nitro, $(C_{1-4})$alkyl, $(C_{1-4})$alkoxy, hydroxy$(C_{1-4})$alkyl, hydroxy$(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$ alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$ alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$ alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, aryl$(C_{1-4})$ alkanoyl, $(C_{1-4})$acyl, aryl, aryl$(C_{1-4})$alkyl, $(C_{1-4})$alkylamino$(C_{1-4})$alkyl, $R^aR^bN$—, $R^aOCO(CH_2)_r$, $R^aCON(R^a)(CH_2)_r$, $R^aR^bNCO(CH_2)_r$, $R^aR^bNSO_2(CH_2)_r$ or $R^aSO_2NR^b(CH_2)_r$, wherein r represents zero or an integer from 1 to 4, or $R^aR^bN(CH_2)n$- or $R^aR^bN(CH_2)nO$—, wherein n represents an integer from 1 to 4, wherein each of $R^a$ and $R^b$ independently represents a hydrogen atom or a $(C_{1-4})$alkyl group or $R^aR^b$ forms part of a $(C_{3-6})$ azacycloalkane or $(C_{3-6})$(2-oxo)azacycloalkane ring, or $R^aR^bN(CH_2)n$- or $R^aR^bN(CH_2)nO$, where $R^a$ with at least one $CH_2$ of the $(CH_2)n$ portion of the group form a $(C_{3-6})$azacycloalkane and $R^b$ represents hydrogen, a $(C_{1-4})$ alkyl group or with the nitrogen to which it is attached forms a second $(C_{3-6})$azacycloalkane fused to the first $(C_{3-6})$azacycloalkane;
or a pharmaceutically acceptable salt thereof.

2. A compound of formula (Ia):

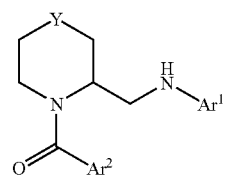

wherein:
Y represents a group $(CH_2)_n$, wherein n represents 1;
$Ar^1$ is optionally substituted quinoxalinyl;
$Ar^2$ represents a 5- or 6-membered heterocyclyl group selected from furanyl, thienyl, thiazolyl, imidazolyl, pyridyl, triazolyl, and pyrazolyl, wherein the heterocyclyl group is substituted by $R^1$ and is further optionally substituted;
$R^1$ represents hydrogen, optionally substituted$(C_{1-4})$alkoxy, halo, cyano, optionally substituted$(C_{1-6})$alkyl, or optionally substituted phenyl;
wherein said optionally substituted $Ar^1$, $Ar^2$, and $R^1$ is optionally substituted by halogen, hydroxy, oxo, cyano, nitro, $(C_{1-4})$alkyl, $(C_{1-4})$alkoxy, hydroxy$(C_{1-4})$alkyl, hydroxy$(C_{1-4})$alkoxy, halo$(C_{1-4})$alkyl, halo$(C_{1-4})$ alkoxy, aryl$(C_{1-4})$alkoxy, $(C_{1-4})$alkylthio, hydroxy $(C_{1-4})$alkyl, $(C_{1-4})$alkoxy$(C_{1-4})$alkyl, $(C_{3-6})$cycloalkyl $(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxy, $(C_{1-4})$ alkylsulfonyl($C_{1-4}$)alkyl, arylsulfonyl, arylsulfonyloxy, arylsulfonyl , ($C_{1-4}$)alkyl, ($C_{1-4}$)alkylsulfonamido, ($C_{1-4}$)alkylamido, ($C_{1-4}$)alkylsulfonamido($C_{1-4}$)alkyl, ($C_{1-4}$)alkylamido($C_{1-4}$)alkyl, arylsulfonamido, arylcarboxamido, arylsulfonamido($C_{1-4}$)alkyl, arylcarboxamido($C_{1-4}$)alkyl, aroyl, aroyl($C_{1-4}$)alkyl, aryl($C_{1-4}$)alkanoyl, ($C_{1-4}$)acyl, aryl, aryl($C_{1-4}$)alkyl, ($C_{1-4}$) alkylamino($C_{1-4}$)alkyl, $R^aR^bN$—, $R^aOCO(CH_2)_r$, $R^aCON(R^a)(CH_2)_r$, $R^aR^bNCO(CH_2)_r$, $R_aR^bNSO_2(CH_2)_r$ or $R^aSO_2NR^b(CH_2)_r$, wherein r represents zero or an integer from 1 to 4, or $R^aR^bN(CH_2)n$— or $R^aR^bN(CH_2)nO$—, wherein n represents an integer from 1 to 4, wherein each of $R^a$ and $R^b$ independently represents a hydrogen atom or a ($C_{1-4}$)alkyl group or $R^aR^b$ forms part of a ($C_{3-6}$)azacycloalkane or ($C_{3-6}$)(2-oxo)azacycloalkane ring, or $R^aR^bN(CH_2)n$- or $R^aR^bN(CH_2)nO$, where $R^a$ with at least one $CH_2$ of the $(C_2)n$ portion of the group form a ($C_{3-6}$)azacycloalkane and $R^b$ represents hydrogen, a ($C_{1-4}$)alkyl group or with the nitrogen to which it is attached forms a second ($C_{3-6}$)azacycloalkane fused to the first ($C_{3-6}$)azacycloalkane;
or a pharmaceutically acceptable salt thereof.

3. A compound according to claim 1, wherein $Ar^2$ represents an optionally substituted pyridyl, thiazolyl, pyrazolyl, benzofuryl, triazolyl, quinoxalinyl, quinolinyl, isoquinolinyl, benzimidazolyl, benzothienyl, benzotriazolyl, benzothiazolyl, indolyl or thienyl.

4. A compound according to claim 2, wherein $Ar^2$ represents an optionally substituted pyridyl, thiazolyl, pyrazolyl, triazolyl, or thienyl.

5. A compound according to claim 1, wherein $R^1$ is selected from a trifluoromethoxy, methoxy, ethoxy, halo, cyano or an optionally substituted phenyl group.

6. A compound according to claim 2, wherein $R^1$ is selected from a trifluoromethoxy, methoxy, ethoxy, halo, cyano or an optionally substituted phenyl group.

7. A pharmaceutical composition comprising a therapeutically effective amount of the compound according to claim 1, or a pharmaceutically acceptable salt thereof, and a pharmaceutically acceptable carrier.

8. A pharmaceutical composition comprising a therapeutically effective amount of the compound according to claim 2, or a pharmaceutically acceptable salt thereof, and a pharmaceutically acceptable carrier.

9. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is selected from obesity and obesity associated with Type II diabetes.

10. A method of treating a disease or disorder where an antagonist of a human orexin receptor is required, which comprises administering to a subject in need thereof an effective amount of the compound according to claim 1, or a pharmaceutically acceptable salt thereof, wherein said disease or disorder is insomnia.

11. A method of treating a disease or disorder where an antagonist of a human orexin receptor is required, which comprises administering to a subject in need thereof an effective amount of the compound according to claim 2, or a pharmaceutically acceptable salt thereof, wherein said disease or disorder is selected from obesity and obesity associated with Type II diabetes.

12. A method of treating a disease or disorder where an antagonist of a human orexin receptor is required, which comprises administering to a subject in need thereof an effective amount of the compound according to claim 2, or a pharmaceutically acceptable salt thereof, wherein said disease or disorder is insomnia.

13. A compound selected from:
1-[5-(4-Fluoro-phenyl)-2-methyl-thiazol-4-yl]-1-[2-(quinoxalin-2-ylaminomethyl)-piperidin-1-yl]-methanone;
1-{(S)-2-[(6,7-Difluoro-3-methyl-quinoxalin-2-ylamino)-methyl]-piperidin-1-yl}-1-[5-(4-fluoro-phenyl)-2-methyl-thiazol-4yl]-methanone;
1-{(S)-2-[(6,7-Difluoro-3-methyl-quinoxalin-2-ylamino)-methyl]-piperidin-1-yl}-1-[5-(4-fluoro-phenyl)-thiazol-4-yl]methanone;
1-{(S)-2-[(6,7-Difluoro-3-methyl-quinoxalin-2-ylamino)-methyl]-piperidin-1-yl}-1-[4-(4-fluoro-phenyl)-1-methyl-1H-pyrazol-3-yl]-methanone;
1-{(S)-2-[(6,7-Difluoro-3-methyl-quinoxalin-2-ylamino)-methyl]-piperidin-1-yl}-1-[4-(4-fluoro-phenyl)-1H-pyrazol-3-yl]-methanone;
1-{(S)-2-[(6,7-Difluoro-3-methyl-quinoxalin-2-ylamino)-methyl]-piperidin-1-yl}-1-[2-(4-fluoro-phenyl)-5-methyl-2H-pyrazol-3-yl]-methanone;
1-{(S)-2-[(6,7-Difluoro-3-methyl-quinoxalin-2-ylamino)-methyl]-piperidin-1-yl}-1-[4-(4-fluoro-phenyl)-2-methyl-2H-pyrazol-3-yl]-methanone;
1-{(S)-2-[(6,7-Difluoro-quinoxalin-2-ylamino)-methyl]-piperidin-1-yl}-1-quinolin-4-yl-methanone;
1-{(S)-2-[(6,7-Difluoro-quinoxalin-2-ylamino)-methyl]-piperidin-1-yl}-1-[5-(4-fluoro-phenyl)-2-methyl-oxazol-4-yl]-methanone;
1-{(S)-2-[(6,7-Difluoro-quinoxalin-2-ylamino)-methyl]-piperidin-1-yl}-1-[5-(4-fluoro-phenyl)-2-methyl-thiazol-4-yl]-methanone;
1-{(S)-2-[(6,7-Difluoro-quinoxalin-2-ylamino)-methyl]-piperidin-1-yl}-1-[4-(4-fluoro-phenyl)-1-methyl-1H-pyrazol-3-yl]-methanone;
1-{(S)-2-[(6,7-Difluoro-quinoxalin-2-ylamino)-methyl]-piperidin-1-yl}-1-[4-(4-fluoro-phenyl)-2-methyl-2H-pyrazol-3yl]-methanone;
1-{(S)-2-[(6,7-Difluoro-quinoxalin-2-ylamino)-methyl]-piperidin-1-yl}-1-[5-(4-fluoro-phenyl)-2-methyl-2H-[1,2,3]triazol-4-yl]-methanone;
1-{(S)-2-[(6,7-Difluoro-quinoxalin-2-ylamino)-methyl]-piperidin-1-yl}-1-[5-(4-fluoro-phenyl)-thiazol-4yl]-methanone;
1-{(S)-2-[(6,7-Difluoro-quinoxalin-2-ylamino)-methyl]-piperidin-1-yl}-1-quinoxalin-2-yl-methanone;
1-{(S)-2-[(6,7-Difluoro-quinoxalin-2-ylamino)-methyl]-piperidin-1-yl}-1-quinolin-3-yl-methanone;
1-{(S)-2-[(6,7-Difluoro-quinoxalin-2-ylamino)-methyl-]-piperidin-1-yl}-1-isoquinolin-3-yl-methanone;
1-{(S)-2-[(6,7-Difluoro-quinoxalin-2-ylamino)-methyl]-piperidin-1-yl}-1-(2-methoxy-pyridin-3-yl)-methanone;
1-{(S)-2-[(6,7-Difluoro-quinoxalin-2-ylamino)-methyl]-piperidin-1-yl}-1-quinoxalin-6-yl-methanone;
1-{(S)-2-[(6,7-Difluoro-quinoxalin-2-ylamino)-methyl]-piperidin-1-yl}-1-[2-dimethylamino-5-(4-fluoro-phenyl)-thiazol-4-yl]-methanone;
1-((S)-2-{[(6,7-Difluoro-quinoxalin-2-yl)-methyl-amino]-methyl}-piperidin-1-yl)-1-[4-(4-fluoro-phenyl)-1-methyl-1H-pyrazol-3-yl]-methanone;
1-{(S)-2-[(6,7-Difluoro-quinoxalin-2-ylamino)-methyl]-piperidin-1-yl}-1-(4-fluoro-benzofuran-2-yl)-methanone;

1-Benzo[b]thiophen-2-yl-1-{(S)-2-[(6,7-difluoro-quinoxalin-2-ylamino)-methyl]-piperidin-1-yl}-methanone;

1-(1H-Benzoimidazol-5-yl)-1-{(S)-2-[(6,7-difluoro-quinoxalin-2-ylamino)-methyl]-piperidin-1-yl}-methanone;

1-(1H-Benzotriazol-5-yl)-1-{(S)-2-[(6,7-difluoro-quinoxalin-2-ylamino)-methyl]-piperidin-1-yl}-methanone;

1-Benzothiazol-6-yl-1-{(S)-2-[(6,7-difluoro-quinoxalin-2-ylamino)-methyl]-piperidin-1-yl}-methanone;

1-{(S)-2-[(6,7-Difluoro-quinoxalin-2-ylamino)-methyl]-piperidin-1-yl}-1-[4-(4-fluoro-phenyl)-1-(2-methoxy-ethyl)-1H-pyrazol-3-yl]-methanone;

1-{(S)-2-[(6,7-Difluoro-quinoxalin-2-ylamino)-methyl]-piperidin-1-yl}-1-(2,4-dimethyl-thiazol-5-yl)-methanone;

1-{(S)-2-[(6,7-Difluoro-quinoxalin-2-ylamino)-methyl]-piperidin-1-yl}-1-[5-(4-fluoro-phenyl)-1-methyl-1H-[1,2,3]triazol-4-yl]-methanone;

1-{(S)-2-[(6,7-Difluoro-quinoxalin-2-ylamino)-methyl]-piperidin-1-yl}-1-(6-fluoro-benzofuran-2-yl)-methanone;

1-{(S)-2-[(6,7-Difluoro-quinoxalin-2-ylamino)-methyl]-piperidin-1-yl}-1-(5-fluoro-benzofuran-2-yl)-methanone;

1-{(S)-2-[(6,7-Difluoro-quinoxalin-2-ylamino)-methyl]-piperidin-1-yl}-1-(7-fluoro-benzofuran-2-yl)-methanone;

1-(5,7-Difluoro-benzofuran-2-yl)-1-{(S)-2-[(6,7-difluoro-quinoxalin-2-ylamino)-methyl]-piperidin-1-yl}-methanone;

1-{2-[(6,7-Difluoro-quinoxalin-2-ylamino)-methyl]-piperidin-1-yl}-1-{2-[3-(3-dimethylamino-propoxy)-phenyl]-thiophen-3-yl}-methanone;

1-{2-[(6,7-Difluoro-quinoxalin-2-ylamino)-methyl]-piperidin-1-yl}-1-quinolin-8-yl-methanone;

1-{(S)-2-[(6,7-Difluoro-quinoxalin-2-ylamino)-methyl]-piperidin-1-yl}-1-(1-methyl-1H-indol-2-yl)-methanone;

1-{(S)-2-[(6,7-Difluoro-quinoxalin-2-ylamino)-methyl]-piperidin-1-yl}-1-(1H-indol-6-yl)-methanone;

1-Benzo[1,2,3]thiadiazol-5-yl-1-{(S)-2-[(6,7-difluoro-quinoxalin-2-ylamino)-methyl]-piperidin-1-yl}-methanone;

1-{(S)-2-[(6,7-Difluoro-quinoxalin-2-ylamino)-methyl]-piperidin-1-yl}-1-[1-(2-dimethylamino-ethyl)-4-(4-fluoro-phenyl)-1H-pyrazol-3-yl]-methanone;

and a pharmaceutically acceptable salt thereof.

* * * * *

SEQUENCE LISTING

<160> NUMBER OF SEQ ID NOS: 1

<210> SEQ ID NO 1
<211> LENGTH: 35
<212> TYPE: PRT
<213> ORGANISM: Homo sapien

<400> SEQUENCE: 1

Glu Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
            20                  25                  30

Leu Asn His
        35